United States Patent
Skelton et al.

(10) Patent No.: US 8,583,252 B2
(45) Date of Patent: Nov. 12, 2013

(54) PATIENT INTERACTION WITH POSTURE-RESPONSIVE THERAPY

(75) Inventors: Dennis M. Skelton, Bloomington, MN (US); Jon P. Davis, St. Michael, MN (US); Rajeev Sahasrabudhe, Maple Grove, MN (US); Shyam Gokaldas, New Brighton, MN (US); Joseph J. Nolan, Minnetonka, MN (US)

(73) Assignee: Medtronic, Inc., Minneapolis, MN (US)

( * ) Notice: Subject to any disclaimer, the term of this patent is extended or adjusted under 35 U.S.C. 154(b) by 680 days.

(21) Appl. No.: 12/433,325

(22) Filed: Apr. 30, 2009

(65) Prior Publication Data

US 2010/0010575 A1    Jan. 14, 2010

Related U.S. Application Data

(60) Provisional application No. 61/080,009, filed on Jul. 11, 2008.

(51) Int. Cl.
*A61N 1/00* (2006.01)

(52) U.S. Cl.
USPC .............................................. 607/62; 607/46

(58) Field of Classification Search
USPC ................................ 607/40, 41, 62
See application file for complete search history.

(56) References Cited

U.S. PATENT DOCUMENTS

| | | | |
|---|---|---|---|
| 4,297,685 A | 10/1981 | Brainard, II | |
| 4,365,633 A | 12/1982 | Loughman | |
| 4,543,955 A | 10/1985 | Schroeppel | |
| 4,550,736 A | 11/1985 | Broughton et al. | |
| 4,566,456 A | 1/1986 | Koning et al. | |
| 4,771,780 A | 9/1988 | Sholder | |
| 4,776,345 A | 10/1988 | Cohen et al. | |
| 4,846,180 A | 7/1989 | Buffet | |
| 4,846,195 A | 7/1989 | Alt | |

(Continued)

FOREIGN PATENT DOCUMENTS

| | | |
|---|---|---|
| DE | 19831109 | 1/2000 |
| DE | 10024103 | 11/2001 |

(Continued)

OTHER PUBLICATIONS

"Analysis of heart rate dynamics by methods derived from non-linear mathematics: Clinical applicability and prognostic significance," http://herkules.oulu.fi.isbn9514250133/html, 4 pp., 2004.

(Continued)

*Primary Examiner* — Brian T Gedeon
(74) *Attorney, Agent, or Firm* — Shumaker & Sieffert, P.A.

(57) ABSTRACT

In general, the disclosure relates to the delivery of therapy according to a detected posture state of a patient. The disclosure contemplates a variety of techniques for managing therapy delivered to a patent, including patient and clinician interaction with a medical device configured to deliver therapy according to posture state. In one example, the disclosure relates to a technique including receiving an indication from an external device to resume delivery of therapy to a patient that was previously turned off, wherein the therapy that was previously turned off comprises therapy delivered to the patient according to a detected posture state of the patient; obtaining therapy information defining the therapy; and resuming the delivery of therapy to the patient in response to the receipt of the indication, wherein the delivery of therapy is resumed according to the obtained therapy information.

41 Claims, 23 Drawing Sheets

(56) References Cited

U.S. PATENT DOCUMENTS

| | | |
|---|---|---|
| 5,031,618 A | 7/1991 | Mullett |
| 5,040,534 A | 8/1991 | Mann et al. |
| 5,040,536 A | 8/1991 | Riff |
| 5,058,584 A | 10/1991 | Bourgeois |
| 5,125,412 A | 6/1992 | Thornton |
| 5,154,180 A | 10/1992 | Blanchet et al. |
| 5,158,078 A | 10/1992 | Bennett et al. |
| 5,167,229 A | 12/1992 | Peckham et al. |
| 5,233,984 A | 8/1993 | Thompson |
| 5,275,159 A | 1/1994 | Griebel |
| 5,312,446 A | 5/1994 | Holschbach et al. |
| 5,335,657 A | 8/1994 | Terry, Jr. et al. |
| 5,337,758 A | 8/1994 | Moore et al. |
| 5,342,409 A | 8/1994 | Mullett |
| 5,354,317 A | 10/1994 | Alt |
| 5,425,750 A | 6/1995 | Moberg |
| 5,476,483 A | 12/1995 | Bornzin et al. |
| 5,487,755 A | 1/1996 | Snell et al. |
| 5,513,645 A | 5/1996 | Jacobson et al. |
| 5,514,162 A | 5/1996 | Bornzin et al. |
| 5,558,640 A | 9/1996 | Pfeiler et al. |
| 5,562,707 A | 10/1996 | Prochazka et al. |
| 5,593,431 A | 1/1997 | Sheldon |
| 5,622,428 A | 4/1997 | Bonnet |
| 5,628,317 A | 5/1997 | Starkebaum et al. |
| 5,643,332 A | 7/1997 | Stein |
| 5,645,053 A | 7/1997 | Remmers et al. |
| 5,674,258 A | 10/1997 | Henschel et al. |
| 5,711,316 A | 1/1998 | Elsberry et al. |
| 5,720,770 A | 2/1998 | Nappholz et al. |
| 5,732,696 A | 3/1998 | Rapoport et al. |
| 5,741,310 A | 4/1998 | Wittkampf |
| 5,782,884 A | 7/1998 | Stotts et al. |
| 5,814,093 A | 9/1998 | Stein |
| 5,832,932 A | 11/1998 | Elsberry et al. |
| 5,833,709 A | 11/1998 | Rise et al. |
| 5,836,989 A | 11/1998 | Shelton |
| 5,851,193 A | 12/1998 | Arikka et al. |
| 5,865,760 A | 2/1999 | Lidman et al. |
| 5,885,471 A | 3/1999 | Ruben et al. |
| 5,893,883 A | 4/1999 | Torgerson et al. |
| 5,895,371 A | 4/1999 | Levitas et al. |
| 5,904,708 A | 5/1999 | Goedeke |
| 5,911,738 A | 6/1999 | Sikorski et al. |
| 5,913,727 A | 6/1999 | Ahdoot |
| 5,919,149 A | 7/1999 | Allum |
| 5,938,690 A | 8/1999 | Law et al. |
| 5,941,906 A | 8/1999 | Barreras, Sr. et al. |
| 5,944,680 A | 8/1999 | Christopherson et al. |
| 5,957,957 A | 9/1999 | Sheldon |
| 6,027,456 A | 2/2000 | Feler et al. |
| 6,038,475 A | 3/2000 | Sikorski et al. |
| 6,044,297 A | 3/2000 | Sheldon et al. |
| 6,045,513 A | 4/2000 | Stone et al. |
| 6,059,576 A | 5/2000 | Brann |
| 6,095,991 A | 8/2000 | Krausman et al. |
| 6,099,479 A | 8/2000 | Christopherson et al. |
| 6,102,874 A | 8/2000 | Stone et al. |
| 6,120,467 A | 9/2000 | Schallhorn |
| 6,128,534 A | 10/2000 | Park et al. |
| 6,134,459 A | 10/2000 | Roberts et al. |
| 6,157,857 A | 12/2000 | Dimpfel |
| 6,165,143 A | 12/2000 | Van Lummel |
| 6,216,537 B1 | 4/2001 | Henschel et al. |
| 6,259,948 B1 | 7/2001 | Florio et al. |
| 6,280,409 B1 | 8/2001 | Stone et al. |
| 6,296,606 B1 | 10/2001 | Goldberg et al. |
| 6,308,098 B1 | 10/2001 | Meyer |
| 6,308,099 B1 | 10/2001 | Fox et al. |
| 6,315,740 B1 | 11/2001 | Singh |
| 6,327,501 B1 | 12/2001 | Levine et al. |
| 6,341,236 B1 | 1/2002 | Osorio et al. |
| 6,351,672 B1 | 2/2002 | Park et al. |
| 6,368,284 B1 | 4/2002 | Bardy |
| 6,381,496 B1 | 4/2002 | Meadows et al. |
| 6,393,325 B1 | 5/2002 | Mann et al. |
| 6,438,408 B1 | 8/2002 | Mulligan et al. |
| 6,440,090 B1 | 8/2002 | Schallhorn |
| 6,449,508 B1 | 9/2002 | Sheldon et al. |
| 6,459,934 B1 | 10/2002 | Kadhiresan |
| 6,466,821 B1 | 10/2002 | Pianca et al. |
| 6,468,234 B1 | 10/2002 | Van der Loos et al. |
| 6,507,757 B1 | 1/2003 | Swain et al. |
| 6,514,218 B2 | 2/2003 | Yamamoto |
| 6,516,749 B1 | 2/2003 | Salasidis |
| 6,539,249 B1 | 3/2003 | Kadhiresan et al. |
| 6,547,755 B1 | 4/2003 | Lippe et al. |
| 6,572,557 B2 | 6/2003 | Tchou et al. |
| 6,574,507 B1 | 6/2003 | Bonnet |
| 6,605,038 B1 | 8/2003 | Teller et al. |
| 6,609,031 B1 | 8/2003 | Law et al. |
| 6,611,783 B2 | 8/2003 | Kelly, Jr. et al. |
| 6,620,151 B2 | 9/2003 | Blischak et al. |
| 6,625,493 B2 | 9/2003 | Kroll et al. |
| 6,635,048 B1 | 10/2003 | Ullestad et al. |
| 6,641,542 B2 | 11/2003 | Cho et al. |
| 6,658,292 B2 | 12/2003 | Kroll et al. |
| 6,659,968 B1 | 12/2003 | McClure |
| 6,662,047 B2 | 12/2003 | Sorensen |
| 6,665,558 B2 | 12/2003 | Kalgren et al. |
| 6,668,188 B2 | 12/2003 | Sun et al. |
| 6,687,538 B1 | 2/2004 | Hrdlicka et al. |
| 6,731,984 B2 | 5/2004 | Cho et al. |
| 6,740,075 B2 | 5/2004 | Lebel et al. |
| 6,748,276 B1 | 6/2004 | Daignault, Jr. et al. |
| 6,752,766 B2 | 6/2004 | Kowallik et al. |
| 6,773,404 B2 | 8/2004 | Poezevera et al. |
| 6,782,315 B2 | 8/2004 | Lu et al. |
| 6,817,979 B2 | 11/2004 | Nihtilä |
| 6,820,025 B2 | 11/2004 | Bachmann et al. |
| 6,829,507 B1 | 12/2004 | Lidman et al. |
| 6,832,113 B2 | 12/2004 | Belalcazar |
| 6,834,436 B2 | 12/2004 | Townsend |
| 6,853,863 B2 | 2/2005 | Carter et al. |
| 6,878,121 B2 | 4/2005 | Krausman et al. |
| 6,884,596 B2 | 4/2005 | Civelli et al. |
| 6,890,306 B2 | 5/2005 | Poezevera |
| 6,895,341 B2 | 5/2005 | Barrey et al. |
| 6,922,587 B2 | 7/2005 | Weinberg |
| 6,923,784 B2 | 8/2005 | Stein |
| 6,928,324 B2 | 8/2005 | Park et al. |
| 6,937,899 B2 | 8/2005 | Sheldon et al. |
| 6,937,900 B1 | 8/2005 | Pianca et al. |
| 6,945,934 B2 | 9/2005 | Bardy |
| 6,964,641 B2 | 11/2005 | Cho et al. |
| 6,975,904 B1 | 12/2005 | Sloman |
| 6,997,882 B1 | 2/2006 | Parker et al. |
| 6,999,817 B2 | 2/2006 | Park et al. |
| 7,016,730 B2 | 3/2006 | Ternes |
| 7,031,772 B2 | 4/2006 | Condie |
| 7,043,305 B2 | 5/2006 | KenKnight et al. |
| 7,054,687 B1 | 5/2006 | Andersen |
| 7,066,910 B2 | 6/2006 | Bauhahn et al. |
| 7,082,333 B1 | 7/2006 | Bauhahn |
| 7,092,759 B2 | 8/2006 | Nehls et al. |
| 7,095,424 B2 | 8/2006 | Satoh et al. |
| 7,110,820 B2 | 9/2006 | Tcheng et al. |
| 7,117,036 B2 | 10/2006 | Florio |
| 7,123,967 B2 | 10/2006 | Weinberg |
| 7,130,681 B2 | 10/2006 | Gebhardt et al. |
| 7,130,689 B1 | 10/2006 | Turcott |
| 7,141,026 B2 | 11/2006 | Aminian et al. |
| 7,142,921 B2 | 11/2006 | Mattes et al. |
| 7,149,579 B1 | 12/2006 | Koh et al. |
| 7,149,584 B1 | 12/2006 | Koh et al. |
| 7,151,961 B1 | 12/2006 | Whitehurst et al. |
| 7,155,279 B2 | 12/2006 | Whitehurst et al. |
| 7,160,252 B2 | 1/2007 | Cho et al. |
| 7,162,304 B1 | 1/2007 | Bradley |
| 7,167,743 B2 | 1/2007 | Heruth et al. |
| 7,167,751 B1 | 1/2007 | Whitehurst et al. |
| 7,181,281 B1 | 2/2007 | Kroll |
| 7,189,204 B2 | 3/2007 | Ni et al. |
| 7,207,947 B2 | 4/2007 | Koh et al. |

(56) References Cited

U.S. PATENT DOCUMENTS

| | | |
|---|---|---|
| 7,210,240 B2 | 5/2007 | Townsend et al. |
| 7,212,862 B2 | 5/2007 | Park et al. |
| 7,214,197 B2 | 5/2007 | Prass |
| 7,218,964 B2 | 5/2007 | Hill et al. |
| 7,218,968 B2 | 5/2007 | Condie et al. |
| 7,221,979 B2 | 5/2007 | Zhou et al. |
| 7,231,254 B2 | 6/2007 | DiLorenzo |
| 7,242,983 B2 | 7/2007 | Frei et al. |
| 7,252,640 B2 | 8/2007 | Ni et al. |
| 7,266,412 B2 | 9/2007 | Stypulkowski |
| 7,308,311 B2 | 12/2007 | Sorensen et al. |
| 7,313,440 B2 | 12/2007 | Miesel |
| 7,317,948 B1 | 1/2008 | King et al. |
| 7,330,760 B2 | 2/2008 | Heruth et al. |
| 7,366,569 B2 | 4/2008 | Belalcazar |
| 7,366,572 B2 | 4/2008 | Heruth et al. |
| 7,387,610 B2 | 6/2008 | Stahmann |
| 7,389,147 B2 | 6/2008 | Wahlstrand et al. |
| 7,395,113 B2 | 7/2008 | Heruth |
| 7,403,820 B2 | 7/2008 | DiLorenzo |
| 7,406,351 B2 | 7/2008 | Wesselink |
| 7,415,308 B2 | 8/2008 | Gerber et al. |
| 7,447,545 B2 | 11/2008 | Heruth et al. |
| 7,471,290 B2 | 12/2008 | Wang et al. |
| 7,471,980 B2 | 12/2008 | Koshiol |
| 7,489,970 B2 | 2/2009 | Lee et al. |
| 7,491,181 B2 | 2/2009 | Heruth et al. |
| 7,505,815 B2 | 3/2009 | Lee et al. |
| 7,519,431 B2 | 4/2009 | Goetz et al. |
| 7,542,803 B2 | 6/2009 | Heruth et al. |
| 7,548,786 B2 | 6/2009 | Lee et al. |
| 7,559,901 B2 | 7/2009 | Maile |
| 7,572,225 B2 | 8/2009 | Stahmann |
| 7,577,479 B2 | 8/2009 | Hartley et al. |
| 7,580,752 B2 | 8/2009 | Gerber et al. |
| 7,584,808 B2 | 9/2009 | Dolgin et al. |
| 7,590,453 B2 | 9/2009 | Heruth |
| 7,590,455 B2 | 9/2009 | Heruth et al. |
| 7,590,481 B2 | 9/2009 | Lu et al. |
| 7,591,265 B2 | 9/2009 | Lee et al. |
| 7,603,170 B2 | 10/2009 | Hatlestad et al. |
| 7,623,919 B2 | 11/2009 | Goetz et al. |
| 7,634,379 B2 | 12/2009 | Noble |
| 7,664,546 B2 | 2/2010 | Hartley et al. |
| 7,672,806 B2 | 3/2010 | Tronconi |
| 7,717,848 B2 | 5/2010 | Heruth et al. |
| 7,769,464 B2 | 8/2010 | Gerber et al. |
| 7,792,583 B2 | 9/2010 | Heruth et al. |
| 8,332,041 B2 * | 12/2012 | Skelton et al. .................. 607/62 |
| 2002/0038137 A1 | 3/2002 | Stein |
| 2002/0091308 A1 | 7/2002 | Kipshidze et al. |
| 2002/0107553 A1 | 8/2002 | Hill et al. |
| 2002/0115939 A1 | 8/2002 | Mulligan et al. |
| 2002/0156504 A1 | 10/2002 | Chen et al. |
| 2002/0165586 A1 | 11/2002 | Hill et al. |
| 2002/0169485 A1 | 11/2002 | Pless et al. |
| 2002/0170193 A1 | 11/2002 | Townsend et al. |
| 2003/0004423 A1 | 1/2003 | Lavie et al. |
| 2003/0036783 A1 | 2/2003 | Bauhahn et al. |
| 2003/0045910 A1 | 3/2003 | Sorensen et al. |
| 2003/0065370 A1 | 4/2003 | Lebel et al. |
| 2003/0088185 A1 | 5/2003 | Prass |
| 2003/0149457 A1 | 8/2003 | Tcheng et al. |
| 2003/0171791 A1 | 9/2003 | KenKnight et al. |
| 2003/0181960 A1 | 9/2003 | Carter et al. |
| 2003/0204211 A1 | 10/2003 | Condie et al. |
| 2004/0015103 A1 | 1/2004 | Aminian et al. |
| 2004/0049132 A1 | 3/2004 | Barron et al. |
| 2004/0088020 A1 | 5/2004 | Condie et al. |
| 2004/0102814 A1 | 5/2004 | Sorensen et al. |
| 2004/0133248 A1 | 7/2004 | Frei et al. |
| 2004/0138716 A1 | 7/2004 | Kon et al. |
| 2004/0147975 A1 | 7/2004 | Popovic et al. |
| 2004/0199215 A1 | 10/2004 | Lee et al. |
| 2004/0199216 A1 | 10/2004 | Lee et al. |
| 2004/0199217 A1 | 10/2004 | Lee et al. |
| 2004/0199218 A1 | 10/2004 | Lee et al. |
| 2004/0215286 A1 | 10/2004 | Stypulkowski |
| 2004/0220621 A1 | 11/2004 | Zhou et al. |
| 2004/0225332 A1 | 11/2004 | Gebhardt et al. |
| 2004/0257693 A1 | 12/2004 | Ehrlich |
| 2005/0042589 A1 | 2/2005 | Hatlestad et al. |
| 2005/0043767 A1 | 2/2005 | Belalcazar |
| 2005/0060001 A1 | 3/2005 | Singhal et al. |
| 2005/0061320 A1 | 3/2005 | Lee et al. |
| 2005/0113710 A1 | 5/2005 | Stahmann et al. |
| 2005/0113887 A1 | 5/2005 | Bauhahn |
| 2005/0126026 A1 | 6/2005 | Townsend et al. |
| 2005/0137627 A1 | 6/2005 | Koshiol et al. |
| 2005/0145246 A1 | 7/2005 | Hartley et al. |
| 2005/0172311 A1 | 8/2005 | Hjelt et al. |
| 2005/0177192 A1 | 8/2005 | Rezai et al. |
| 2005/0209511 A1 | 9/2005 | Heruth et al. |
| 2005/0209512 A1 | 9/2005 | Heruth et al. |
| 2005/0209513 A1 | 9/2005 | Heruth et al. |
| 2005/0209643 A1 | 9/2005 | Heruth et al. |
| 2005/0209644 A1 | 9/2005 | Heruth et al. |
| 2005/0209645 A1 | 9/2005 | Heruth et al. |
| 2005/0215847 A1 | 9/2005 | Heruth et al. |
| 2005/0215947 A1 | 9/2005 | Heruth et al. |
| 2005/0216064 A1 | 9/2005 | Heruth et al. |
| 2005/0222522 A1 | 10/2005 | Heruth et al. |
| 2005/0222638 A1 | 10/2005 | Foley et al. |
| 2005/0228455 A1 | 10/2005 | Kramer et al. |
| 2005/0234514 A1 | 10/2005 | Heruth et al. |
| 2005/0234518 A1 | 10/2005 | Heruth et al. |
| 2005/0240242 A1 | 10/2005 | DiLorenzo |
| 2005/0245988 A1 * | 11/2005 | Miesel .................. 607/46 |
| 2005/0283210 A1 | 12/2005 | Blischak et al. |
| 2006/0190049 A1 | 8/2006 | Gerber et al. |
| 2006/0190050 A1 | 8/2006 | Gerber et al. |
| 2006/0190051 A1 | 8/2006 | Gerber et al. |
| 2006/0195051 A1 | 8/2006 | Schnapp et al. |
| 2006/0206167 A1 | 9/2006 | Flaherty et al. |
| 2006/0212080 A1 | 9/2006 | Hartley et al. |
| 2006/0213267 A1 | 9/2006 | Tronconi et al. |
| 2006/0235289 A1 | 10/2006 | Wesselink et al. |
| 2006/0235472 A1 | 10/2006 | Goetz et al. |
| 2006/0241513 A1 | 10/2006 | Hatlestad et al. |
| 2006/0247724 A1 * | 11/2006 | Gerber et al. .................. 607/41 |
| 2006/0247732 A1 | 11/2006 | Wesselink |
| 2006/0247739 A1 | 11/2006 | Wahlstrand et al. |
| 2006/0259099 A1 | 11/2006 | Goetz et al. |
| 2006/0262120 A1 | 11/2006 | Rosenberg |
| 2006/0265025 A1 | 11/2006 | Goetz et al. |
| 2006/0287686 A1 | 12/2006 | Cullen et al. |
| 2007/0015976 A1 | 1/2007 | Miesel et al. |
| 2007/0038265 A1 | 2/2007 | Tcheng et al. |
| 2007/0050715 A1 | 3/2007 | Behar |
| 2007/0073355 A1 | 3/2007 | DiLorenzo et al. |
| 2007/0115277 A1 | 5/2007 | Wang et al. |
| 2007/0118056 A1 | 5/2007 | Wang et al. |
| 2007/0123758 A1 | 5/2007 | Miesel et al. |
| 2007/0129622 A1 | 6/2007 | Bourget et al. |
| 2007/0129641 A1 | 6/2007 | Sweeney |
| 2007/0129769 A1 | 6/2007 | Bourget et al. |
| 2007/0129774 A1 | 6/2007 | Bourget et al. |
| 2007/0150026 A1 | 6/2007 | Bourget et al. |
| 2007/0150029 A1 | 6/2007 | Bourget et al. |
| 2007/0213789 A1 | 9/2007 | Nolan et al. |
| 2007/0249968 A1 | 10/2007 | Miesel et al. |
| 2007/0250121 A1 | 10/2007 | Miesel et al. |
| 2007/0250134 A1 | 10/2007 | Miesel et al. |
| 2007/0255118 A1 | 11/2007 | Miesel et al. |
| 2007/0255154 A1 | 11/2007 | Lu et al. |
| 2007/0265664 A1 | 11/2007 | Gerber et al. |
| 2007/0265681 A1 | 11/2007 | Gerber et al. |
| 2007/0276439 A1 | 11/2007 | Miesel et al. |
| 2007/0293737 A1 | 12/2007 | Heruth et al. |
| 2007/0293917 A1 | 12/2007 | Thompson |
| 2008/0071150 A1 | 3/2008 | Miesel et al. |
| 2008/0071324 A1 | 3/2008 | Miesel et al. |
| 2008/0071326 A1 | 3/2008 | Heruth et al. |
| 2008/0071327 A1 | 3/2008 | Miesel et al. |

(56) References Cited

U.S. PATENT DOCUMENTS

| | | |
|---|---|---|
| 2008/0079444 A1 | 4/2008 | Denison |
| 2008/0081958 A1 | 4/2008 | Denison et al. |
| 2008/0114219 A1 | 5/2008 | Zhang et al. |
| 2008/0164979 A1 | 7/2008 | Otto |
| 2008/0177355 A1 | 7/2008 | Miesel et al. |
| 2008/0188901 A1 | 8/2008 | Sanghera et al. |
| 2008/0188909 A1 | 8/2008 | Bradley |
| 2008/0194998 A1 | 8/2008 | Holmstrom et al. |
| 2008/0204255 A1 | 8/2008 | Flexer et al. |
| 2008/0269812 A1 | 10/2008 | Gerber et al. |
| 2008/0269843 A1 | 10/2008 | Gerber |
| 2008/0281376 A1 | 11/2008 | Gerber et al. |
| 2008/0281379 A1 | 11/2008 | Wesselink |
| 2008/0281381 A1 | 11/2008 | Gerber et al. |
| 2008/0288200 A1 | 11/2008 | Noble |
| 2008/0300449 A1 | 12/2008 | Gerber et al. |
| 2008/0300470 A1 | 12/2008 | Gerber et al. |
| 2009/0030263 A1 | 1/2009 | Heruth et al. |
| 2009/0036951 A1 | 2/2009 | Heruth et al. |
| 2009/0046056 A1 | 2/2009 | Rosenberg et al. |
| 2009/0076343 A1 | 3/2009 | Kristofer et al. |
| 2009/0082829 A1 | 3/2009 | Panken et al. |
| 2009/0099627 A1 | 4/2009 | Molnar et al. |
| 2009/0105785 A1 | 4/2009 | Wei et al. |
| 2009/0118599 A1 | 5/2009 | Heruth et al. |
| 2009/0228841 A1 | 9/2009 | Hildreth |
| 2009/0233770 A1 | 9/2009 | Vincent et al. |
| 2009/0259216 A1 | 10/2009 | Drew et al. |
| 2009/0264789 A1 | 10/2009 | Molnar et al. |
| 2009/0306740 A1 | 12/2009 | Heruth et al. |
| 2010/0010380 A1 | 1/2010 | Panken et al. |
| 2010/0010381 A1 | 1/2010 | Skelton et al. |
| 2010/0010382 A1 | 1/2010 | Panken et al. |
| 2010/0010383 A1 | 1/2010 | Skelton et al. |
| 2010/0010384 A1 | 1/2010 | Panken et al. |
| 2010/0010385 A1 | 1/2010 | Skelton et al. |
| 2010/0010386 A1 | 1/2010 | Skelton et al. |
| 2010/0010387 A1 | 1/2010 | Skelton et al. |
| 2010/0010388 A1 | 1/2010 | Panken et al. |
| 2010/0010389 A1 | 1/2010 | Davis et al. |
| 2010/0010390 A1 | 1/2010 | Skelton et al. |
| 2010/0010391 A1 | 1/2010 | Skelton et al. |
| 2010/0010392 A1 | 1/2010 | Skelton et al. |
| 2010/0010432 A1 | 1/2010 | Skelton et al. |
| 2010/0010571 A1 | 1/2010 | Skelton et al. |
| 2010/0010572 A1 | 1/2010 | Skelton et al. |
| 2010/0010573 A1 | 1/2010 | Skelton et al. |
| 2010/0010574 A1 | 1/2010 | Skelton et al. |
| 2010/0010576 A1 | 1/2010 | Skelton et al. |
| 2010/0010577 A1 | 1/2010 | Skelton et al. |
| 2010/0010578 A1 | 1/2010 | Skelton et al. |
| 2010/0010579 A1 | 1/2010 | Skelton et al. |
| 2010/0010580 A1 | 1/2010 | Skelton et al. |
| 2010/0010583 A1 | 1/2010 | Panken et al. |
| 2010/0010584 A1 | 1/2010 | Skelton et al. |
| 2010/0010585 A1 | 1/2010 | Davis et al. |
| 2010/0010586 A1 | 1/2010 | Skelton et al. |
| 2010/0010587 A1 | 1/2010 | Skelton et al. |
| 2010/0010588 A1 | 1/2010 | Skelton et al. |
| 2010/0010589 A1 | 1/2010 | Skelton et al. |
| 2010/0010590 A1 | 1/2010 | Skelton et al. |
| 2010/0030286 A1 | 2/2010 | Goetz et al. |
| 2010/0121415 A1 | 5/2010 | Skelton et al. |
| 2010/0174155 A1 | 7/2010 | Heruth et al. |

FOREIGN PATENT DOCUMENTS

| | | |
|---|---|---|
| EP | 0564803 | 10/1993 |
| EP | 0845240 | 6/1998 |
| EP | 0849715 | 6/1998 |
| EP | 1195139 | 4/2002 |
| EP | 1291036 | 3/2003 |
| EP | 1308182 | 5/2003 |
| EP | 1391846 | 2/2004 |
| EP | 1437159 | 7/2004 |
| EP | 1731088 | 12/2006 |
| EP | 1870128 | 12/2007 |
| EP | 1938862 | 7/2008 |
| GB | 2330912 | 5/1999 |
| GB | 2408342 | 5/2005 |
| GB | 2447647 | 9/2008 |
| WO | 94/05371 | 3/1994 |
| WO | 96/29007 | 9/1996 |
| WO | 97/04705 | 2/1997 |
| WO | 97/49455 | 12/1997 |
| WO | 98/00197 | 1/1998 |
| WO | 99/56820 | 11/1999 |
| WO | 01/37930 | 5/2001 |
| WO | 02/28282 | 4/2002 |
| WO | 02/41771 | 5/2002 |
| WO | 02/087433 | 11/2002 |
| WO | 02/096512 | 12/2002 |
| WO | 02/100267 | 12/2002 |
| WO | 03/051356 | 6/2003 |
| WO | 03/065891 | 8/2003 |
| WO | 2005/028029 | 3/2005 |
| WO | 2005/035050 | 4/2005 |
| WO | 2005/079487 | 9/2005 |
| WO | 2005/089646 | 9/2005 |
| WO | 2005/089647 | 9/2005 |
| WO | 2005/089860 | 9/2005 |
| WO | 2005/102499 | 11/2005 |
| WO | 2005/120348 | 12/2005 |
| WO | 2007/009088 | 1/2007 |
| WO | 2007/051196 | 5/2007 |
| WO | 2007/064682 | 6/2007 |
| WO | 2007/064936 | 6/2007 |
| WO | 2008/026970 | 3/2008 |

OTHER PUBLICATIONS

"Design Competition: Runners-Up for the Best Three Designs," EPN, vol. 26, No. 1, 1 pg., 2002.

"IBM and Citizen Watch develop Linux-Based WatchPad," http://wwwlinuxdevices.com/news/NS6580187845.html, 5 pp., 2006.

"MiniMitter® Physiological and Behavioral Monitoring for Humans and Animals," http://www.minimitter.com/Products/Actiwatch, 3 pp., 2006.

"Watch," Wikipedia, 6 pp., http://en.wikipedia.org/wiki/Watch, 2006.

Aminian et al., "Physical Activity Monitoring Based on Accelerometry: Validation and Comparison with Video Observation," Medical & Biological Engineering and Computing, vol. 37, No. 2, pp. 304-308, 1999.

Amzica, "Physiology of Sleep and Wakefulness as it Relates to the Physiology of Epilepsy," Journal of Clinical Neurophysiology, American Clinical Neurophysiology Society, 19(6)1, pp. 488-503, 2002.

Ang et al., "Physical model of a MEMS accelerometer for low-g motion tracking applications," 2004 IEEE International Conference on Robotics and Automation, vol. 2, pp. 1345-1351, 2004.

Buchser et al., "Improved Physical Activity in Patients Treated for Chronic Pain by Spinal Cord Stimulation," Neuromodulation, vol. 8, Issue 1, pp. 40-48, Mar. 2005.

Crago et al., "An Elbow Extension Neuroprosthesis for Individuals with Tetraplegia," IEEE Transactions on Rehabilitation Engineering, vol. 6, No. 1, pp. 1-6, Mar. 1998.

Dejnabadi et al., "Estimation and Visualization of Sagittal Kinematics of Lower Limbs Orientation Using Body-Fixed Sensors," IEEE Transactions on Biomedical Engineering, vol. 53, No. 7, pp. 1385-1393, Jul. 2006.

Dinner, "Effect of Sleep on Epilepsy," Journal of Clinical Neurophysiology, American Clinical Neurophysiology Society, 19(6), pp. 504-513, 2002.

Foerster et al., "Motion Pattern and Posture: Correctly Assessed by Calibrated Accelerometers," Forschungsgrupe Psychophysiologie, Universität Freiburg, Germany, Mar. 2000, 28 pp.

Foldvary-Schaefer, "Sleep Complaints and Epilepsy: The Role of Seizures, Antiepileptic Drugs and Sleep Disorders," Journal of Clinical Neurophysiology, American Clinical Neurophysiology Society, 19(6), pp. 514-521, 2002.

(56) References Cited

OTHER PUBLICATIONS

Fourcade et al., "Modeling Phase Transitions in Human Posture," Studies in Perception and Action VII, Sheena Rogers & Judith Effken (eds), Lawrence Erlbaum Associated, Inc., pp. 99-103, 2003.
Giansanti et al., "The development and test of a device for the reconstruction of 3-D position and orientation by means of a kinematic sensor assembly with rate gyroscopes and accelerometers," IEEE Transactions on Biomedical Engineering, v. 52, No. 7, pp. 1271-1277, Jul. 2005.
Goodrich et al., "The Prediction of Pain Using Measures of Sleep Quality," Pain Digest, 8:23-25, 1998.
Heinz et al., "Using Wearable Sensors for Real-time Recognition Tasks in Games of Martial Arts—An Initial Experiment," Institute for Computer Systems and Networks (CSN), UMIT—University of Health Systems, Medical Informatics and Technology Hall in Tyrol, Austria, 2006 5 pp. http://eis.comp.lancs.ac.uk/fileadmin/relate/publication/2006-WearableSensors.pdf.
Hendelman et al., "Validity of Accelerometry for the Assessment of Moderate Intensity Physical Activity in the Field," Medicine & Science in Sports & Exercise, pp. S442-S449, 2000.
Hinckley, K., Pierce, J., Sinclair, M., Horvitz, E., *Sensing Techniques for Mobile Interaction*, ACM UIST 2000 Symposium on User Interface Software & Technology, CHI Letters 2 (2), pp. 91-100.
Husak, "Model of Tilt Sensor Systems," ICECS 2002, $9^{th}$ IEEE International Conference on Electronics, Circuits and Systems, vol. 1, pp. 227-230, 2002.
Karantonis et al., "Implementation of a Real-Time Human Movement Classifier Using a Triaxial Accelerometer for Ambulatory Monitoring," IEEE Transactions on Information Technology in Biomedicine, vol. 10, No. 1, pp. 156-167, Jan. 2006.
Kassam, "2005 EDP Topic "MK4": Tremor Data-Logger for Parkinson's Disease Patients," http://www.ee.ryerson.ca/~courses/edp2005/MK4.html, 3 pp., 2005.
Kerr et al., "Analysis of the sit-stand-sit movement cycle in normal subjects," Clinical Biomechanics, vol. 12, No. 4, pp. 236-245, 1977.
Kiani et al., "Computerized Analysis of Daily Life Motor Activity for Ambulatory Monitoring," Technology and Health Care 5, pp. 307-318, 1997.
Kitchin et al., "Compensating for the 0 g Offset Drift of the ADXL50 Accelerometer," Analog Devices Application Note AN-380, 2 pp.
Lau, "Strategies for Generating Prolonged Functional Standing Using Intramuscular Stimulation or Intraspinal Microstimulation," IEEE Transactions on Neural Systems and Rehabilitation Engineering, vol. 15 No. 2, pp. 273-285, Jun. 2007.
Leiper et al., "Sensory Feedback for Head Control in Cerebral Palsy," Physical Therapy, vol. 61, No. 4, pp. 512-518, Apr. 1981.
Lorussi, "Wearable, Redundant Fabric-Based Sensor Arrays for Reconstruction of Body Segment Posture," IEEE Sensors Journal, vol. 4, No. 6, pp. 808-817, Dec. 2004.
Mathie et al., "A Pilot Study of Long-Term Monitoring of Human Movements in the Home Using Accelerometer," Journal of Telemedicine and Telecare10:144-151, Jun. 2007.
Mathie et al., "Determining Activity Using a Triaxial Accelerometer," Proceedings of the Second Joint EMBS/BMES Conference, Houston, TX, pp. 2481-2482, Oct. 23-26, 2002.
Mattmann et al., "Recognizing Upper Body Postures Using Textile Strain Sensors," Proceedings Eleventh IEEE International Symposium on Wearable Computers, ISWC, pp. 29-36, 2007.
Mendez et al., "Interactions Between Sleep and Epilepsy," Journal of Clinical Neurophysiology, American Clinical Neurophysiology Society, 18(2), pp. 106-127, 2001.
Paraschiv-Ionescu et al., "Ambulatory System for the Quantitative and Qualitative Analysis of Patients Treated with Spinal Cord Stimulation," Gait and Posture, vol. 20, Issue 2, pp. 113-125, Oct. 2004.
Slyper et al., "Action Capture with Accelerometers," Eurographics/ACM SIGGRAPH Symposium on Computer Animation, Carnegie Mellon University, 7 pp. 2008.
Smith et al., "How do sleep disturbance and chronic pain inter-relate? Insights from the longitudinal and cognitive-behavioral clinical trials literature," Sleep Medicine Reviews, YSMRV 286, pp. 1-14, 2003.
Smith et al., "Presleep cognitions in Patients with Insomnia Secondary to Chronic Pain," Journal of Behavioral Medicine, vol. 24, No. 1, pp. 93-114, 2001.
Emmanuel Munguia Tapia, "Activity Recognition from Accelerometer Data for Videogame Applications," http://alumni.media.mit.edu/~emunguia/html/videogames.htm, 7 pp., Dec. 2, 2003, printed Oct. 1, 2009.
Trolier-Mckinstry et al., "Thin Film Piezoelectrics for MEMS," Journal of Electroceramics, v. 12, No. 1-2, pp. 7-17, Jan./Mar. 2004.
Tuck, "Implementing Auto-Zero Calibration Technique for Accelerometers," Freescale Semiconductor Application Note AN3447, 5 pp., Mar. 2007.
Tuisku, "Motor Activity Measured by Actometry in Neuropsychiatric Disorders," Department of Psychiatry, University of Helsinki, Helsinki, Finland, 115 pp., 2002.
Vega-Gonzalez, "Upper Limb Activity Monitoring," Arch Phys Med Rehabil, vol. 86, pp. 541-548, Mar. 2005.
Velten et al., "A New Three-Axis Accelerometer," Sensor '99—$9^{th}$ Int'l Traide Fair and Conference for Sensors/Transducers & Systems, Nürnberg, Germany, May 18-20, 1999, Sensor '99 Proceedings II, A 5.2, pp. 47-52, 1999.
PCT/US09/48282: International Search Report and Written Opinion dated Sep. 3, 2009, 16 pp.
U.S. Appl. No. 12/815,834, filed Jun. 15, 2010, Gerber et al.
U.S. Appl. No. 12/433,856, filed Apr. 30, 2009, Skelton et al.
U.S. Appl. No. 12/433,750, filed Apr. 30, 2009, Skelton et al.
U.S. Appl. No. 12/433,103, filed Apr. 30, 2009, Skelton et al.
U.S. Appl. No. 12/433,632, filed Apr. 30, 2009, Skelton et al.
U.S. Appl. No. 12/433,558, filed Apr. 30, 2009, Skelton et al.
U.S. Appl. No. 12/433,623, filed Apr. 30, 2009, Skelton et al.
U.S. Appl. No. 12/433,854, filed Apr. 30, 2009, Skelton et al.
U.S. Appl. No. 12/433,749, filed Apr. 30, 2009, Skelton et al.
U.S. Appl. No. 12/433,855, filed Apr. 30, 2009, Skelton et al.
U.S. Appl. No. 12/433,501, filed Apr. 30, 2009, Skelton et al.
U.S. Appl. No. 12/433,520, filed Apr. 30, 2009, Skelton.
U.S. Appl. No. 12/433,551, filed Apr. 30, 2009, Davis et al.
U.S. Appl. No. 12/433,588, filed Apr. 30, 2009, Skelton et al.
U.S. Appl. No. 12/433,599, filed Apr. 30, 2009, Skelton et al.
U.S. Appl. No. 12/433,442, filed Apr. 30, 2009, Skelton et al.
U.S. Appl. No. 12/433,756, filed Apr. 30, 2009, Panken et al.
U.S. Appl. No. 12/433,808, filed Apr. 30, 2009, Skelton et al.
U.S. Appl. No. 12/433,725, filed Apr. 30, 2009, Skelton et al.
U.S. Appl. No. 12/433,530, filed Apr. 30, 2009, Skelton et al.
U.S. Appl. No. 12/433,373, filed Apr. 30, 2009, Skelton et al.
U.S. Appl. No. 12/433,651, filed Apr. 30, 2009, Skelton et al.
U.S. Appl. No. 12/433,673, filed Apr. 30, 2009, Skelton et al.
U.S. Appl. No. 12/433,785, filed Apr. 30, 2009, Davis et al.
U.S. Appl. No. 12/433,827, filed Apr. 30, 2009, Skelton et al.
U.S. Appl. No. 12/433,848, filed Apr. 30, 2009, Skelton et al.
U.S. Appl. No. 12/433,840, filed Apr. 30, 2009, Skelton et al.
U.S. Appl. No. 12/433,839, filed Apr. 30, 2009, Skelton et al.
U.S. Appl. No. 12/433,803, filed Apr. 30, 2009, Skelton et al.
U.S. Appl. No. 12/433,815, filed Apr. 30, 2009, Skelton et al.
U.S. Appl. No. 12/433,684, filed Apr. 30, 2009, Skelton et al.
U.S. Appl. No. 12/771,854, filed Apr. 30, 2010, Skelton.
U.S. Appl. No. 12/433,017, filed Apr. 30, 2009, Skelton et al.
U.S. Appl. No. 12/433,004, filed Apr. 30, 2009, Panken et al.
U.S. Appl. No. 12/548,227, filed Aug. 26, 2009, Skelton et al.
U.S. Appl. No. 12/433,038, filed Apr. 30, 2009, Panken.
U.S. Appl. No. 12/433,029, filed Apr. 30, 2009, Panken et al.
U.S. Appl. No. 12/432,993, filed Apr. 30, 2010, Panken et al.
U.S. Appl. No. 12/769,461, filed Apr. 28, 2010, Sahasrabudhe et al.
U.S. Appl. No. 12/769,391, filed Apr. 28, 2010, Sahasrabudhe et al.
U.S. Appl. No. 12/769,484, filed Apr. 28, 2010, Panken et al.
Office Action dated Mar. 5, 2012 for U.S. Appl. No. 12/433,558, (8 pgs.).
Responsive Amendment dated Jun. 5, 2012 for U.S. Appl. No. 12/433,558, (12 pgs.).

* cited by examiner

PATIENT INTERACTION WITH POSTURE-RESPONSIVE THERAPY

This application claims the benefit of U.S. Provisional Application No. 61/080,009, entitled, "PATIENT INTERACTION WITH POSTURE-RESPONSIVE THERAPY," and filed on Jul. 11, 2008, the entire content of which is incorporated herein by reference.

TECHNICAL FIELD

The disclosure relates to medical devices and, more particularly, to programmable medical devices that deliver therapy.

BACKGROUND

A variety of medical devices are used for chronic, e.g., long-term, delivery of therapy to patients suffering from a variety of conditions, such as chronic pain, tremor, Parkinson's disease, epilepsy, urinary or fecal incontinence, sexual dysfunction, obesity, or gastroparesis. As examples, electrical stimulation generators are used for chronic delivery of electrical stimulation therapies such as cardiac pacing, neurostimulation, muscle stimulation, or the like. Pumps or other fluid delivery devices may be used for chronic delivery of therapeutic agents, such as drugs. Typically, such devices provide therapy continuously or periodically according to parameters contained within a program. A program may comprise respective values for each of a plurality of parameters, specified by a clinician.

In some cases, the patient may be allowed to activate and/or modify the therapy delivered by the medical device. For example, a patient can be provided with a patient programming device. The patient programming device communicates with a medical device to allow the patient to activate therapy and/or adjust therapy parameters. For example, an implantable medical device (IMD), such as an implantable neurostimulator, may be accompanied by an external patient programmer that permits the patient to activate and deactivate neurostimulation therapy and/or adjust the intensity of the delivered neurostimulation. The patient programmer may communicate with the IMD via wireless telemetry to control the IMD and/or retrieve information from the IMD.

SUMMARY

In general, the disclosure relates to the delivery of therapy to a patient according to a detected posture state of the patient. The disclosure contemplates a variety of techniques for managing therapy delivered to a patent, including user interaction with a medical device that is configured to deliver therapy according to a posture state of a patient. User interaction may include interaction by a patient, clinician, or other person. The therapy management techniques described in this disclosure are applicable to electrical stimulation therapy or other therapies, such as therapeutic agent delivery therapy. User interaction with the medical device may be accomplished via an external device, such as a patient programmer or clinician programmer.

In some examples, a patient may be permitted to selectively turn posture-responsive therapy on and off for selected groups or programs, or on a global basis. In this case, the patient may revert to manual adjustment of therapy parameters without automated or semi-automated adjustments provided by posture-responsive therapy. In some examples, the medical device may deliver non-posture-responsive therapy to the patient during the time period that the patient has turned off posture-responsive therapy. In addition, a user interface may present to a user whether posture-responsive therapy is enabled or disabled for individual therapy programs or groups.

As an additional feature, after the patient has turned off posture-responsive therapy, a clinician may be permitted to selectively reactivate posture-responsive therapy via a local or remote command from a clinician programmer or other device. In some cases, reactivation may occur automatically upon expiration of a timer.

As another feature, a medical device may be configure to automatically or semi-automatically adjust one or more aspect of posture responsive therapy based at least in part on time or the posture state behavior. In particular, a medical device may automatically suspend one or more aspects of posture-responsive therapy and/or reduce the frequency at which patient posture state is detected based on time and/or the posture state behavior of the patient.

As another feature, a patient may be able to temporarily override delivery of a first stimulation therapy that is associated with a particular posture state of the patient such that a second stimulation therapy is delivered by the medical device to the patient instead. The second stimulation therapy may be associated with another posture state of the patient. The temporary override may be terminated by the medical device upon detection of an override termination action, e.g., the expiration of a time period and/or detection of a patient posture state transition.

In one example, the disclosure relates to a method comprising receiving an indication from a user indicating that at least one aspect of therapy delivered to a patient from a medical device should be suspended, wherein the at least one aspect of the therapy is delivered from the medical device to the patient according to a detected posture state of the patient; and suspending the at least one aspect of the therapy in response to receipt of the indication.

In another example, the disclosure relates to a medical device comprising a processor configured to receive an indication from a user indicating that at least one aspect of therapy delivered to a patient from the medical device should be suspended, and suspend the at least one aspect of the therapy in response to the receipt of the indication, wherein the at least one aspect of the therapy is delivered from the medical device to the patient according to a detected posture state of the patient In another example, the disclosure relates to a system comprising means for receiving an indication from a user indicating that at least one aspect of therapy delivered to a patient from a medical device should be suspended, wherein the at least one aspect of the therapy is delivered from the medical device to the patient according to a detected posture state of the patient; and means for suspending the at least one aspect of the therapy in response to receipt of the indication.

In another example, the disclosure relates to a computer-readable storage medium comprising instructions for causing one or more processors to receive an indication from a user via an external device indicating that at least one aspect of therapy delivered to a patient from a medical device should be suspended, wherein the at least one aspect of the therapy is delivered from the medical device to the patient according to a detected posture state of the patient; and suspend the at least one aspect of the therapy in response to receipt of the indication.

In another example, the disclosure relates to a method comprising receiving an input from a user indicating that at least one aspect of stimulation therapy that is delivered by a medical device according to a detected posture state of a patient should be suspended; generating an indication indicating that the at least one aspect of stimulation therapy that is delivered according to the detected posture state of the patient should be suspended based on the receipt of the input from the user; and sending the indication to the medical device that delivers the stimulation therapy to the patient according to the detected posture of the patient.

In another example, the disclosure relates to a device comprising a user interface configured to receive an input from a user indicating that at least one aspect of stimulation therapy that is delivered by a medical device according to a detected posture state of a patient should be suspended; and a processor configured to generate an indication indicating that the at least one aspect of stimulation therapy that is delivered according to the detected posture state of the patient should be suspended based on the receipt of the input from the user, and send the indication to the medical device that delivers the stimulation therapy to the patient according to the detected posture of the patient.

In another example, the disclosure relates to a system comprising means for receiving an input from a user indicating that at least one aspect of stimulation therapy that is delivered by a medical device according to a detected posture state of a patient should be suspended; means for generating an indication indicating that the at least one aspect of stimulation therapy that is delivered according to the detected posture state of the patient should be suspended based on the receipt of the input from the user; and means for sending the indication to the medical device that delivers the stimulation therapy to the patient according to the detected posture of the patient.

In another example, the disclosure relates to a computer-readable storage medium comprising instructions for causing one or more processors to receive an input from a user indicating that at least one aspect of stimulation therapy that is delivered to a patient by a medical device according to a detected posture state of a patient should be suspended; generate an indication indicating that the at least one aspect of stimulation therapy that is delivered according to the detected posture state of the patient should be suspended based on the receipt of the input from the user; and send the indication to a medical device that delivers the stimulation therapy to the patient according to the detected posture of the patient.

In another example, the disclosure relates to a method comprising obtaining an operational status of a therapy group from a medical device, wherein the medical device is configured to deliver therapy to a patient according to a detected posture state of the patient; and presenting the operational status of the therapy group via an external device, wherein presenting the operational status of the therapy group comprises presenting whether the therapy group is active for delivery of therapy.

In another example, the disclosure relates to an external device comprising a processor configured to obtain an operational status of a therapy group from a medical device, the medical device configured to deliver therapy to a patient according to a detected posture state of the patient; and a user interface configured to present the operational status of the therapy group, wherein the operational status of the therapy group comprises whether the therapy group is active for delivery of therapy via the medical device.

In another example, the disclosure relates to a system comprising a medical device configured to detect the posture state of a patient and deliver therapy according to the detected posture state; and an external device comprising a processor and a user interface, wherein the processor is configured to obtain an operational status of a therapy group from a medical device, and the user interface is configured to present the operational status of the therapy group, wherein the operational status of the therapy group comprises whether the therapy group is active for delivery of therapy from the medical device.

In another example, the disclosure relates to a system comprising means for obtaining an operational status of a therapy group from a medical device, the medical device configured to deliver therapy to a patient according to the detected posture state of the patient; and means for presenting the operational status of the therapy group, wherein the operational status of the therapy group comprises whether the therapy group is active for delivery of therapy from the medical device.

In another example, the disclosure relates to a computer-readable storage medium comprising instructions for causing one or more processors to obtain an operational status of a therapy group from a medical device, wherein the medical device is configured to deliver therapy to a patient according to the detected posture state of the patient; and present the operational status of the therapy group via an external device, wherein the operational status of the therapy group comprises whether the therapy group is active for delivery of therapy from the medical device.

In another example, the disclosure relates to a method comprising receiving an indication from an external device to resume delivery of therapy to a patient that was previously turned off, wherein the therapy that was previously turned off comprises therapy delivered to the patient according to a detected posture state of the patient; obtaining therapy information defining the therapy; and resuming the delivery of therapy to the patient in response to the receipt of the indication, wherein the delivery of therapy is resumed according to the obtained therapy information.

In another example, the disclosure relates to a system comprising a therapy module configured to deliver therapy to a patient according to a detected posture state of a patient; and a processor configured to receive an indication from an external device to resume delivery of therapy to a patient that was previously turned off, obtain therapy information defining the therapy, and resume delivery of therapy to the patient via the therapy module in response to the receipt of the indication, wherein the delivery of therapy is resumed according to the obtained therapy information, wherein the therapy that was previously turned off comprises therapy delivered to the patient according to the detected posture state of the patient.

In another example, the disclosure relates to a system comprising means for receiving an indication from an external device to resume delivery of therapy to a patient that was previously turned off, wherein the therapy that was previously turned off comprises therapy delivered to the patient according to a detected posture state of the patient; means for obtaining therapy information defining the therapy; and means for resuming the delivery of therapy to the patient in response to the receipt of the indication, wherein the delivery of therapy is resumed according to the obtained therapy information.

In another example, the disclosure relates to a computer-readable storage medium comprising instructions for causing one or more processors to receive an indication from an external device to resume delivery of therapy to a patient that was previously turned off, wherein the therapy that was previously turned off comprises therapy delivered to the patient according to a detected posture state of the patient; obtain therapy information defining the therapy; and resume the delivery of therapy to the patient in response to the receipt of the indication, wherein the delivery of therapy is resumed according to the obtained therapy information.

In another example, the disclosure relates to a method comprising delivering a first therapy to a patient via a medical device, the first therapy associated with a first posture state of the patient; receiving an indication from a user indicating that a second therapy should be delivered, the second therapy associated with a second posture state of the patient; and delivering the second therapy to the patient instead of the first therapy based on the indication.

In another example, the disclosure relates to a system comprising a therapy delivery module configured to deliver therapy to a patient; and a processor configured to control the therapy module to deliver a first therapy to the patient, receive an indication from a user indicating that a second therapy should be delivered, and control the therapy module to deliver the second therapy to the patient instead of the first therapy based on the indication, wherein the first therapy is associated with a first posture state of the patient, and the second therapy is associated with a second posture state of the patient.

In another example, the disclosure relates to a system comprising means for delivering a first therapy to a patient via a medical device, the first therapy associated with a first posture state of the patient; means for receiving an indication from a user indicating that a second therapy should be delivered, the second therapy associated with a second posture state of the patient; and means for delivering the second therapy to the patient instead of the first therapy based on the indication.

In another example, the disclosure relates to a computer-readable storage medium comprising instructions for causing one or more processors to deliver a first therapy to a patient via a medical device, the first therapy associated with a first posture state of the patient; receive an indication from a user indicating that a second therapy should be delivered, the second therapy associated with a second posture state of the patient; and deliver the second therapy to the patient instead of the first therapy based on the indication.

In another example, the disclosure relates to a method comprising delivering therapy to a patient from a medical device, wherein the therapy is delivered to the patient according to a detected posture state of the patient; and automatically adjusting at least one aspect of the therapy delivered from a medical device based at least in part on one or more of time or patient posture state behavior, wherein automatically adjusting at least one aspect of therapy comprises suspending at least one aspect of the therapy or decreasing a posture state detection frequency.

In another example, the disclosure relates to a system comprising a therapy delivery module configured to deliver therapy to a patient; a timing unit configured to determine time; and a processor configured to control the therapy module to deliver therapy to the patient according to a detected posture state of the patient, and automatically adjust at least one aspect of the therapy delivered from a medical device based at least in part on one or more of time or patient posture state behavior, wherein the processor at least one of suspends at least one aspect of the therapy or decreases a posture state detection frequency to automatically adjust the at least one aspect of the therapy.

In another example, the disclosure relates to a system comprising A system comprising means for delivering therapy to a patient from a medical device, wherein the therapy is delivered to the patient according to a detected posture state of the patient; and means for automatically adjusting at least one aspect of the therapy delivered from a medical device based at least in part on one or more of time or patient posture state behavior, wherein automatically adjusting at least one aspect of therapy comprises suspending at least one aspect of the therapy or decreasing a posture state detection frequency.

In another example, the disclosure relates to a computer-readable storage medium comprising instructions for causing one or more processors to deliver therapy to a patient from a medical device, wherein the therapy is delivered to the patient according to a detected posture state of the patient; and automatically adjust at least one aspect of the therapy delivered from a medical device based at least in part on one or more of time or patient posture state behavior, wherein the instructions may cause the one or more processor to suspend the at least one aspect of the therapy or decrease a posture state detection frequency to automatically adjust at least one aspect of the therapy.

The details of one or more examples of systems, devices, and techniques are set forth in the accompanying drawings and the description below. Other features, objects, and advantages of the disclosure will be apparent from the description and drawings, and from the claims.

DETAILED DESCRIPTION

Figure 1A:
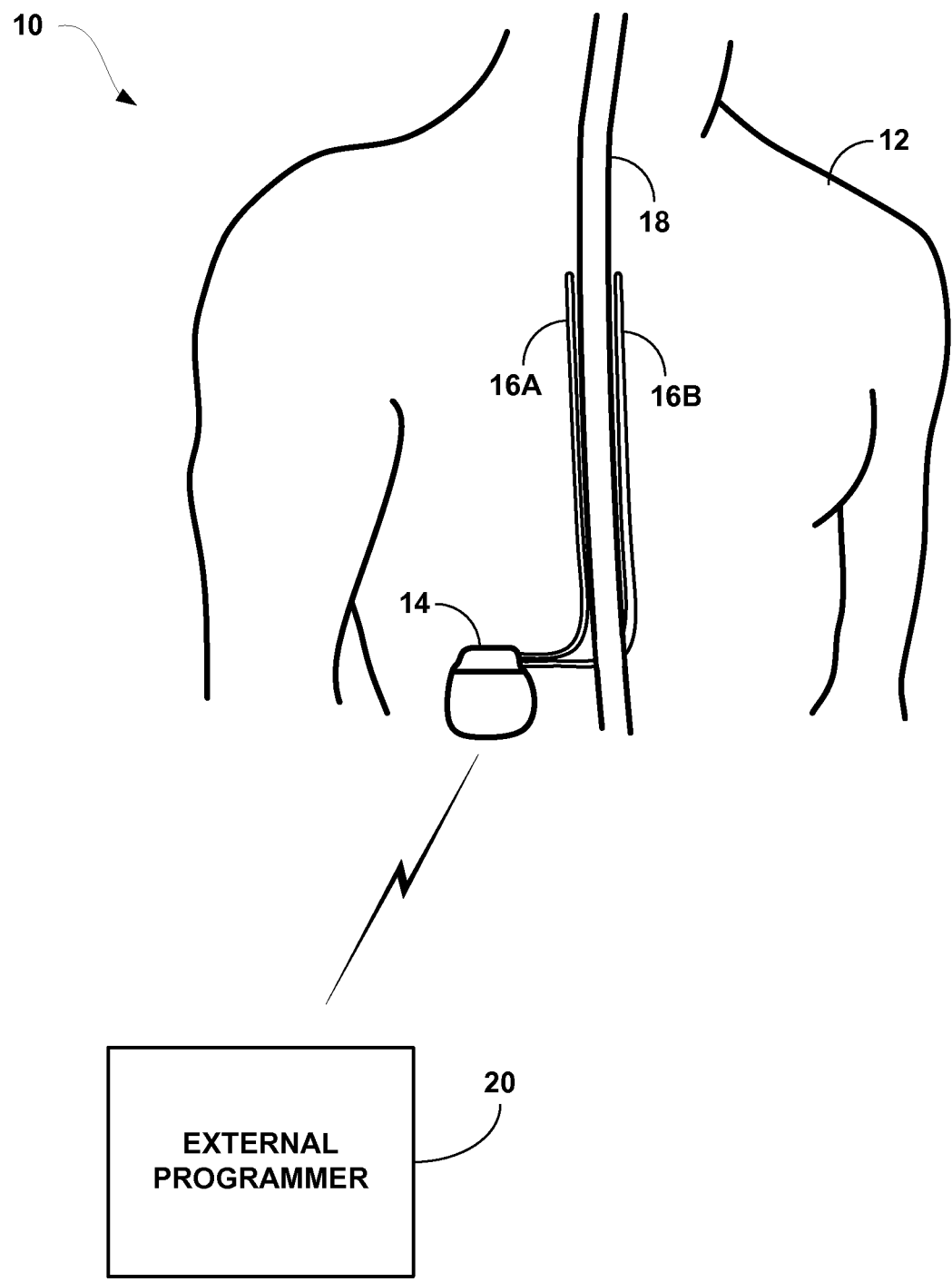
FIG. 1A is a conceptual diagram illustrating an example implantable stimulation system including two implantable stimulation leads.

In some medical devices that deliver electrical stimulation therapy, therapeutic efficacy may change as a patient changes posture states. In general, a posture state may refer to a patient posture or a combination of posture and patient activity. For example, some posture states, such as upright, may be subcategorized as upright and active or upright and inactive. Other posture states, such as lying down posture states, may or may not have an patient activity component. Efficacy may refer, in general, to a combination of complete or partial alleviation of symptoms alone, or in combination with a degree of undesirable side effects.

Changes in posture state may cause changes in efficacy due to changes in distances between electrodes or other therapy delivery elements, e.g., due to temporary migration of leads or catheters caused by forces or stresses associated with different postures, or from changes in compression of patient tissue in different posture states. Also, posture state changes may present changes in symptoms or symptom levels, e.g., pain level. To maintain therapeutic efficacy, it may be desirable to adjust the value of one or more therapy parameters according to the posture state of the patient to maintain effective therapy. A therapy system may adjust therapy by modifying values for one or more therapy parameters, e.g., by specifying adjustments to a specific therapy parameter or by selecting different therapy programs or groups of programs that define different sets of therapy parameter values.

A change in efficacy of the therapy due to changes in posture state of the patient may require the patient to continually manage therapy by manually adjusting certain therapy parameters values, such as amplitude, pulse rate, or pulse width, or selecting different therapy programs to achieve more efficacious therapy throughout many different posture states of the patient. In some cases, a medical device employs a posture state module that detects the patient posture state. The medical device adjusts therapy parameters in response to different posture states, which are determined with the posture state module. Therapy adjustments in response to different posture states may be fully automatic, semi-automatic in the sense that a user may provide approval of proposed changes, or user-directed in the sense that the patient may manually adjust therapy based on the posture state indication.

In general, the disclosure relates to the delivery of therapy to a patient according to a detected posture state of the patient. The disclosure contemplates a variety of techniques for managing therapy delivered to a patent, including user interaction, e.g., patient and/or clinician interaction, with a medical device that is configured to deliver therapy according to posture state of a patient. The techniques are applicable to electrical stimulation therapy or other therapies, such as therapeutic agent delivery therapy. User interaction with the medical device may be accomplished via an external device, such as a patient programmer or clinician programmer.

In some example, a patient may be permitted to selectively turn posture-responsive therapy on and off for selected groups or programs, or on a global basis. In this case, the patient may revert to manual adjustment of therapy parameters without automated or semi-automated adjustments provided by posture-responsive therapy. In some examples, the medical device may deliver non-posture-responsive therapy to the patient during the time period that the patient has turned off posture-responsive therapy. In addition, a user interface may present to a user whether posture-responsive therapy is enabled or disabled for individual therapy programs or groups.

As an additional feature, after the patient has turned off posture-responsive therapy, a clinician may be permitted to selectively reactivate posture-responsive therapy via a local or remote command from a clinician programmer or other device. In some cases, reactivation may occur automatically upon expiration of a timer.

As another feature, a patient may be able to temporarily override delivery of a first stimulation therapy that is associated with a particular posture state of the patient such that a second stimulation therapy is delivered by the medical device to the patient instead. The second stimulation therapy may be associated with another posture state of the patient. The temporary override may be terminated by the medical device upon detection of an override termination action, e.g., the expiration of a time period and/or detection of a patient posture state transition.

FIG. 1A is a schematic diagram illustrating an implantable stimulation system 10 including a pair of implantable electrode arrays in the form of stimulation leads 16A and 16B. Although the techniques described in this disclosure are generally applicable to a variety of medical devices including external and implantable medical devices (IMDs), application of such techniques to IMDs and, more particularly, implantable electrical stimulators such as neurostimulators will be described for purposes of illustration. More particularly, the disclosure will refer to an implantable SCS system for purposes of illustration, but without limitation as to other types of medical devices.

As shown in FIG. 1A, system 10 includes an IMD 14 and external programmer 20 shown in conjunction with a patient 12, who is ordinarily a human patient. In the example of FIG. 1A, IMD 14 is an implantable electrical stimulator that delivers SCS, e.g., for relief of chronic pain or other symptoms. Again, although FIG. 1A shows an IMD, other examples may include an external stimulator, e.g., with percutaneously implanted leads. Stimulation energy is delivered from IMD 14 to spinal cord 18 of patient 12 via one or more electrodes of implantable leads 16A and 16B (collectively "leads 16"). In some applications, such as spinal cord stimulation (SCS) to treat chronic pain, the adjacent implantable leads 16 may have longitudinal axes that are substantially parallel to one another.

Although FIG. 1A is directed to SCS therapy, system 10 may alternatively be directed to any other condition that may benefit from stimulation therapy. For example, system 10 may be used to treat tremor, Parkinson's disease, epilepsy, urinary or fecal incontinence, sexual dysfunction, obesity, gastroparesis, or psychiatric disorders (e.g., depression, mania, obsessive compulsive disorder, anxiety disorders, and the like). In this manner, system 10 may be configured to provide therapy taking the form of deep brain stimulation (DBS), pelvic floor stimulation, gastric stimulation, or any other stimulation therapy.

Each of leads 16 may include electrodes (not shown in FIG. 1), and the parameters for a program that controls delivery of stimulation therapy by IMD 14 may include information identifying which electrodes have been selected for delivery of stimulation according to a stimulation program, the polarities of the selected electrodes, i.e., the electrode configuration for the program, and voltage or current amplitude, pulse rate, and pulse width of stimulation delivered by the electrodes. Delivery of stimulation pulses will be described for purposes of illustration. However, stimulation may be delivered in other forms, such as continuous waveforms. Programs that control delivery of other therapies by IMD 12 may include other parameters, e.g., such as dosage amount, rate, or the like for drug delivery.

In the example of FIG. 1A, leads 16 carry one or more electrodes that are placed adjacent to the target tissue of the spinal cord. One or more electrodes may be disposed at a distal tip of a lead 16 and/or at other positions at intermediate points along the lead. Electrodes of leads 16 transfer electrical stimulation generated by IMD 14 to tissue of patient 12. The electrodes may be electrode pads on a paddle lead, circular (e.g., ring) electrodes surrounding the body of leads 16, conformable electrodes, cuff electrodes, segmented electrodes, or any other type of electrodes capable of forming unipolar, bipolar or multipolar electrode configurations for therapy. In general, ring electrodes arranged at different axial positions at the distal ends of leads 16 will be described for purposes of illustration.

Leads 16 may be implanted within patient 12 and directly or indirectly (e.g., via a lead extension) coupled to IMD 14. Alternatively, as mentioned above, leads 16 may be implanted and coupled to an external stimulator, e.g., through a percutaneous port. In some cases, an external stimulator is a trial or screening stimulation that used on a temporary basis to evaluate potential efficacy to aid in consideration of chronic implantation for a patient. In additional examples, IMD 14 may be a leadless stimulator with one or more arrays of electrodes arranged on a housing of the stimulator rather than leads that extend from the housing.

IMD 14 delivers electrical stimulation therapy to patient 12 via selected combinations of electrodes carried by one or both of leads 16. The target tissue for the electrical stimulation therapy may be any tissue affected by electrical stimulation energy, which may be in the form of electrical stimulation pulses or waveforms. In some examples, the target tissue includes nerves, smooth muscle, and skeletal muscle. In the example illustrated by FIG. 1A, the target tissue is tissue proximate spinal cord 18, such as within an intrathecal space or epidural space of spinal cord 18, or, in some examples, adjacent nerves that branch off of spinal cord 18. Leads 16 may be introduced into spinal cord 18 in via any suitable region, such as the thoracic, cervical or lumbar regions. Stimulation of spinal cord 18 may, for example, prevent pain signals from traveling through the spinal cord and to the brain of the patient. Patient 12 may perceive the interruption of pain signals as a reduction in pain and, therefore, efficacious therapy results.

The deployment of electrodes via leads 16 is described for purposes of illustration, but arrays of electrodes may be deployed in different ways. For example, a housing associated with a leadless stimulator may carry arrays of electrodes, e.g., rows and/or columns (or other patterns) Such electrodes may be arranged as surface electrodes, ring electrodes, or protrusions. As a further alternative, electrode arrays may be formed by rows and/or columns of electrodes on one or more paddle leads. In some examples, electrode arrays may include electrode segments, which may be arranged at respective positions around a periphery of a lead, e.g., arranged in the form of one or more segmented rings around a circumference of a cylindrical lead.

In the example of FIG. 1A, stimulation energy is delivered by IMD 14 to the spinal cord 18 to reduce the amount of pain perceived by patient 12. As described above, IMD 14 may be used with a variety of different therapies, such as peripheral nerve stimulation (PNS), peripheral nerve field stimulation (PNFS), DBS, cortical stimulation (CS), pelvic floor stimulation, gastric stimulation, and the like. The electrical stimulation delivered by IMD 14 may take the form of electrical stimulation pulses or continuous stimulation waveforms, and may be characterized by controlled voltage levels or controlled current levels, as well as pulse width and pulse rate in the case of stimulation pulses.

In exemplary examples, IMD 14 generates and delivers stimulation therapy according to one or more programs. A program defines values for one or more parameters that define an aspect of the therapy delivered by IMD 14 according to that program. For example, a program that controls delivery of stimulation by IMD 14 in the form of pulses may define a voltage or current pulse amplitude, a pulse width, a pulse rate, for stimulation pulses delivered by IMD 14 according to that program. Moreover, therapy may be delivered according to multiple programs, wherein multiple programs are contained within each of a plurality of groups.

Each program group may support an alternative therapy selectable by patient 12, and IMD 14 may deliver therapy according to the multiple programs. IMD 14 may rotate through the multiple programs of the group when delivering stimulation such that numerous conditions of patient 12 are treated. As an illustration, in some cases, stimulation pulses formulated according to parameters defined by different programs may be delivered on a time-interleaved basis. For example, a group may include a program directed to leg pain, a program directed to lower back pain, and a program directed to abdomen pain. In this manner, IMD 14 may treat different symptoms substantially simultaneously.

During use of IMD 14 to treat patient 12, movement of patient 12 among different posture states may affect the ability of IMD 14 to deliver consistent efficacious therapy. For example, posture state changes may present changes in symptoms or symptom levels, e.g., pain level. As another example, a patient posture state may affect the relative location between the electrodes of leads 16 and a target therapy site. For example, leads 16 may migrate toward IMD 14 when patient 12 bends at the waist, resulting in displacement of electrodes relative to the target stimulation site and possible disruption in delivery of effective therapy. Stimulation energy transferred to target tissue may be reduced due to electrode migration, which may reduce therapeutic efficacy in terms of relief of symptoms (e.g., pain) or an increase in undesirable side effects.

As another example of how posture state may affect the relative location between the electrodes of leads 16 and a target therapy site, leads 16 may be compressed towards spinal cord 18 when patient 12 lies down. Such compression may cause an increase in the amount of stimulation energy transferred to the target tissue. An increase in stimulation energy transferred to the target stimulation site may cause unusual sensations or an otherwise undesirable intensity of therapy, which may both be considered undesirable side effects that undermine overall efficacy. Thus, in some examples, the amplitude of stimulation therapy may need to be decreased when patient 12 is lying down to avoid causing patient 12 additional pain or unusual sensations resulting from the increased compression near electrodes of leads 16. The additional pain or unusual sensations may be considered undesirable side effects that undermine overall efficacy.

Many other examples of reduced efficacy due to increase coupling or decreased coupling of stimulation energy to target tissue may occur due to changes in posture and/or activity level associated with patient posture state. To avoid or reduce possible disruptions in effective therapy due to posture state changes, IMD 14 includes a posture state module that detects the posture state of patient 12 and causes the IMD 14 to automatically adjust stimulation according to the detected posture state. For example, a posture state module may include a posture state sensor such as an accelerometer that detects when patient 12 lies down, stands up, or otherwise changes posture.

In response to a posture state indication by the posture state module, IMD 14 may modify the program group, program, stimulation amplitude value, pulse width, pulse rate, and/or one or more other parameters, groups or programs to maintain therapeutic efficacy. When a patient lies down, for example, IMD 14 may automatically reduce the stimulation amplitude value so that patient 12 does not need to reduce stimulation amplitude value manually. In some cases, IMD 14 may communicate with external programmer 20 to present a proposed change in stimulation in response to a posture state change, and receive approval or rejection of the change from a user, such as patient 12 or a clinician, before automatically applying the therapy change. In some examples, posture state detection may also be used to provide notifications, such as providing notification via a wireless link to a care giver that a patient has potentially experienced a fall.

In addition, in some examples, IMD 14 may include a timing unit, such as a clock or counter that monitors time. For example, timing unit may monitor the time of day that IMD 26 is delivering therapy. Based on the time of day, or any other suitable timing parameter, IMD 26 may suspend delivery of therapy or reduce the frequency at which the posture state of patient 12 is detected via the posture state module. Moreover, in some examples, the timing unit may be used to identify particular posture state behavior of patient 12, such as the amount of time between patient posture state transitions or amount of time that patient 12 has occupied a specific or general posture state. Based on the posture state behavior of patient 12, IMD 14 may also suspend delivery of therapy or reduce the frequency at which the posture state of patient 12 is detected via the posture state module.

Referring still to FIG. 1A, a user, such as a clinician or patient 12, may interact with a user interface of external programmer 20 to program IMD 14. Programming of IMD 14 may refer generally to the generation and transfer of commands, programs, or other information to control the operation of IMD 14. For example, external programmer 20 may transmit programs, parameter adjustments, program selections, group selections, or other information to control the operation of IMD 14, e.g., by wireless telemetry. As one example, external programmer 20 may transmit parameter adjustments to support therapy modifications relating to changes in the posture state of patient 12. As another example, a user may select programs or program groups. Again, a program may be characterized by an electrode combination, electrode polarities, voltage or current amplitude, pulse width, pulse rate, and/or duration. A group may be characterized by multiple programs that are delivered simultaneously or on an interleaved or rotating basis.

The user interface of external programmer 20 may indicate to the user the posture state in which the patient 12 currently resides, or at least the posture state of patient 12 that is detected by IMD 14. This patient posture state may be a static posture that does not take into account activity level, an activity level that does not take into account posture, or some combination of the posture and activity level that describes the physical position and movement of patient 12. As an example, posture may be characterized as one of the following postures: standing, sitting, lying down on back, lying down on front, lying down on left side, lying down on right side. Activity level may be characterized as one of: high, medium and low.

Posture state may indicate a combination of one of the above postures with one of the above activity levels. For some postures, such as lying down postures, the posture state may not need to consider activity level, as the patient may be less likely to undertake any significant activity in such postures. In other cases, all posture states may take into account posture and activity level, even if there is minimal activity in a particular posture. Posture state may be determined based on posture information and/or activity level information generated by a posture state module, which may include one or more accelerometers or other posture or activity level sensors.

The patient posture state may be represented by a posture state indication presented by the user interface of programmer 20 as a visible, audible, or tactile indication. When presented as a visible indication, the posture state indication may be, for example, a graphical representation, a symbolic icon, a textual representation such as word or number, an arrow, or any other type of indication. The visible indication may be presented via a display, such as an a liquid crystal display (LCD), dot matrix display, organic light-emitting diode (OLED) display, touch screen, or the like. In other cases, the visible indication may be provided in a translucent area that is selectively backlit to indicate a posture. An audible indication may be produced by programmer 20 as spoken words stating a posture state, or different audible tones, different numbers of tones, or other audible information generated by the programmer to indicate posture state. A tactile indication may be produced by programmer 20 different numbers of vibratory pulses delivered in sequence or vibratory pulses of different lengths, amplitudes, or frequencies.

Programmer 20 may present multiple indications representative of different patient posture states. IMD 14 may communicate a patient posture state according to a posture state parameter value sensed by a posture state module to external programmer 20, e.g., by wireless telemetry. For example, IMD 14 may transmit posture state indication to programmer 20 on a periodic, intermittent or continuous basis or in response to a posture state change. Alternatively, programmer 20 may request posture state indication from IMD 14 on a periodic, intermittent or continuous basis. External programmer 20 then may select and present the associated posture state indication.

In some cases, external programmer 20 may be characterized as a physician or clinician programmer if it is primarily intended for use by a physician or clinician. In other cases, external programmer 20 may be characterized as a patient programmer if it is primarily intended for use by a patient. A patient programmer is generally accessible to patient 12 and, in many cases, may be a portable device that may accompany the patient throughout the patient's daily routine. In general, a physician or clinician programmer may support selection and generation of programs by a clinician for use by IMD 14, whereas a patient programmer may support adjustment and selection of such programs by a patient during ordinary use.

IMD 14 may be constructed with a biocompatible housing, such as titanium or stainless steel, or a polymeric material such as silicone or polyurethane, and surgically implanted at a site in patient 12 near the pelvis. IMD 14 may also be implanted in patient 12 at a location minimally noticeable to patient 12. Alternatively, IMD 14 may be external with percutaneously implanted leads. For SCS, IMD 14 may be located in the lower abdomen, lower back, upper buttocks, or other location to secure IMD 14. Leads 16 may be tunneled from IMD 14 through tissue to reach the target tissue adjacent to spinal cord 18 for stimulation delivery.

Figure 1B:
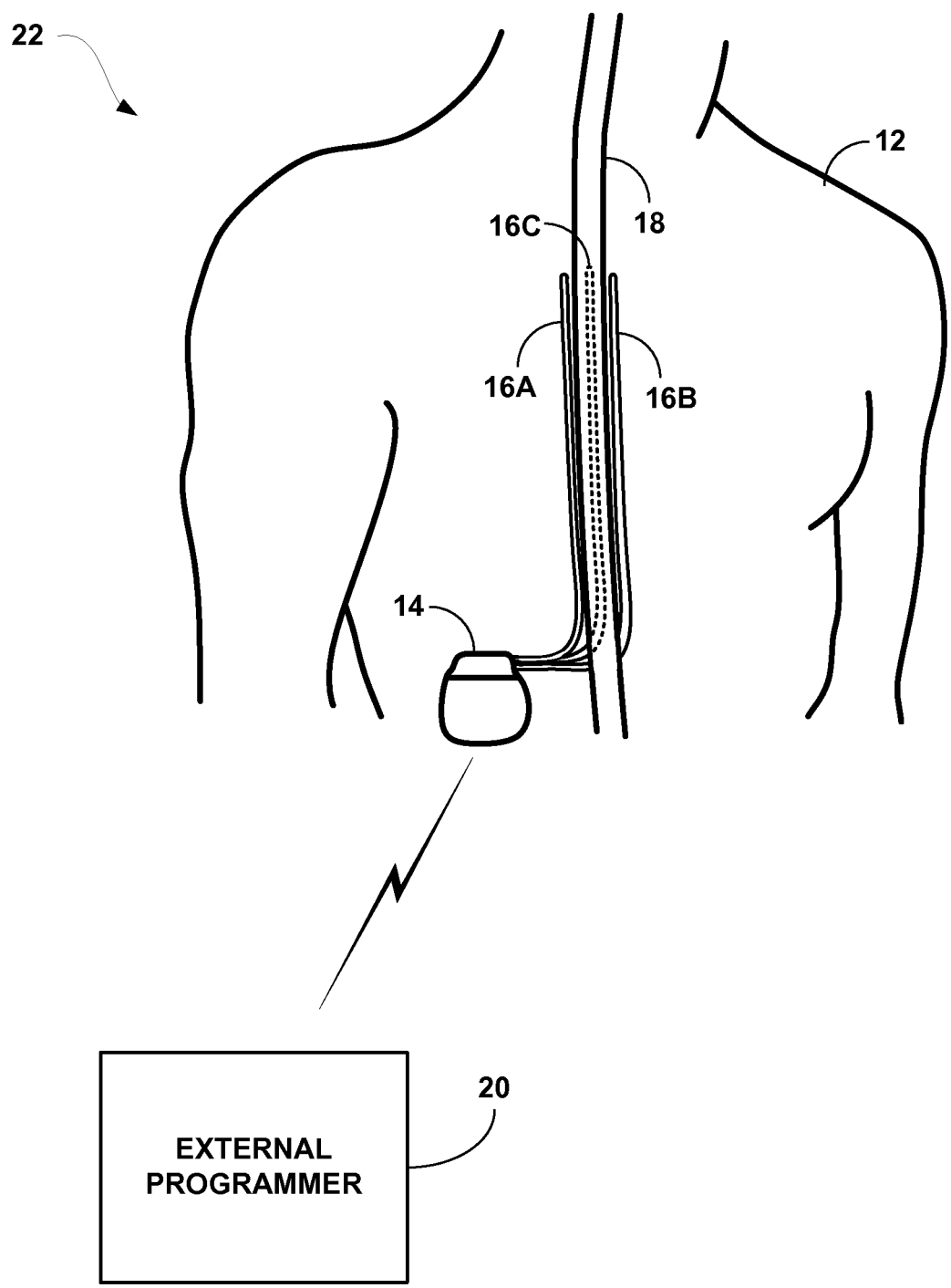
FIG. 1B is a conceptual diagram illustrating an example implantable stimulation system including three implantable stimulation leads.

FIG. 1B is a conceptual diagram illustrating an implantable stimulation system 22 including three implantable stimulation leads 16A, 16B, 16C (collectively leads 16). System 22 generally conforms to system 10 of FIG. 1A, but includes a third lead. Accordingly, IMD 14 may deliver stimulation via combinations of electrodes carried by all three leads 16, or a subset of the three leads. The third lead, e.g., lead 16C, may include a greater number of electrodes than leads 16A and 16B and be positioned between leads 16A and 16B or on one side of either lead 16A or 16B. The number and configuration of leads 16 may be stored within external programmer 20 to allow programmer 20 to appropriately program stimulation therapy or assist in the programming of stimulation therapy.

In some examples, leads 16A and 16B each include four electrodes, while lead 16C includes eight or sixteen electrodes, thereby forming a so-called 4-8-4 or 4-16-4 lead configuration. Other lead configurations, such as 8-16-8, 8-4-8, 16-8-16, 16-4-16, are possible, whereby the number in the configuration indication refers to the number of electrodes in a particular electrode column, which may be defined by a lead 16A-16C. In some cases, electrodes on lead 16C may be smaller in size and/or closer together than the electrodes of leads 16A or 16B. Movement of lead 16C due to changing activities or postures of patient 12 may, in some instances, more severely affect stimulation efficacy than movement of leads 16A or 16B. Patient 12 may further benefit from the ability of IMD 14 to detect posture states and associated changes and automatically adjust stimulation therapy to maintain therapy efficacy in a three lead system 22.

Figure 1C:
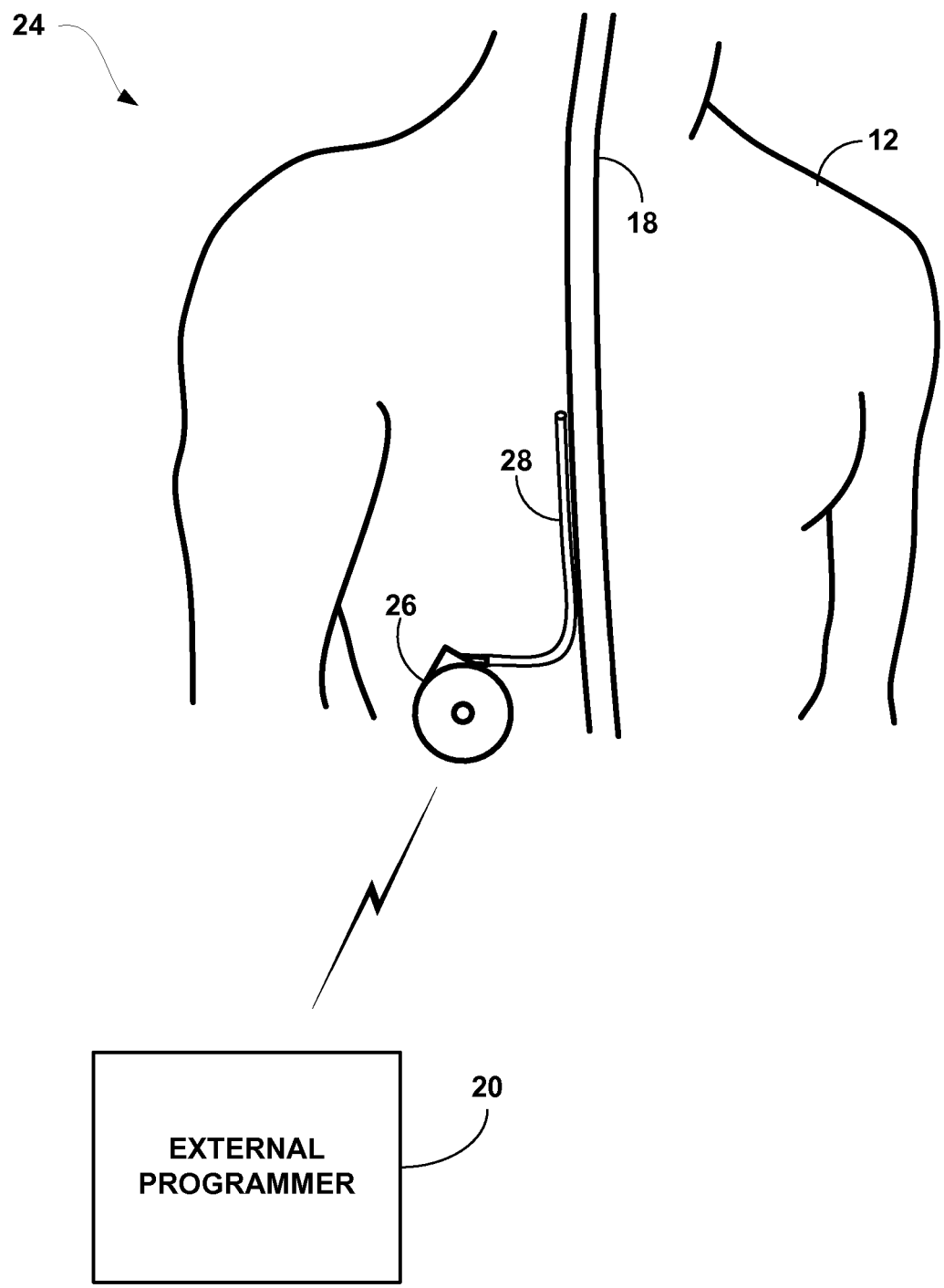
FIG. 1C is a conceptual diagram illustrating an example implantable drug delivery system including a delivery catheter.

FIG. 1C is a conceptual diagram illustrating an implantable drug delivery system 24 including one delivery catheter 28 coupled to IMD 26. As shown in the example of FIG. 1C, drug delivery system 24 is substantially similar to systems 10 and 22. However, drug delivery system 24 performs the similar therapy functions via delivery of one or more therapeutic agents instead of electrical stimulation therapy. IMD 26 functions as a drug pump in the example of FIG. 1C, and IMD 26 communicates with external programmer 20 to initialize therapy or modify therapy during operation. In addition, IMD 26 may be refillable to allow chronic drug delivery.

A fluid delivery port of catheter 28 may be positioned within an intrathecal space or epidural space of spinal cord 18, or, in some examples, adjacent nerves that branch off of spinal cord 18. Although IMD 26 is shown as coupled to only one catheter 28 positioned along spinal cord 18, additional catheters may also be coupled to IMD 26. Multiple catheters may deliver drugs or other therapeutic agents to the same anatomical location or the same tissue or organ. Alternatively, each catheter may deliver therapy to different tissues within patient 12 for the purpose of treating multiple symptoms or conditions. In some examples, IMD 26 may be an external device that includes a percutaneous catheter that to deliver a therapeutic agent to patient 12, e.g., in the same manner as catheter 28. Alternatively, the percutaneous catheter can be coupled to catheter 28, e.g., via a fluid coupler. In other examples, IMD 26 may include both electrical stimulation capabilities as described in IMD 14 (FIG. 1A) and drug delivery therapy.

IMD 26 may also operate using parameters that define the method of drug delivery. IMD 26 may include programs, or groups of programs, that define different delivery methods for patient 12. For example, a program that controls delivery of a drug or other therapeutic agent may include a titration rate or information controlling the timing of bolus deliveries. Patient 12 may use external programmer 20 to adjust the programs or groups of programs to regulate the therapy delivery.

Similar to IMD 14, IMD 26 includes a posture state module that monitors the patient posture state and adjusts therapy accordingly. For example, the posture state module may indicate that patient 12 transitions from lying down to standing up. IMD 26 may automatically increase the rate of drug delivered to patient 12 in the standing position if patient 12 has indicated that pain increased when standing. This automated adjustment to therapy based upon posture state may be activated for all or only a portion of the programs used by IMD 26 to deliver therapy. In addition, in some examples, IMD 26 may include a timing unit, such as a clock or counter that monitors time. For example, timing unit may monitor the time of day that IMD 26 is delivering therapy. Based on the time of day, or any other suitable timing parameter, IMD 26 may suspend delivery of therapy or reduce the frequency at which the posture state of patient 12 is detected via the posture state module. Moreover, in some examples, the timing unit may be used to identify particular posture state behavior of patient 12, such as the amount of time between patient posture state transitions or amount of time that patient 12 has occupied a specific or general posture state. Based on the posture state behavior of patient 12, IMD 14 may also suspend delivery of therapy or reduce the frequency at which the posture state of patient 12 is detected via the posture state module.

Figure 2:
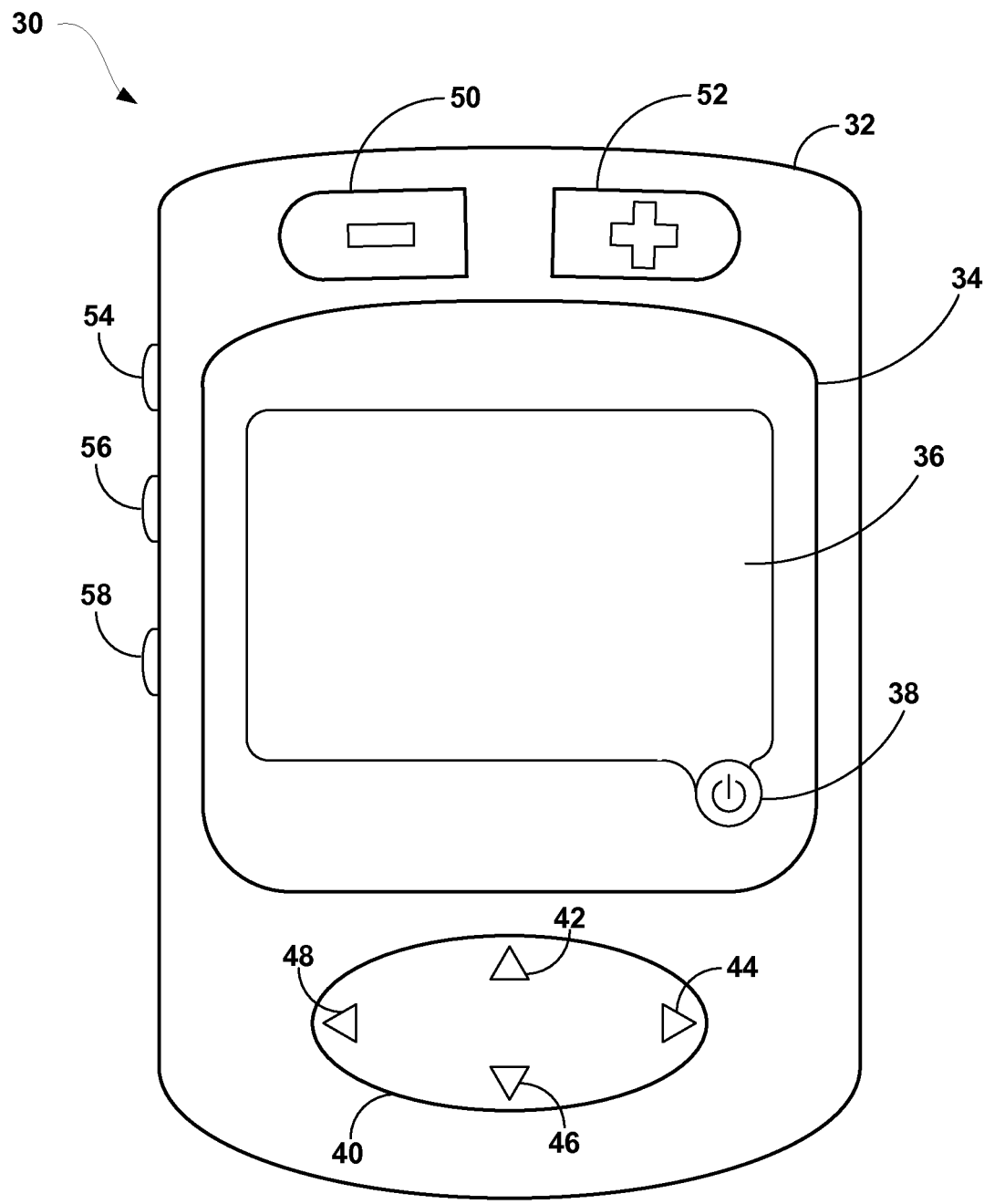
FIG. 2 is a conceptual diagram illustrating an example patient programmer for programming stimulation therapy delivered by an implantable medical device.

FIG. 2 is a conceptual diagram illustrating an example patient programmer 30 for programming stimulation therapy delivered by an IMD. Patient programmer 30 is an example of external programmer 20 illustrated in FIGS. 1A, 1B and 1C and may be used with either IMD 14 or IMD 26. In alternative examples, patient programmer 30 may be used with an external medical device. As shown in FIG. 2, patient programmer 30 provides a user interface (not shown) for a user, such as patient 12, to manage and program stimulation therapy. In addition, patient programmer 30 presents a posture state indication to patient 12 in order to represent the patient posture state. Patient programmer 30 is protected by housing 32, which encloses circuitry necessary for patient programmer 30 to operate.

Patient programmer 30 also includes display 36, power button 38, increase button 52, decrease button 50, sync button 58, stimulation ON button 54, and stimulation OFF button 56. Cover 34 protects display 36 from being damaged during use of patient programmer 30. Patient programmer 30 also includes control pad 40 which allows a user to navigate through items displayed on display 36 in the direction of arrows 42, 44, 46, and 48. In some examples, the buttons and pad 40 may take the form of soft keys (e.g., with functions and contexts indicated on display 36), with functionality that may change, for example, based on current programming operation or user preference. In alternative examples, display 36 is a touch screen with which patient 12 may directly interact without the use of control pad 40. A touch screen display may eliminate the use of buttons, such as increase button 52 and decrease button 50, although buttons may be used in addition to a touch screen display.

In the illustrated example, patient programmer 30 is a hand held device. Patient programmer 30 may accompany patient 12 throughout a daily routine. In some cases, patient programmer 30 may be used by a clinician when patient 12 visits the clinician in a hospital or clinic. In other examples, patient programmer 30 may be a clinician programmer that remains with the clinician or in the clinic and is used by the clinician and/or patient 12 when the patient is in the clinic. In the case of a clinician programmer, small size and portability may be less important. Accordingly, a clinician programmer may be sized larger than a patient programmer, and it may provide a larger screen for more full-featured programming.

Housing 32 may be constructed of a polymer, metal alloy, composite, or combination material suitable to protect and contain components of patient programmer 30. In addition, housing 32 may be partially or completely sealed such that fluids, gases, or other elements may not penetrate the housing and affect components therein. Power button 38 may turn patient programmer 30 ON or OFF as desired by patient 12. Patient 12 may control the illumination level, or backlight level, of display 36 by using control pad 40 to navigate through the user interface and increase or decrease the illumination level with decrease and increase buttons 50 and 52.

In some examples, illumination may be controlled by a knob that rotates clockwise and counter-clockwise to control patient programmer 30 operational status and display 36 illumination. Patient programmer 30 may be prevented from turning OFF during telemetry with IMD 14 or another device to prevent the loss of transmitted data or the stalling of normal operation. Alternatively, patient programmer 30 and IMD 14 may include instructions that handle possible unplanned telemetry interruption, such as battery failure or inadvertent device shutdown.

Display 36 may include any one or more of a liquid crystal display (LCD), dot matrix display, organic light-emitting diode (OLED) display, touch screen, or similar monochrome or color display capable of providing visible information to patient 12. Display 36 may provide a user interface regarding current stimulation therapy, posture state information, provide a user interface for receiving feedback or medication input from patient 12, display an active group of stimulation programs, and display operational status of patient programmer 30 or IMDs 14 or 26. For example, patient programmer 30 may provide a scrollable list of groups, and a scrollable list of programs within each group, via display 36. In addition, display may present a visible posture state indication.

Patient 12 or another user may interact with control pad 40 to navigate through items displayed on display 36. Patient 12 may press control pad 40 on any of arrows 42, 44, 46, and 48 in order to move between items presented on display 36 or move to another screen not currently shown on the display. In some examples, pressing the middle of control pad 40 selects any item highlighted in display 36. In other examples, scroll bars, a scroll wheel, individual buttons, or a joystick may perform the complete or partial functions of control pad 40. In alternative examples, control pad 40 may be a touch pad that allows patient 12 to move a cursor within the user interface displayed on display 36 to manage therapy.

Decrease button 50 and increase button 52 provide an input mechanism for patient 12. In general, activation of decrease button 50 (e.g., by pressing button 50) decreases the value of a highlighted stimulation parameter every time the decrease button is pressed. In contrast, activation of increase button 52 increases the value of a highlighted stimulation parameter one step every time the increase button is pressed. While buttons 50 and 52 may be used to control the value of any stimulation parameter, buttons 50 and 52 may also control patient feedback input. When either button 50 and 52 is selected, patient programmer 30 may initialize communication with IMD 14 or 26 to change therapy accordingly.

When depressed by patient 12, stimulation ON button 54 directs programmer 30 to generate a command for communication to IMD 14, where the command instructs IMD 14 to turn on stimulation therapy. Stimulation OFF button 56 turns off stimulation therapy when depressed by patient 12. Sync button 58 forces patient programmer 30 to communicate with IMD 14. When patient 12 enters an automatic posture response screen of the user interface, pressing sync button 58 turns on the automatic posture response to allow IMD 14 to automatically change therapy according to the posture state of patient 12. Pressing sync button 58 again, when the automatic posture response screen is displayed, turns off the automatic posture response. In the example of FIG. 2, patient 12 may use control pad 40 to adjust the volume, contrast, illumination, time, and measurement units of patient programmer 30.

In some examples, buttons 54 and 56 may be configured to perform operational functions related to stimulation therapy or the use of patient programmer 30. For example, buttons 54 and 56 may control the volume of audible sounds produced by programmer 20, wherein button 54 increases the volume and button 56 decreases the volume. Button 58 may be pressed to enter an operational menu that allows patient 12 to configure the user interface of patient programmer 30 to the desires of patient 12. For example, patient 12 may be able to select a language, backlight delay time, display brightness and contrast, or other similar options. In alternative examples, buttons 50 and 52 may control all operational and selection functions, such as those related to audio volume or stimulation therapy.

Patient programmer 30 may take other shapes or sizes not described herein. For example, patient programmer 30 may take the form of a clam-shell shape, similar to some cellular phone designs. When patient programmer 30 is closed, some or all elements of the user interface may be protected within the programmer. When patient programmer 30 is opened, one side of the programmer may contain a display while the other side may contain input mechanisms. In any shape, patient programmer 30 may be capable of performing the requirements described herein. Alternative examples of patient programmer 30 may include other input mechanisms such as a keypad, microphone, camera lens, or any other media input that allows the user to interact with the user interface provided by patient programmer 30.

In alternative examples, the buttons of patient programmer 30 may perform different functions than the functions provided in FIG. 2 and/or may have a different arrangement. In addition, other examples of patient programmer 30 may include different button layouts or different numbers of buttons. For example, patient programmer 30 may even include a single touch screen that incorporates all user interface functionality with a limited set of buttons or no other buttons.

Figure 3:
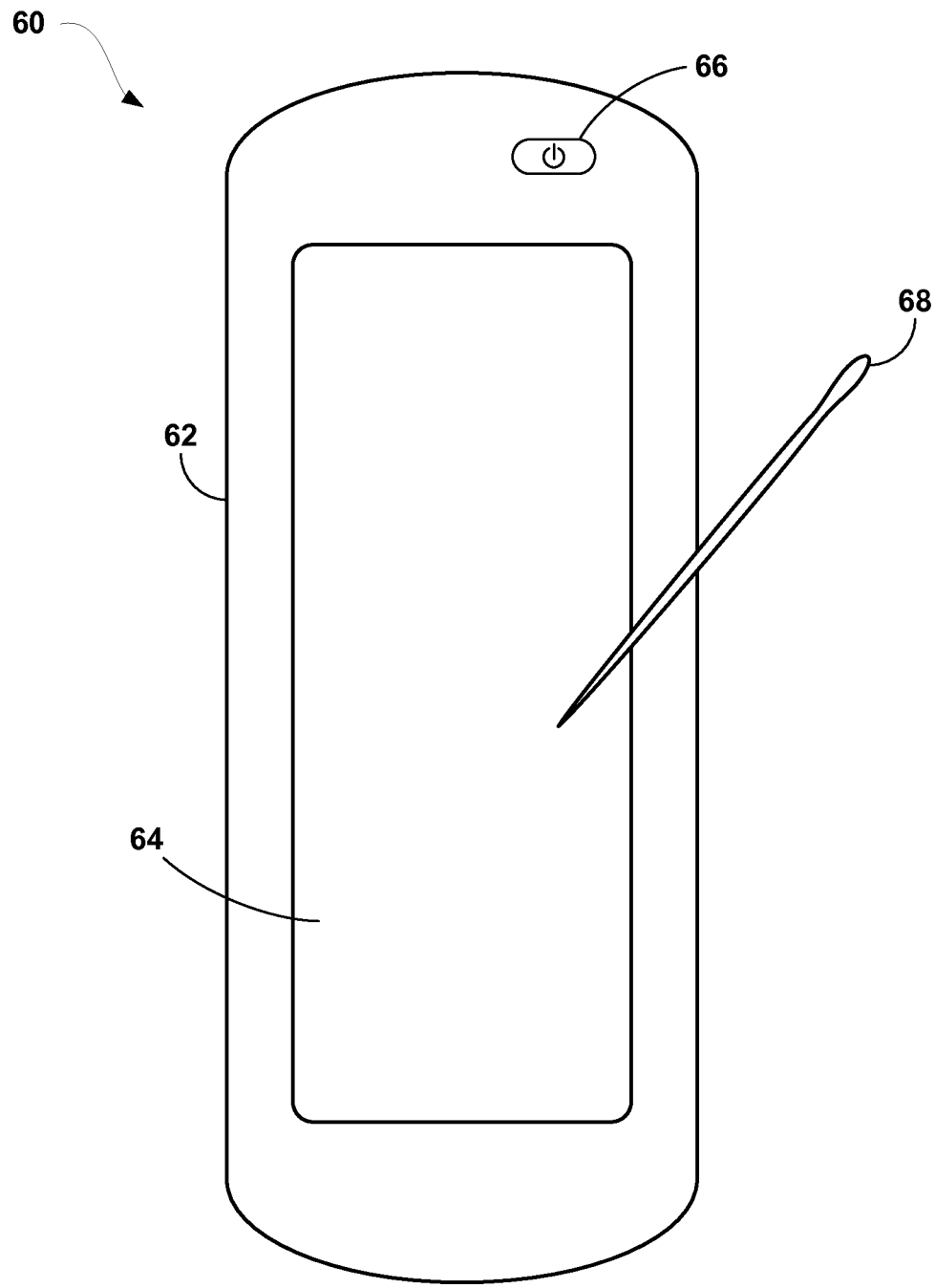
FIG. 3 is a conceptual diagram illustrating an example clinician programmer for programming stimulation therapy delivered by an implantable medical device.

FIG. 3 is a conceptual diagram illustrating an example clinician programmer 60 for programming stimulation therapy delivered by an IMD. Clinician programmer 60 is an example of external programmer 20 illustrated in FIGS. 1A, 1B and 1C and may be used with either IMD 14 or IMD 26. In alternative examples, clinician programmer 60 may be used with an external medical device. As shown in FIG. 3, clinician programmer 60 provides a user interface (not shown) for a user, such as a clinician, physician, technician, or nurse, to manage and program stimulation therapy. In some embodiments, clinician programmer 60 may also be able to present the posture state indication to the user or even select which types of posture state indications will be displayed for patient 12. Clinician programmer 60 is protected by housing 62, which encloses circuitry necessary for clinician programmer 60 to operate.

Clinician programmer 60 includes display 64 and power button 66. In the example of FIG. 3, display 64 is a touch screen that accepts user input via touching certain areas within display 64. The user may use stylus 68 to touch display 64 and select virtual buttons, sliders, keypads, dials, or other such representations presented by the user interface shown by display 64. In some examples, the user may be able to touch display 64 with a finger, pen, or any other pointing device. In alternative examples, clinician programmer 60 may include one or more buttons, keypads, control pads, touch pads, or other devices that accept user input, similar to patient programmer 30.

In the illustrated example, clinician programmer 60 is a hand held device. Clinician programmer 60 may be used within the clinic or on in-house patient calls. Clinician programmer 60 may be used to communicate with multiple IMDs 14 and 26 within different patients. In this manner, clinician programmer 60 may be capable of communicating with many different devices and retain patient data separate for other patient data. In some examples, clinician programmer 60 may be a larger device that may be less portable, such as a notebook computer, workstation, or even a remote computer that communicates with IMD 14 or 26 via a remote telemetry device.

Most, if not all, of clinician programmer 60 functions may be completed via the touch screen of display 64. The user may program stimulation therapy (e.g., selecting stimulation parameters values), modify programs or groups, retrieve stored therapy data, retrieve posture state information from an IMD or another device, define posture states and other activity information, change the contrast and backlighting of display 64, or any other therapy related function. In addition, clinician programmer 60 may be capable of communicating with a networked server in order to send or receive an email or other message, retrieve programming instructions, access a help guide, send an error message, or perform any other function that may be beneficial to prompt therapy.

Housing 62 may be constructed of a polymer, metal alloy, composite, or combination material suitable to protect and contain components of clinician programmer 60. In addition, housing 62 may be partially or completely sealed such that fluids, gases, or other elements may not penetrate the housing and affect components therein. Power button 66 may turn clinician programmer 60 ON or OFF as desired by the user. Clinician programmer 60 may require a password, biometric input, or other security measure to be entered and accepted before the user can use clinician programmer 60.

Clinician programmer 60 may take other shapes or sizes not described herein. For example, clinician programmer 60 may take the form of a clam-shell shape, similar to some cellular phone designs. When clinician programmer 60 is closed, at least a portion of display 64 is protected within housing 62. When clinician programmer 60 is opened, one side of the programmer may contain a display while the other side may contain input mechanisms. In any shape, clinician programmer 60 may be capable of performing the requirements described herein.

Figure 4:
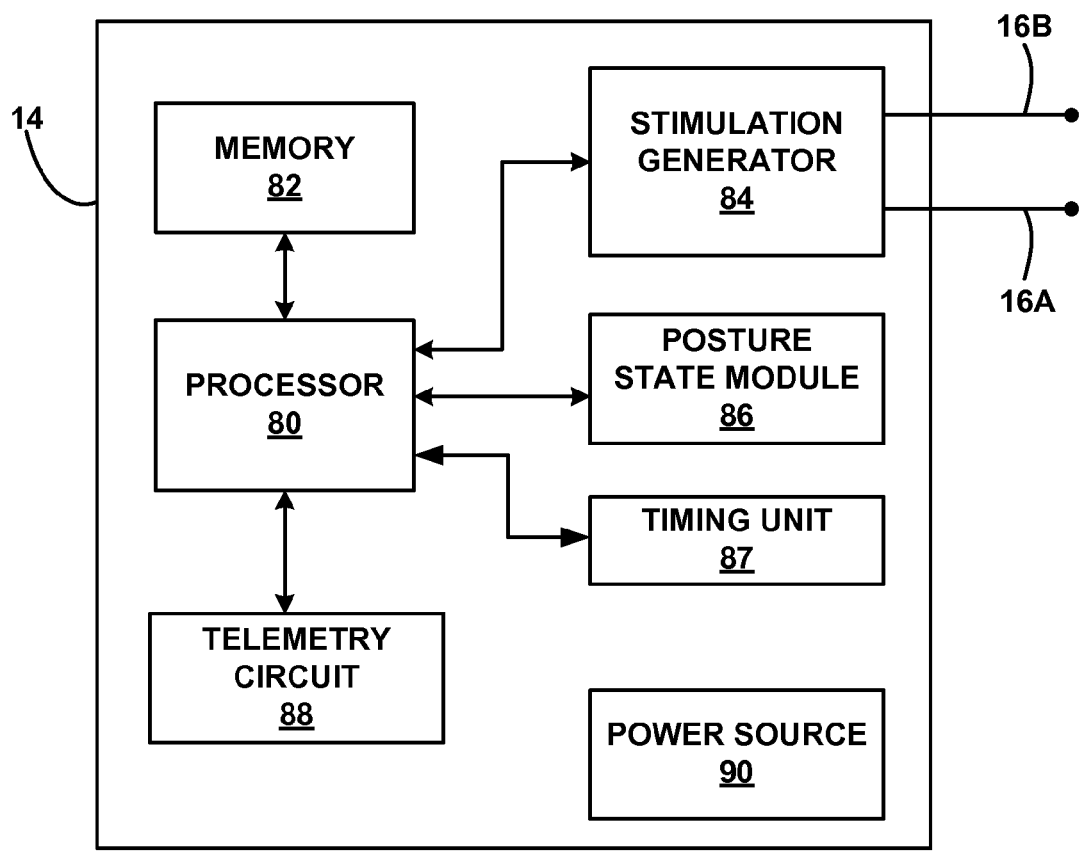
FIG. 4 is a functional block diagram illustrating various components of an example implantable electrical stimulator.

FIG. 4 is a functional block diagram illustrating various components of an IMD 14. In the example of FIG. 4, IMD 14 includes a processor 80, memory 82, stimulation generator 84, posture state module 86, telemetry circuit 88, and power source 90. The stimulation generator 84 forms a therapy delivery module. As shown, IMD 14 also may include timing unit 87.

Memory 82 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media. Memory 82 may store instructions for execution by processor 80, stimulation therapy data, posture state information (e.g., posture state definitions, information associating posture states with therapy programs, and the like), posture state indications, and any other information regarding therapy or patient 12. Therapy information may be recorded for long-term storage and retrieval by a user, and the therapy information may include any data created by or stored in IMD 14. Memory 82 may include separate memories for storing instructions, posture state information, program histories, and any other data that may benefit from separate physical memory modules.

Processor 80 controls stimulation generator 84 to deliver electrical stimulation via electrode combinations formed by electrodes in one or more electrode arrays. For example, stimulation generator 84 may deliver electrical stimulation therapy via electrodes on one or more leads 16, e.g., as stimulation pulses or continuous waveforms. Components described as processors within IMD 14, external programmer 20 or any other device described in this disclosure may each comprise one or more processors, such as one or more microprocessors, digital signal processors (DSPs), application specific integrated circuits (ASICs), field programmable gate arrays (FPGAs), programmable logic circuitry, or the like, either alone or in any suitable combination. The functions attributed to processors described herein may be embodied as software, firmware, hardware, or any combination thereof.

Stimulation generator 84 may include stimulation generation circuitry to generate stimulation pulses or continuous waveforms and, in some examples, switching circuitry to switch the stimulation across different electrode combinations, e.g., in response to control by processor 80. In particular, processor 80 may control the switching circuitry on a selective basis to cause stimulation generator 84 to deliver electrical stimulation to selected electrode combinations and to shift the electrical stimulation to different electrode combinations in a first direction or a second direction when the therapy must be delivered to a different location within patient 12. In other examples, stimulation generator 84 may include multiple current sources to drive more than one electrode combination at one time. In this case, stimulation generator 84 may decrease current to the first electrode combination and simultaneously increase current to the second electrode combination to shift the stimulation therapy.

An electrode configuration, e.g., electrode combination and associated electrode polarities may be represented by a data stored in a memory location, e.g., in memory 82, of IMD 14. Processor 80 may access the memory location to determine the electrode combination and control stimulation generator 84 to deliver electrical stimulation via the indicated electrode combination. To adjust electrode combinations, amplitudes, pulse rates, or pulse widths, processor 80 may command stimulation generator 84 to make the appropriate changes to therapy according to instructions within memory 82 and rewrite the memory location to indicate the changed therapy. In other examples, rather than rewriting a single memory location, processor 80 may make use of two or more memory locations.

When activating stimulation, processor 80 may access not only the memory location specifying the electrode combination but also other memory locations specifying various stimulation parameters such as voltage or current amplitude, pulse width and pulse rate. Stimulation generator 84, e.g., under control of processor 80, then makes use of the electrode combination and parameters in formulating and delivering the electrical stimulation to patient 12.

An exemplary range of electrical stimulation parameters likely to be effective in treating chronic pain, e.g., when applied to spinal cord 18, are listed below. While stimulation pulses are described, stimulation signals may be of any of a variety of forms such as sine waves or the like.

1. Pulse Rate: between approximately 0.5 Hz and approximately 1200 Hz, more preferably between approximately 5 Hz and approximately 250 Hz, and still more preferably between approximately 30 Hz and approximately 130 Hz.

2. Amplitude: between approximately 0.1 volts and approximately 50 volts, more preferably between approximately 0.5 volts and approximately 20 volts, and still more preferably between approximately 1 volt and approximately 10 volts. In other examples, a current amplitude may be defined as the biological load in the voltage that is delivered. For example, the range of current amplitude may be between approximately 0.1 milliamps (mA) and approximately 50 mA.

3. Pulse Width: between approximately 10 microseconds and approximately 5000 microseconds, more preferably between approximately 100 microseconds and approximately 1000 microseconds, and still more preferably between approximately 180 microseconds and approximately 450 microseconds.

In other applications, different ranges of parameter values may be used. For DBS, as one example, alleviation or reduction of symptoms associated with Parkinson's disease, essential tremor, epilepsy, psychiatric disorders or other disorders may make use of stimulation having a pulse rate in the range of approximately 0.5 to approximately 1200 Hz, such as between approximately 5 to approximately 250 Hz, or between approximately 30 to approximately 185 Hz, and a pulse width in the range of approximately 10 microseconds and 5000 microseconds, such as between approximately 60 microseconds and approximately 1000 microseconds, or between approximately 60 microseconds and approximately 450 microseconds, or between approximately 60 microseconds and approximately 150 microseconds. Amplitude ranges such as those described above with reference to SCS, or other amplitude ranges, may be used for different DBS applications.

Processor 80 stores stimulation parameters in memory 82, e.g., as programs and groups of programs. Upon selection of a particular program group, processor 80 may control stimulation generator 84 to deliver stimulation according to the programs in the groups, e.g., simultaneously or on a time-interleaved basis. A group may include a single program or multiple programs. As mentioned previously, each program may specify a set of stimulation parameters, such as amplitude, pulse width and pulse rate. In addition, each program may specify a particular electrode combination for delivery of stimulation. Again, the electrode combination may specify particular electrodes in a single array or multiple arrays, e.g., on a single lead or among multiple leads. Processor 80 also may control telemetry circuit 88 to send and receive information to and from external programmer 20. For example, telemetry circuit 88 may send information to and receive information from patient programmer 30.

Posture state module 86 allows IMD 14 to sense the patient posture state, e.g., posture, activity or any other static position or motion of patient 12. In the example of FIG. 4, posture state module 86 includes one or more accelerometers, such as three-axis accelerometers, capable of detecting static orientation or vectors in three-dimensions. Example accelerometers include micro-electro-mechanical accelerometer. In other examples, posture state module 86 may alternatively or additionally include one or more gyroscopes, piezoelectetric crystals, pressure transducers or other sensors to sense the posture state of patient 12. Posture state information generated by posture state module 86 and processor 80 may correspond to an activity and/or posture undertaken by patient 12 or a gross level of physical activity, e.g., activity counts based on footfalls or the like.

Posture state information from posture state module 86 may be stored in memory 82 for later review by a clinician, used to adjust therapy, present a posture state indication to patient 12 (e.g., via patient programmer 30) or some combination thereof. As an example, processor 80 may record the posture state parameter value, or output, of the 3-axis accelerometer and assign the posture state parameter value to a certain predefined posture indicated by the posture state parameter value. In this manner, IMD 14 may be able to track how often patient 12 remains within a certain posture. IMD 14 may also store which group or program was being used to deliver therapy when patient 12 was in the sensed posture. Further, processor 80 may also adjust therapy for a new posture when posture state module 86 indicates that patient 12 has in fact changed postures. Therefore, IMD 14 may be configured to provide posture-responsive stimulation therapy to patient 12. Stimulation adjustments in response to posture state may be automatic or semi-automatic (subject to patient approval). In many cases, fully automatic adjustments may be desirable so that IMD 14 may react more quickly to posture state changes.

A posture state parameter value from posture state module 86 that indicates the posture state may constantly vary throughout the day of patient 12. However, a certain activity (e.g., walking, running, or biking) or a posture (e.g., standing, sitting, or lying down) may include multiple posture state parameter values from posture state module 86. Memory 82 may include definitions for each posture state of patient 12. In one example, the definition of each posture state may be illustrated as a cone in three-dimensional space. Whenever the posture state parameter value, e.g., a vector, from the three-axis accelerometer of posture state module 86 resides within a predefined cone, processor 80 indicates that patient 12 is in the posture state of the cone. In other examples, posture state parameter value from the 3-axis accelerometer may be compared to a look-up table or equation to determine the posture state in which patient 12 currently resides.

Posture-responsive stimulation may allow IMD 14 to implement a certain level of automation in therapy adjustments. Automatically adjusting stimulation may free patient 12 from the constant task of manually adjusting therapy each time patient 12 changes posture or starts and stops a certain posture state. Such manual adjustment of stimulation parameters can be tedious, requiring patient 12 to, for example, depress one or more keys of patient programmer 30 multiple times during the patient posture state to maintain adequate symptom control. In some examples, patient 12 may eventually be able to enjoy posture state responsive stimulation therapy without the need to continue making changes for different postures via patient programmer 30. Instead, patient 12 may transition immediately or over time to fully automatic adjustments based on posture state.

According to some examples described herein, IMD 14 may automatically adjust the delivery of therapy by automatically suspending one or more aspects of posture responsive therapy and/or by adjusting, e.g., decreasing, the frequency at which posture state module 86 detects the posture state of patient based on time, e.g., time of day. Timing unit 87 may monitor time of day, day of the week, or any other timing parameter. Processor 80 may access timing unit 87 anytime to determine the time, and then compare the time to instructions stored in memory 82 defining particular automatically adjustment times or time ranges to determine if posture-responsive therapy should be automatic suspended or the posture state detection frequency should be automatically adjusted. Although shown in IMD 14 in FIG. 4, the timing unit (as with the processor that performs the therapy parameter selections) may be alternatively located in a programmer. Also, a programmer could include a precise clock that periodically synchronizes a rough clock in the implantable medical device.

Although posture state module 86 is described as containing the 3-axis accelerometer, posture state module 86 may contain multiple single-axis accelerometers, dual-axis accelerometers, 3-axis accelerometers, or some combination thereof. In some examples, an accelerometer or other sensor may be located within or on IMD 14, on one of leads 16 (e.g., at the distal tip or at an intermediate position), an additional sensor lead positioned somewhere within patient 12, within an independent implantable sensor, or even worn on patient 12. For example, one or more microsensors may be implanted within patient 12 to communicate posture state information wirelessly to IMD 14. In this manner, the patient posture state may be determined from multiple posture state sensors placed at various locations on or within the body of patient 12.

In other examples, posture state module 86 may additionally or alternatively be configured to sense one or more physiological parameters of patient 12. For example, physiological parameters may include heart rate, electromyography (EMG), an electroencephalogram (EEG), an electrocardiogram (ECG), temperature, respiration rate, or pH. These physiological parameters may be used by processor 80, in some examples, to confirm or reject changes in sensed posture state that may result from vibration, patient travel (e.g., in an aircraft, car or train), or some other false positive of posture state.

In some examples, processor 80 processes the analog output of the posture state sensor in posture state module 86 to determine activity and/or posture data. For example, where the posture state sensor comprises an accelerometer, processor 80 or a processor of posture state module 86 may process the raw signals provided by the posture state sensor to determine activity counts. In some examples, processor 80 may process the signals provided by the posture state sensor to determine velocity of motion information along each axis.

In one example, each of the x, y, and z signals provided by the posture state sensor has both a DC component and an AC component. The DC components describes the gravitational force exerted upon the sensor and can thereby be used to determine orientation of the sensor within the gravitational field of the earth. Assuming the orientation of the sensor is relatively fixed with respect to the patient, the DC components of the x, y and z signals may be utilized to determine the patient's orientation within the gravitational field, and hence to determine the posture of the patient.

The AC component of the x, y and z signals yields information about patient motion. In particular, the AC component of a signal may be used to derive a value for an activity describing the patient's motion. This activity may involve a level, direction of motion, or acceleration of the patient.

One method for determining the patient activity is by determining an activity count. An activity count may be used to indicate the activity or activity level of patient 12. For example, a signal processor may sum the magnitudes of the AC portion of an accelerometer signal for N consecutive samples. For instance, assuming sampling occurs as 25 Hz, N may be set to 25, so that count logic provides the sum of the samples that are obtained in one second. This sum may be referred to as an "activity count". The number "N" of consecutive samples may be selected by the processor based on the current posture state, if desired. The activity count may be the activity portion of the activity parameter value that is added to the posture portion. The resulting activity parameter value may then incorporate both activity and posture to generate an accurate indication of the motion of patient 12.

As another example, the activity parameter value may be defined describing direction of motion. This activity parameter value may be associated with a vector and an associated tolerance, which may be a distance from the vector. Another example of an activity parameter value relates to acceleration. The value quantifying a level of change of motion over time in a particular direction may be associated with this parameter referenced in the activity parameter value.

IMD 14 wirelessly communicates with external programmer 20, e.g., patient programmer 30 or clinician programmer 60, or another device by radio frequency (RF) communication or proximal inductive interaction of IMD 14 with external programmer 20. Telemetry circuit 88 may send information to and receive information from external programmer 20 on a continuous basis, at periodic intervals, at non-periodic intervals, or upon request from the stimulator or programmer. To support RF communication, telemetry circuit 88 may include appropriate electronic components, such as amplifiers, filters, mixers, encoders, decoders, and the like.

When the posture state parameter value indicates that patient 12 has changed to a different posture state, processor 80 may communicate with patient programmer 30 via telemetry circuitry 88. In this manner, processor 80 may force patient programmer 30 to present a different posture state indication based upon the sensed posture state parameter value of the patient posture state. Alternatively, processor 80 may periodically or non-periodically send posture state information to patient programmer 30 either unilaterally or in response to a request from patient programmer 30. For example, patient programmer 30 may request the posture state parameter value or current sensed posture state from processor 80 and independently change the posture state indication when it is appropriate to do so in view of the posture state information received from processor 80.

Power source 90 delivers operating power to the components of IMD 14. Power source 90 may include a small rechargeable or non-rechargeable battery and a power generation circuit to produce the operating power. Recharging may be accomplished through proximal inductive interaction between an external charger and an inductive charging coil within IMD 14. In some examples, power requirements may be small enough to allow IMD 14 to utilize patient motion and implement a kinetic energy-scavenging device to trickle charge a rechargeable battery. In other examples, traditional batteries may be used for a limited period of time. As a further alternative, an external inductive power supply could transcutaneously power IMD 14 when needed or desired.

Figure 5:
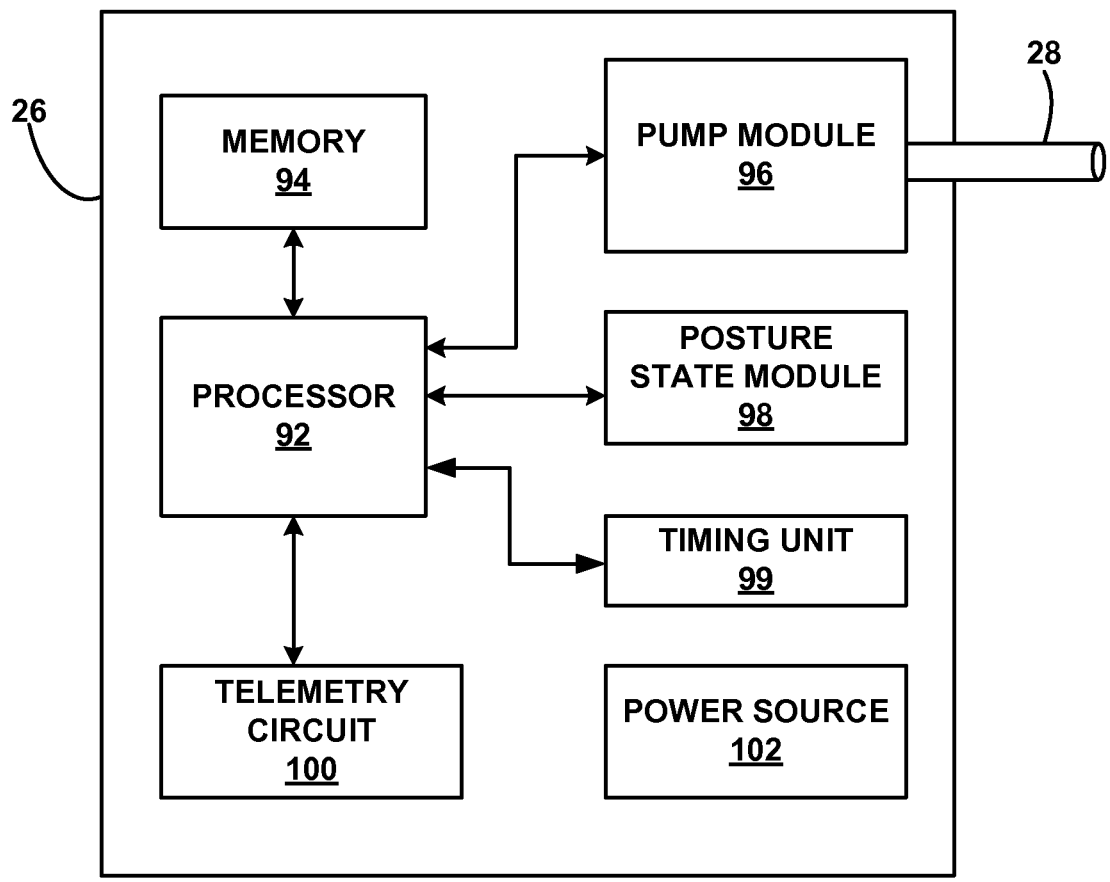
FIG. 5 is a functional block diagram illustrating various components of an example implantable drug pump.

FIG. 5 is a functional block diagram illustrating various components of an IMD 26, which delivers a therapeutic agent to patient 12. IMD 26 is a drug pump that operates substantially similar to IMD 14 of FIG. 4, but delivers a therapeutic agent instead of electrical stimulation. IMD 26 includes processor 92, memory 94, pump module 96, posture state module 98, timing unit 99, telemetry circuit 100, and power source 102. Instead of stimulation generator 84 of IMD 14, IMD 26 includes pump module 96 for delivering drugs or some other therapeutic agent via catheter 28. Pump module 96 may include a reservoir to hold the drug and a pump mechanism to force drug out of catheter 28 and into patient 12.

Processor 92 controls pump module 96 according to therapy instructions stored within memory 94. For example, memory 94 may contain the programs or groups of programs that define the drug delivery therapy for patient 12. A program may indicate the bolus size or flow rate of the drug, and processor 92 may accordingly deliver therapy. Processor 92 may also use posture state information from posture state 98 to adjust drug delivery therapy when patient 12 changes posture states, e.g., adjusts his or her posture.

Figure 6:
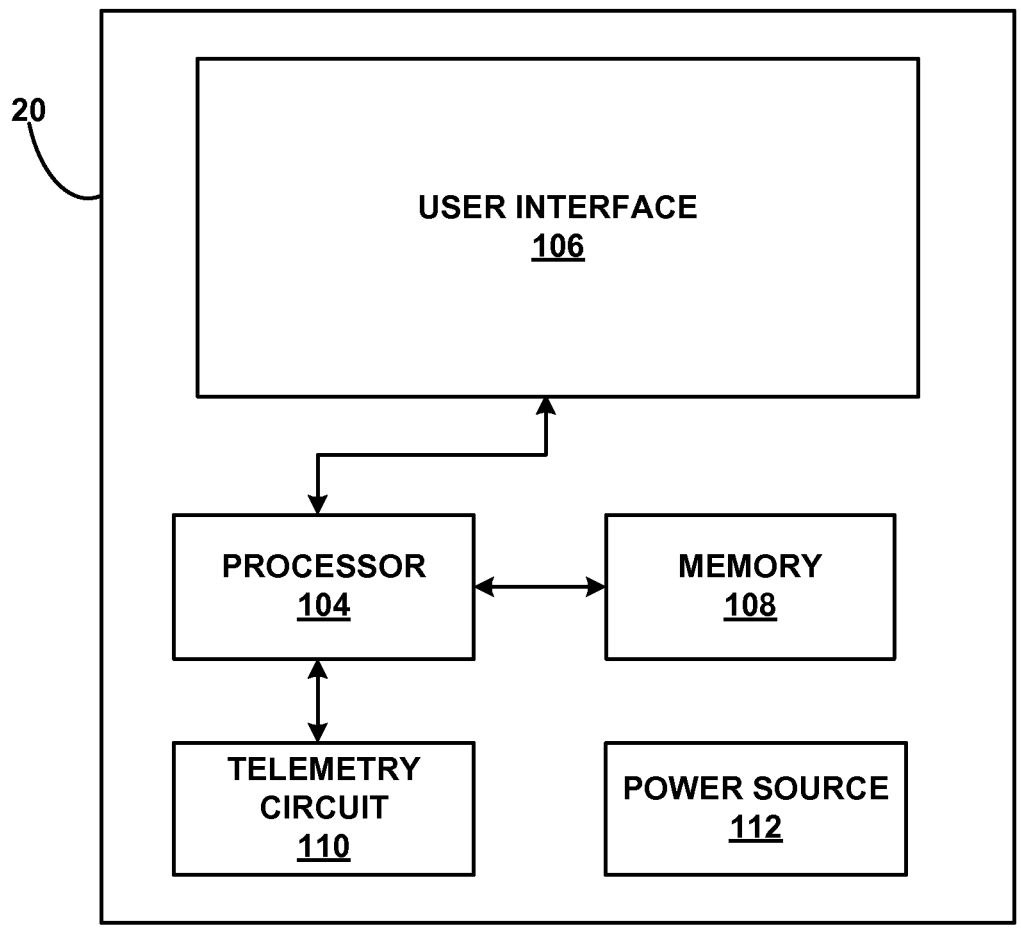
FIG. 6 is a functional block diagram illustrating various components of an example external programmer for an implantable medical device.

FIG. 6 is a functional block diagram illustrating various components of an external programmer 20 for IMDs 14 or 26. Programmer 20 may be a handheld computing device, a workstation or another dedicated or multifunction computing device. For example, programmer 20 may be a general purpose computing device (e.g., a personal computer, personal digital assistant (PDA), cell phone, and so forth) or may be a computing device dedicated to programming the IMD. As shown in FIG. 6, external programmer 20 includes processor 104, memory 108, telemetry circuit 110, user interface 106, and power source 112. External programmer 20 may be embodied as patient programmer 30 or clinician programmer 60.

Processor 104 processes instructions by memory 108 and may store user input received through user interface 106 into the memory when appropriate for the current therapy. In addition, processor 104 provides and supports any of the functionality described herein with respect to each example of user interface 106. Processor 104 may comprise any one or more of a microprocessor, DSP, ASIC, FPGA, or other digital logic circuitry, and the functions attributed to programmer 104 may be embodied as software, firmware, hardware or any combination thereof.

Memory 108 may include any one or more of a RAM, ROM, EEPROM, flash memory or the like. Memory 108 may include instructions for operating user interface 106, telemetry module 110 and managing power source 112. Memory 108 may store program instructions that, when executed by processor 104, cause processor 104 and programmer 20 to provide the functionality ascribed to them herein. Memory 108 also includes instructions for generating and delivering programming commands to IMD 14, such as a programming command that instructs IMD 14 to activate or deactivate a posture-responsive therapy mode. Memory 108 may also include a removable memory portion that may be used to provide memory updates or increases in memory capacities. A removable memory may also allow patient data to be easily transferred to another computing device, or to be removed before programmer 20 is used to program therapy for another patient.

A clinician or patient 12 interacts with user interface 106 in order to manually change the stimulation parameters values of a program, change programs within a group, turn posture-responsive stimulation ON or OFF, view therapy information, view posture state information, view a posture state indication, or otherwise communicate with IMDs 14 or 26.

User interface 106 may include a screen and one or more input mechanisms, such as buttons as in the example of patient programmer 30, that allow external programmer 20 to receive input from a user. Alternatively, user interface 106 may additionally or only utilize a touch screen display, as in the example of clinician programmer 60. The screen may be a liquid crystal display (LCD), dot matrix display, organic light-emitting diode (OLED) display, touch screen, or any other device capable of delivering and/or accepting information. For visible posture state indications, a display screen may suffice. For audible and/or tactile posture state indications, programmer 20 may further include one or more audio speakers, voice synthesizer chips, piezoelectric buzzers, or the like.

Input mechanisms for user interface 106 may include a touch pad, increase and decrease buttons, emergency shut off button, and other buttons needed to control the stimulation therapy, as described above with regard to patient programmer 30. Processor 104 controls user interface 106, retrieves data from memory 108 and stores data within memory 108. Processor 104 also controls the transmission of data through telemetry circuit 110 to IMDs 14 or 26. Memory 108 includes operation instructions for processor 104 and data related to patient 12 therapy.

Telemetry circuit 110 allows the transfer of data to and from IMD 14, or IMD 26. Telemetry circuit 110 may communicate automatically with IMD 14 at a scheduled time or when the telemetry circuit detects the proximity of the stimulator. Alternatively, telemetry circuit 110 may communicate with IMD 14 when signaled by a user through user interface 106. To support RF communication, telemetry circuit 110 may include appropriate electronic components, such as amplifiers, filters, mixers, encoders, decoders, and the like. Power source 112 may be a rechargeable battery, such as a lithium ion or nickel metal hydride battery. Other rechargeable or conventional batteries may also be used. In some cases, external programmer 20 may be used when coupled to an alternating current (AC) outlet, i.e., AC line power, either directly or via an AC/DC adapter.

Although not shown in FIG. 6, in some examples, external programmer 20 may include a charger module capable of recharging a power source, such as a rechargeable battery that may be included in power source 90 of IMD 14. Hence, in some cases, the programmer may be integrated with recharging components to form a combined programmer/recharger unit.

Figure 7:
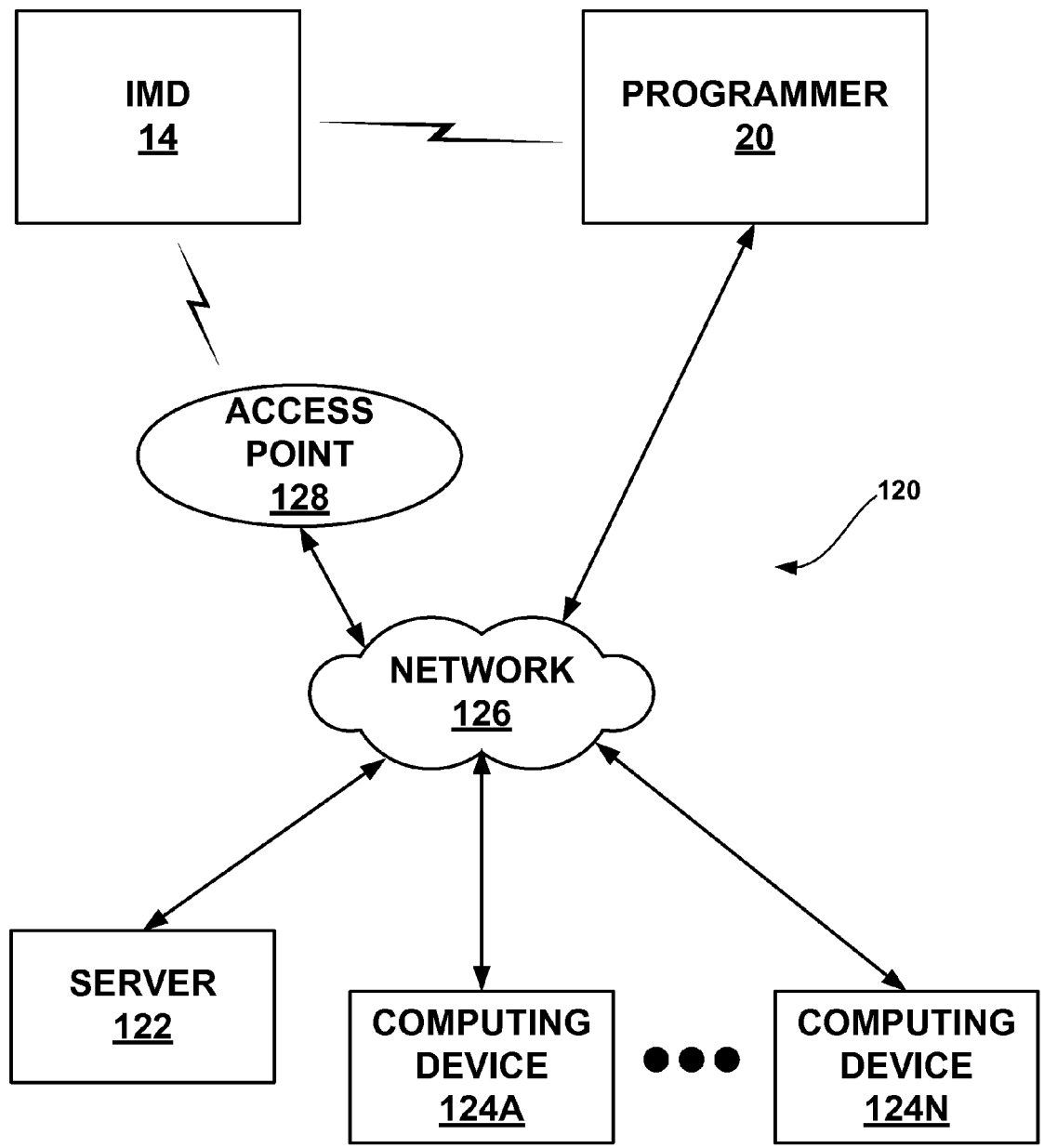
FIG. 7 is a block diagram illustrating an example system that includes an external device, such as a server, and one or more computing devices that are coupled to an implantable medical device and external programmer shown in FIGS. 1A-1C via a network.

FIG. 7 is a block diagram illustrating an example system 120 that includes an external device, such as a server 122, and one or more computing devices 124A-124N, that are coupled to IMD 14 and external programmer 20 shown in FIGS. 1A-1C via a network 126. In this example, IMD 14 may use its telemetry circuit 88 (FIG. 4) to communicate with external programmer 20 via a first wireless connection, and to communicate with an access point 128 via a second wireless connection. In other examples, IMD 26 may also be used in place of IMD 14, and external programmer 20 may be either patient programmer 30 or clinician programmer 60.

In the example of FIG. 7, access point 128, external programmer 20, server 122, and computing devices 124A-124N are interconnected, and able to communicate with each other, through network 126. In some cases, one or more of access point 128, external programmer 20, server 122, and computing devices 124A-124N may be coupled to network 126 through one or more wireless connections. IMD 14, external programmer 20, server 122, and computing devices 124A-124N may each comprise one or more processors, such as one or more microprocessors, DSPs, ASICs, FPGAs, programmable logic circuitry, or the like, that may perform various functions and operations, such as those described in this disclosure.

Access point 128 may comprise a device, such as a home monitoring device, that connects to network 126 via any of a variety of connections, such as telephone dial-up, digital subscriber line (DSL), or cable modem connections. In other examples, access point 128 may be coupled to network 126 through different forms of connections, including wired or wireless connections.

During operation, IMD 14 may collect and store various forms of data. For example, IMD 14 may collect sensed posture state information during therapy that indicate how patient 12 moves throughout each day. In some cases, IMD 14 may directly analyze the collected data to evaluate the patient posture state, such as what percentage of time patient 12 was in each identified posture. In other cases, however, IMD 14 may send stored data relating to posture state information to external programmer 20 and/or server 122, either wirelessly or via access point 128 and network 126, for remote processing and analysis. For example, IMD 14 may sense, process, trend and evaluate the sensed posture state information. This communication may occur in real time, and network 126 may allow a remote clinician to review the current patient posture state by receiving a presentation of a posture state indication on a remote display, e.g., computing device 124A. Alternatively, processing, trending and evaluation functions may be distributed to other devices such as external programmer 20 or server 122, which are coupled to network 126. In addition, posture state information may be archived by any of such devices, e.g., for later retrieval and analysis by a clinician.

In some cases, IMD 14, external programmer 20 or server 122 may process posture state information or raw data and/or therapy information into a displayable posture state report, which may be displayed via external programmer 20 or one of computing devices 124A-124N. The posture state report may contain trend data for evaluation by a clinician, e.g., by visual inspection of graphic data. In some cases, the posture state report may include the number of activities patient 12 conducted, a percentage of time patient 12 was in each posture state, the average time patient 12 was continuously within a posture state, what group or program was being used to deliver therapy during each activity, the number of adjustments to therapy during each respective posture state, or any other information relevant to patient 12 therapy, based on analysis and evaluation performed automatically by IMD 14, external programmer 20 or server 122. A clinician or other trained professional may review and/or annotate the posture state report, and possibly identify any problems or issues with the therapy that should be addressed.

Using a system as shown in FIG. 7, a clinician, physician, technician, or even patient 12, may review objectivity data with respect to the posture states of patient 12. The objectivity data may be sleep quality information or proportional posture information that indicates how patient 12 has been moving during the symptom diagnosis or delivered therapy. The user may remotely monitor the progress and trends of patient 12, limiting the number of times that patient 12 may need to physically visit the clinician. The remote monitoring supported by system 120 may also reduce the time needed to find efficacious therapy parameters by allowing the clinician to more frequently monitor sleep quality information and proportional posture information. Any of the user interfaces described herein with respect to patient programmer 30 or clinician programmer 60 may also be presented via any of computing devices 124A-124N.

In some cases, server 122 may be configured to provide a secure storage site for archival of posture state information that has been collected from IMD 14 and/or external programmer 20. Network 126 may comprise a local area network, wide area network, or global network, such as the Internet. In some cases, external programmer 20 or server 122 may assemble posture state information in web pages or other documents for viewing by trained professionals, such as clinicians, via viewing terminals associated with computing devices 124A-124N. System 120 may be implemented, in some aspects, with general network technology and functionality similar to that provided by the Medtronic CareLink® Network developed by Medtronic, Inc., of Minneapolis, Minn.

Although some examples of the disclosure may involve posture state information and data, system 120 may be employed to distribute any information relating to the treatment of patient 12 and the operation of any device associated therewith. For example, system 120 may allow therapy errors or device errors to be immediately reported to the clinician. In addition, system 120 may allow the clinician to remotely intervene in the therapy and reprogram IMD 14, patient programmer 30, or communicate with patient 12. In an additional example, the clinician may utilize system 120 to monitor multiple patients and share data with other clinicians in an effort to coordinate rapid evolution of effective treatment of patients. Further, posture state detection may also be used to provide notifications, such as providing notification via a wireless link to a care giver that a patient has potentially experienced a fall.

Furthermore, although the disclosure is described with respect to SCS therapy, such techniques may be applicable to IMDs that convey other therapies in which posture state information is important, such as, e.g., DBS, pelvic floor stimulation, gastric stimulation, occipital stimulation, functional electrical stimulation, and the like. Also, in some aspects, techniques for evaluating posture state information, as described in this disclosure, may be applied to IMDs that are generally dedicated to sensing or monitoring and do not include stimulation or other therapy components. For example, an implantable monitoring device may be implanted in conjunction with an implantable stimulation device, and be configured to evaluate sensing integrity of leads or electrodes associated with the implantable monitoring device based on sensed signals evoked by delivery of stimulation by the implantable stimulation device.

Figure 8A:
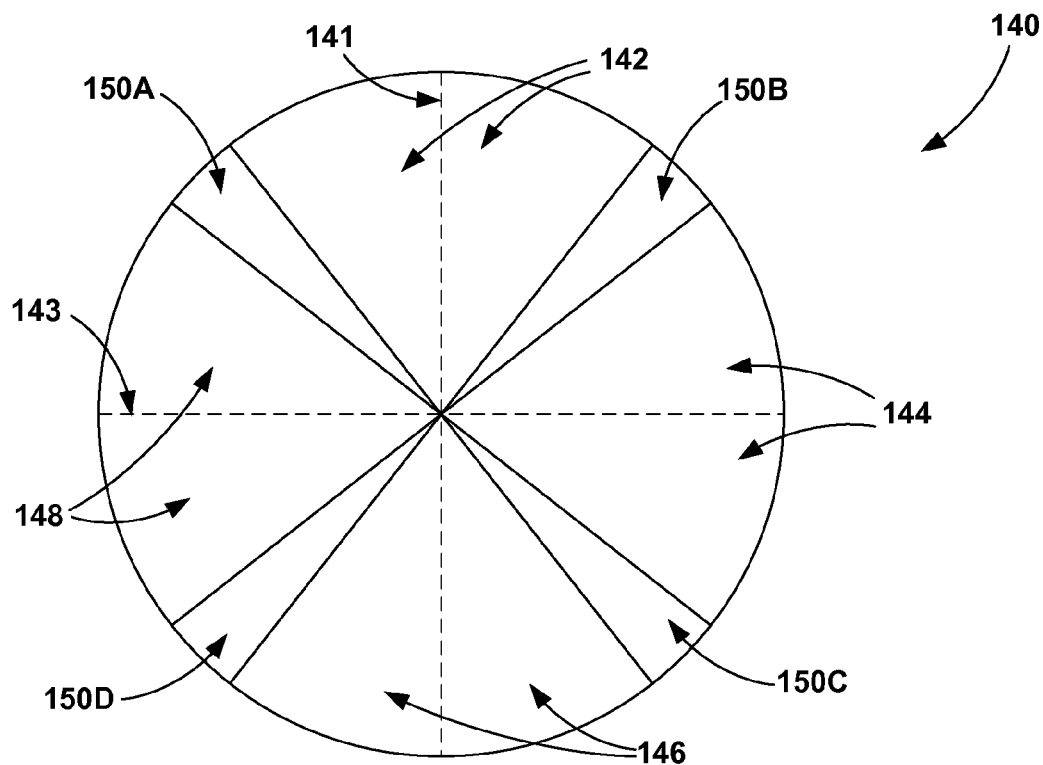
FIGS. 8A-8C are conceptual illustrations of example posture state spaces within which postures state reference data may define the posture state of a patient.
Figure 8B:
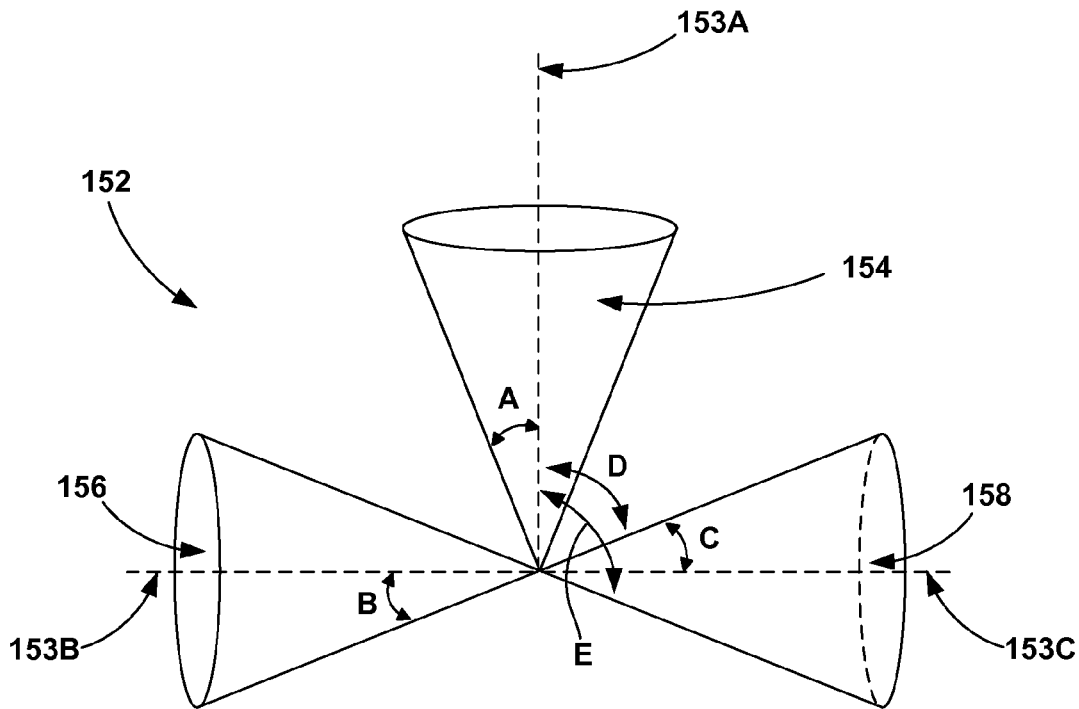
Figure 8C:
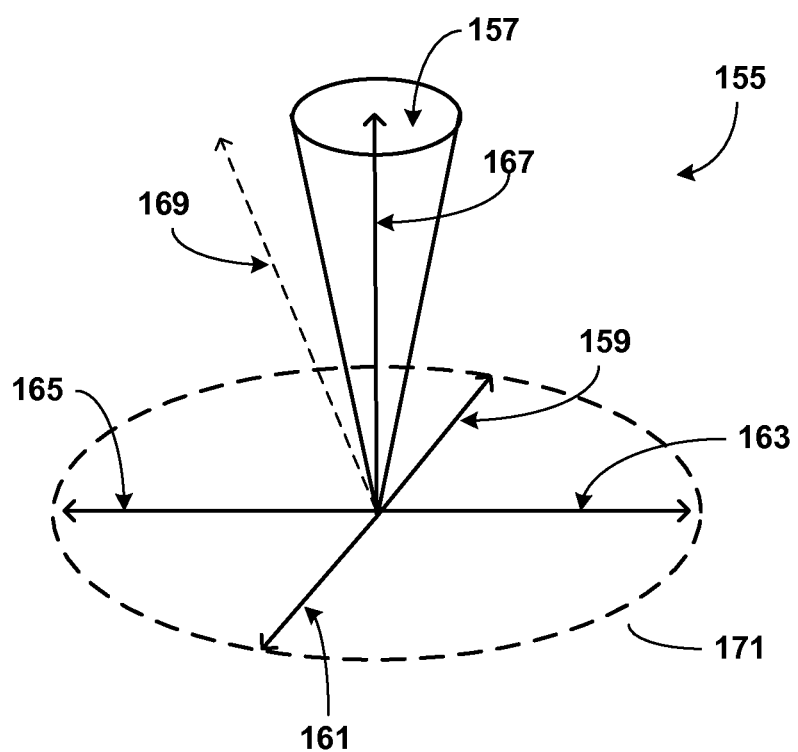

FIGS. 8A-8C are conceptual illustrations of posture state spaces 140, 152, 155 within which posture state reference data may define the posture state of patient 12. Posture state reference data may define certain regions associated with particular posture states of patient 12 within the respective posture state spaces 140, 152, 155. The output of one or more posture state sensors may be analyzed by posture state module 86 with respect to posture state spaces 140, 152, 155 to determine the posture state of patient 12. For example, if the output of one or more posture state sensors is within a particular posture region defined by posture state reference data, posture state module 86 may determine that patient 12 is within the posture state associated with the respective posture state region.

In some cases, one or more posture state regions may be defined as posture state cones. Posture state cones may be used to define a posture state of patient 12 based on the output from a posture state sensor of a posture state according to an example method for posture state detection. A posture state cone may be centered about a posture state reference coordinate vector that corresponds to a particular posture state. In the examples of FIGS. 8A and 8B, the posture state module 86 of IMD 14 or IMD 26 may use a posture state sensor, e.g., a three-axis accelerometer that provides data indicating the posture state of patient 12, to sense posture vectors. While the sensed data may be indicative of any posture state, postures of patient 12 will generally be used below to illustrate the concept of posture cones. As shown in FIG. 8A, posture state space 140 represents a vertical plane dividing patient 12 from left and right sides, or the sagittal plane. A posture state parameter value from two axes of the posture state sensor may be used to determine the current posture state of patient 12 according to the posture state space 140. The posture state data may include x, y and z coordinate values.

A posture cone may be defined by a reference coordinate vector for a given posture state in combination with a distance or angle defining a range of coordinate vectors within a cone surrounding the posture reference coordinate vector. Alternatively, a posture cone may be defined by a reference coordinate vector and a range of cosine values computed using the reference coordinate vector as an adjacent vector and any of the outermost vectors of the cone as a hypotenuse vector. If a sensed posture state vector is within an applicable angle or distance of the reference coordinate vector, or if the sensed posture state vector and the reference coordinate vector produce a cosine value in a specified cosine range, then posture state vector is determined to reside within the posture cone defined by the reference coordinate vector.

Posture state space 140 is segmented into different posture cones that are indicative of a certain posture state of patient 12. In the example of FIG. 8A, upright cone 142 indicates that patient 12 is sitting or standing upright, lying back cone 148 indicates that patient 12 is lying back down, lying front cone 144 indicates that patient 12 is lying chest down, and inverted cone 146 indicates that patient 12 is in an inverted position. Other cones may be provided, e.g., to indicate that patient 12 is lying on the right side or left side. For example, a lying right posture cone and a lying left posture cone positioned outside of the sagittal plane illustrated in FIG. 8A. In particular, the lying right and lying left posture cones may be positioned in a coronal plane substantially perpendicular to the sagittal plane illustrated in FIG. 8A. For ease of illustration, lying right and lying left cones are not shown in FIG. 8A.

Vertical axis 141 and horizontal axis 143 are provided for orientation of posture state area 140, and are shown as orthogonal for purposes of illustration. However, posture cones may have respective posture reference coordinate vectors that are not orthogonal in some cases. For example, individual reference coordinate vectors for cones 142 and 146 may not share the same axis, and reference coordinate vectors for cones 144 and 148 may not share the same axis. Also, reference coordinate vectors for cones 144 and 148 may or may not be orthogonal to reference coordinates vectors for cones 142, 146. Therefore, although orthogonal axes are shown in FIG. 8A for purposes of illustration, respective posture cones may be defined by individualized reference coordinate vectors for the cones.

IMD 14 may monitor the posture state parameter value of the posture state sensor to produce a sensed coordinate vector and identify the current posture of patient 12 by identifying which cone the sensed coordinated vector of the posture state sensor module 86 resides. For example, if the posture state parameter value corresponds to a sensed coordinate vector that falls within lying front cone 144, IMD 14 determines that patient 12 is lying down on their chest. IMD 14 may store this posture information as a determined posture state or as raw output from the posture state sensor, change therapy according to the posture, or both. Additionally, IMD 14 may communicate the posture information to patient programmer 30 so that the patient programmer can present a posture state indication to patient 12.

In addition, posture state area 140 may include hysteresis zones 150A, 150B, 150C, and 150D (collectively "hysteresis zones 150"). Hysteresis zones 150 are positions within posture state area 140 where no posture cones have been defined. Hysteresis zones 150 may be particularly useful when IMD 14 utilizes the posture state information and posture cones to adjust therapy automatically. If the posture state sensor indicates that patient 12 is in upright cone 142, IMD 14 would not detect that patient 12 has entered a new posture cone until the posture state parameter value indicates a different posture cone. For example, if IMD 14 determines that patient 12 moves to within hysteresis zone 150A from upright cone 142, IMD 14 retains the posture as upright. In this manner, IMD 14 does not change the corresponding therapy until patient 12 fully enters a different posture cone. Hysteresis zones 150 prevent IMD 14 from continually oscillating between different therapies when patient 12's posture state resides near a posture cone boundary.

Each posture cone 142, 144, 146, 148 may be defined by an angle in relation to a reference coordinate vector defined for the respective posture cone. Alternatively, some posture cones may be defined by an angle relative to a reference coordinate vector for another posture cone. For example, lying postures may be defined by an angle with respect to a reference coordinate vector for an upright posture cone. In each case, as described in further detail below, each posture cone may be defined by an angle in relation to a reference coordinate posture vector defined for a particular posture state. The reference coordinate vector may be defined based on posture sensor data generated by a posture state sensor while patient 12 occupies a particular posture state desired to be defined using the reference coordinate vector. For example, a patient may be asked to occupy a posture so that a reference coordinate vector can be sensed for the respective posture. In this manner, vertical axis 141 may be specified according to the patient's actual orientation. Then, a posture cone can be defined using the reference coordinate vector as the center of the cone.

Vertical axis 141 in FIG. 8A may correspond to a reference coordinate vector sensed while the patient was occupying an upright posture state. Similarly, a horizontal axis 143 may correspond to a reference coordinate vector sensed while the patient is occupying a lying posture state. A posture cone may be defined with respect to the reference coordinate vector. Although a single axis is shown extending through the upright and inverted cones 142, 146, and another single axis is shown extending through the lying down and lying up cones 144, 148, individual reference coordinate vectors may be used for respective cones, and the reference coordinate vectors may not share the same axes, depending on differences between the reference coordinate vectors obtained for the posture cones.

Posture cones may be defined by the same angle or different angles, symmetrical to either axis, or asymmetrical to either axis. For example, upright cone 142 may have an angle of eighty degrees, +40 degrees to −40 degrees from the positive vertical axis 141. In some cases, lying cones may be defined relative to the reference coordinate vector of the upright cone 142. For example, lying up cone 148 may have an angle of eighty degrees, −50 degrees to −130 degrees from the positive vertical axis 141. Inverted cone 146 may have an angle of eighty degrees, −140 degrees to +140 degrees from vertical axis 141. In addition, lying down cone 144 may have an angle of eighty degrees, +50 degrees to +130 degrees from the positive vertical axis 141. In other examples, each posture cone may have varying angle definitions, and the angles may change during therapy delivery to achieve the most effective therapy for patient 12.

Alternatively or additionally, instead of an angle, posture cones 144, 146, 148, 148 may be defined by a cosine value or range of cosine values in relation to vertical axis 141, horizontal axis 143, or some other axis, such as, e.g., individual reference coordinate vectors for the respective cones. For example, a posture cone may be defined by a cosine value that defines the minimum cosine value, calculated using a reference coordinate vector and a respective coordinate vector sensed by a posture state sensor at any point in time. In the cosine computation, the value (adjacent/hypotenuse) can be computed using the magnitude of the coordinate reference vector as the adjacent and a vector at the outermost extent of the cone as the hypotenuse to define a range of cosine values consistent with the outer bound of the cone.

For upright cone 142, the cosine range may extend from the maximum cosine value of 1.0, corresponding to a sensed vector that matches the reference coordinate vector of the upright cone, to a minimum cosine value that corresponds to a sensed vector at the outer limit of the upright cone. As another example, for lying cone 144, the cosine range may extend from the maximum cosine value of 1.0, corresponding to a sensed vector that matches the reference coordinate vector of the lying cone, to a minimum cosine value that corresponds to a sensed vector at the outer limit of the lying cone. Alternatively, the lying cone 144 may be defined with reference to the upright cone 142, such that the cosine range may extend between a maximum and minimum values determined relative to the reference coordinate vector for the upright cone.

In other examples, posture state area 140 may include additional posture cones than those shown in FIG. 8A. For example, a reclining cone may be located between upright cone 142 and lying back cone 148 to indicate when patient 12 is reclining back (e.g., in a dorsal direction). In this position, patient 12 may need a different therapy to effectively treat symptoms. Different therapy programs may provide efficacious therapy to patient 12 when patient 12 is in each of an upright posture (e.g., within upright cone 142), lying back posture (e.g., within lying back cone 148), and a reclining back posture. Thus, a posture cone that defines the reclining back posture may be useful for providing efficacious posture-responsive therapy to patient 12. In other examples, posture state area 140 may include fewer posture cones than cones 142, 144, 146, 148 shown in FIG. 8A. For example, inverted cone 146 may be replaced by a larger lying back cone 148 and lying front cone 144.

FIG. 8B illustrates an example posture state space 152 that is a three-dimensional space in which the posture state parameter value from the posture state sensor is placed in relation to the posture cones. Posture state space 152 is substantially similar to posture state area 140 of FIG. 8A. However, the posture state parameter value derived from all three axes of a 3-axis accelerometer may be used to accurately determine the posture state of patient 12. In the example of FIG. 8B, posture state space 152 includes upright cone 154, lying back cone 156, and lying front cone 158. Posture state space 152 also includes hysteresis zones (not shown) similar to those of posture state area 140. In the example of FIG. 8B, the hysteresis zones are the spaces not occupied by a posture cone, e.g., upright cone 154, lying back cone 156, and lying front cone 158.

Posture cones 154, 156 and 158 also are defined by a respective center line 153A, 153B, or 153C, and associated cone angle A, B or C. For example, upright cone 154 is defined by center line 153A that runs through the center of upright cone 154. Center line 153A may correspond to an axis of the posture state sensor or some other calibrated vector. In some embodiments, each center line 153A, 153B, 153C may correspond to a posture reference coordinate vectors defined for the respective postures, e.g., the upright posture. For instance, assuming that patient 12 is standing, the DC portion of the x, y, and z signals detected by the posture state sensor of posture state module 86 define a posture vector that corresponds to center line 153A. The x, y, and z signals may be measured while patient 12 is known to be in a specified position, e.g., standing, and the measured vector may be correlated with the upright posture state. Thereafter, when the DC portions of the posture state sensor signal are within some predetermined cone tolerance or proximity, e.g., as defined by an angle, distance or cosine value, of the posture reference coordinate vector (i.e., center line 153A), it may be determined that patient 12 is in the upright posture. In this manner, a sensed posture coordinate vector may be initially measured based on the output of one or more posture state sensors of posture state module 86, associated with a posture state, such as upright, as a reference coordinate vector, and then later used to detect a patient's posture state.

As previously indicated, it may be desirable to allow some tolerance to be associated with a defined posture state, thereby defining a posture cone or other volume. For instance, in regard to the upright posture state, it may be desirable to determine that a patient who is upright but leaning slightly is still in the same upright posture state. Thus, the definition of a posture state may generally include not only a posture reference coordinate vector (e.g., center line 153A), but also a specified tolerance. One way to specify a tolerance is by providing an angle, such as cone angle A, relative to coordinate reference vector 153A, which results in posture cone 154 as described herein. Cone angle A is the deflection angle, or radius, of upright cone 154. The total angle that each posture cone spans is double the cone angle. The cone angles A, B, and C may be generally between approximately 1 degree and approximately 70 degrees. In other examples, cone angles A, B, and C may be between approximately 10 degrees and 30 degrees. In the example of FIG. 8B, cone angles A, B, and C are approximately 20 degrees. Cone angles A, B, and C may be different, and center lines 153A, 153B, and 153C may not be orthogonal to each other.

In some examples, a tolerance may be specified by a cosine value or range of cosine values. The use of cosine values, in some cases, may provide substantial processing efficiencies. As described above, for example, a minimum cosine value, determined using the reference coordinate vector as adjacent and sensed coordinate vector as hypotenuse, indicates the range of vectors inside the cone. If a sensed coordinate vector, in conjunction with the reference coordinate vector for a posture cone, produces a cosine value that is less than the minimum cosine value for the posture cone, the sensed coordinate vector does not reside within the pertinent posture cone. In this manner, the minimum cosine value may define the outer bound of a range of cosine values within a particular posture cone defined in part by a reference coordinate vector.

While center lines 153A, 153B, 153C of each of the posture cones 154, 156, 158, respectively, are shown in FIG. 8B as being substantially orthogonal to each other, in other examples, center lines 153A, 153B, and 153C may not be orthogonal to each other. Again, the relative orientation of center lines 153A, 153B, 153C may depend on the actual reference coordinate vector output of the posture state sensor of posture state module 86 of IMD 14 when patient 12 occupies the respective postures.

In some cases, all of the posture cones may be individually defined based on actual reference coordinate vectors. Alternatively, in some cases, some posture cones may be defined with reference to one or more reference coordinate vectors for one or more other posture cones. For example, lying reference coordinate vectors could be assumed to be orthogonal to an upright reference coordinate vector. Alternatively, lying reference coordinate vectors could be individually determined based on sensed coordinate vectors when the patient is in respective lying postures. Hence, the actual reference coordinate vectors for different postures may be orthogonal or non-orthogonal with respect to one another.

In addition to upright cone 154, lying back cone 156, and lying front cone 158, posture state space 152 may include additional posture cones. For example, a lying right cone may be provided to define a patient posture in which patient 12 is lying on his right side and a lying left cone may be provided to define a patient posture in which patient 12 is lying on his left side. In some cases, the lying right cone and lying left cone may be positioned approximately orthogonal to upright cones 154, in approximately the same plane as lying back cone 156 and lying front cone 158. Moreover, posture state space 152 may include an inverted cone positioned approximately opposite of upright cone 154. Such a cone indicates that the patient's posture is inverted from the upright posture, i.e., upside down.

In some examples, to detect the posture state of a patient, posture state module 86 of IMD 14 may determine a sensed coordinate vector based on the posture sensor data generated by one or more posture state sensors, and then analyze the sensed coordinate vector with respect to posture cones 154, 156, 158 of FIG. 8B. For example, in a case in which a posture cone is defined by a reference coordinate vector and a tolerance angle, e.g., tolerance angle "A," posture state module 86 may determine whether the sensed coordinate vector is within upright posture cone 154 by calculating the angle between the sensed coordinate vector and reference coordinate vector, and then determine whether the angle is less than the tolerance angle "A." If so, posture state module 86 determines that the sensed coordinate vector is within upright posture cone 154 and detects that patient 12 is in the upright posture. If posture state module 86 determines that sensed coordinate vector is not within upright posture cone 154, posture state module 86 detects that patient 12 is not in the upright posture.

Posture state module 86 may analyze the sensed coordinate vector in posture state space 152 with respect to each individual defined posture cone, such as posture cones 156 and 158, in such a manner to determine the posture state of patient 12. For example, posture state module 86 may determine the angle between the sensed coordinate vector and reference coordinate vector of individual posture cones defined for the posture state, and compare the determined angle to the tolerance angle defined for the respective posture cone. In this manner, a sensed coordinate vector may be evaluated against each posture cone until a match is detected, i.e., until the sensed coordinate vector is found to reside in one of the posture cones. Hence, a cone-by-cone analysis is one option for posture detection.

In other examples, different posture detection analysis techniques may be applied. For example, instead of testing a sensed coordinate vector against posture cones on a cone-by-cone basis, a phased approach may be applied where the sensed coordinate vector is classified as either upright or not upright. In this case, if the sensed coordinate vector is not in the upright cone, posture state module 86 may determine whether the sensed coordinate vector is in a lying posture, either by testing the sensed coordinate vector against individual lying posture cones or testing the sensed coordinate vector against a generalized lying posture volume, such as a donut- or toroid-like volume that includes all of the lying postures, and may be defined using an angle or cosine range relative to the upright vector, or relative to a modified or virtual upright vector as will be described. In some cases, if lying postures are defined by cones, the lying volume could be defined as a logical OR of the donut- or toroid-like volume and the volumes of the lying posture cones. If the cones are larger such that some portions extend beyond the lying volume, then those portions can be added to the lying volume using the logical OR-like operation.

If the sensed coordinate vector resides within the donut- or toroid-like lying volume, then the sensed coordinate vector may be tested against each of a plurality of lying posture cones in the lying volume. Alternatively, the posture detection technique may not use lying cones. Instead, a posture detection technique may rely on a proximity test between the sensed coordinate vector and each of the reference coordinate vectors for the respective lying postures. The proximity test may rely on angle, cosine value or distance to determine which of the lying posture reference coordinate vectors is closest to the sensed coordinate vector. For example, the reference coordinate vector that produces the largest cosine value with the sensed coordinate vector as hypotenuse and the reference coordinate vector as adjacent is the closest reference coordinate vector. In this case, the lying posture associated with the reference coordinate vector producing the largest cosine value is the detected posture. Hence, there are a variety of ways to detect posture, such as using posture cones, using an upright posture cone with lying volume and lying posture cone test, or using an upright posture cone with lying volume and lying vector proximity test.

As a further illustration of an example posture detection technique, posture state module 86 may first determine whether patient 12 is generally in a lying posture state or upright posture state by analyzing the sensed coordinate vector in posture state space 152 with respect to an axis 153A for the upright posture state. Axis 153A may correspond to the upright reference coordinate vector. For example, angle "A" may be used to define upright posture cone 154, as described above, and angles "D" and "E" may be used to define the vector space in which patient 12 may be generally considered to be in the lying posture state, regardless of the particular posture state cone, e.g., lying front cone 158, lying back cone 156, lying right cone (not shown), or lying left cone (not shown), in which the sensed coordinate vector falls.

If it is determined that a sensed coordinate vector is not within an angle A of the axis 153A, then it may be determined that the patient is not in the upright posture indicated by the upright posture cone. In this case, it may next be determined whether a sensed coordinated vector is generally in a lying posture space volume, which may be considered somewhat donut- or toroid-like, and may be defined relative to the upright reference coordinate vector 153A. As shown, angles "D" and "E" define the minimum and maximum angle values, respectively, that a sensed vector may form with respect to axis 153A of patient 12 for a determination to be made that the patient is generally in the lying posture state. Again, cosine values may be used instead of angles to determine the positions of sensed coordinate vectors relative to posture cones or other posture volumes, or relative to reference coordinate vectors.

As illustrated, angles "D" and "E' may be defined with respect to vertical axis 153A (which may correspond to an upright reference coordinate vector), which is the reference coordinate vector for the upright posture cone, rather than with respect to a reference coordinate vector of a lying posture state cone. If a sensed vector is within the angular range of D to E, relative to axis 153A, then it can be determined by posture state module 86 that the patient is generally in a lying posture. Alternatively, in some examples, an angle C could be defined according to a generally horizontal axis 153C (which may correspond to one of the lying reference coordinate vectors). In this case, if a sensed vector is within angle C of axis 153C, it can be determined by posture state module 86 that the patient is in a lying posture. In each case, the region generally defining the lying posture state may be referred to as a posture donut or posture toroid, rather than a posture cone. The posture donut may generally encompass a range of vectors that are considered to be representative of various lying down postures.

As an alternative, posture state module 86 may rely on cosine values or a range of cosine values to define the posture donut or toroid with respect to axis 153A. When the sensed vector falls within the vector space defined by axis 153A and angles "D" and "E", or produces a cosine value with the reference coordinate vector 153A in a prescribed range, posture state module 86 may determine that patient 12 is generally in a lying posture state. For example, if the sensed vector and reference coordinate vector 153 produce a cosine value in a first range, the posture is upright. If the cosine value is in a second range, the posture is lying. If the cosine value is outside of the first and second ranges, the posture may be indeterminate. The first range may correspond to the range of cosine values that would be produced by vectors in posture cone 154 defined by angle A, and the second range may be correspond to cosine values that would be produced by vectors in the posture donut defined by angles D and E.

When the sensed vector fall within the vector space defined by axis 153A and angles "D" and "E", as indicated by angle or cosine value, posture state module 86 may then determine the particular lying posture state occupied by patient 12, e.g., lying front, lying back, lying right, or lying left. To determine the particular lying posture state occupied by patient 12, posture state module 86 may analyze the sensed vector with respect to reference coordinate vectors for individual lying posture state cones, e.g., lying front cone 156, lying back cone 158, lying right cone (not shown), and lying left cone (not shown), using one more techniques previously described, such as angle or cosine techniques. For example, posture state module 86 may determine whether the sensed coordinated vector resides within one of the lying posture state cones and, if so, select the posture state corresponding to that cone as the detected posture state.

FIG. 8C illustrates an example posture state space 155 that is a three-dimensional space substantially similar to posture state space 152 of FIG. 8B. Posture state space 155 includes upright posture cone 157 defined by reference coordinate vector 167. The tolerance that defines upright posture cone 157 with respect to reference coordinate vector 167 may include a tolerance angle or cosine value, as described above. In contrast to determining whether a sensed coordinate vector resides in a lying cone, FIG. 8C illustrates a method for detecting a lying posture based on proximity of a sensed coordinate vector to one of the reference coordinate vectors for the lying postures.

As shown in FIG. 8C, posture state space 155 includes four reference coordinate vectors 159, 161, 163, 165, which are associated with lying left, lying right, lying front, and lying back posture states, respectively. Posture state module 86 may have defined each of the four reference coordinated vector 159, 161, 163, 165 based on the output of one or more posture sensors while patient 12 occupied each of the corresponding posture states. Unlike lying front and lying back posture cones 158, 156 in the example of FIG. 8B, the posture state reference data for the four defined posture states corresponding to reference vectors 159, 161, 163, 165 need not include angles defined relative to the respective reference vector in a manner that defines a posture cone. Rather, as will be described below, the respective posture state reference vectors may be analyzed with respect to one another in terms of cosine values to determine which particular reference coordinate vector is nearest in proximity to a sensed coordinate vector.

In some examples, to determine the posture state of patient 12, posture state module 85 may determine whether a sensed coordinate vector is within upright posture cone 157 by analyzing the sensed coordinate vector in view of the tolerance angle or cosine value(s) defined with respect to upright posture reference coordinate vector 167, or whether the sensed vector is within a posture donut or toroid defined by a range of angles (as in FIG. 8B) or cosine values with respect to upright posture reference coordinate vector 167, in which case posture state module 86 may determine that patient 12 is in a general lying posture state.

If posture state module 86 determines that patient 12 is occupying a general lying posture state, posture state module 86 may then calculate the cosine value of the sensed coordinate vector with respect to each lying reference coordinate vectors 159, 161, 163, 165. In such a case, posture state module 86 determines the particular lying posture state of patient 12, i.e., lying left, lying right, lying front, lying back, based on which cosine value is the greatest of the four cosine values. For example, if the cosine value calculated with the sensed vector as the hypotenuse and the lying front reference vector 163 as the adjacent vector is the largest value of the four cosine values, the sensed vector may be considered closest in proximity to lying front reference vector out of the four total reference vectors 159, 161, 163, 165. Accordingly, posture state module 85 may determine that patient 12 is occupying a lying front posture state.

In some examples, posture state module 86 may determine whether patient 12 is generally in a lying posture state based on the relationship of a sensed vector to upright reference vector 167. For example, as described above, a lying posture donut or toroid may be defined with respect to upright posture reference vector 167, e.g., using angles D and E as in FIG. 8B. Such a technique may be appropriate when lying posture reference vectors 159, 161, 163, 165 define a common plane substantially orthogonal to upright posture reference vector 167. However, the lying posture reference vectors 159, 161, 163, 165 may not in fact be orthogonal to the upright reference coordinate vector 167. Also, the lying posture reference vectors 159, 161, 163, 165 may not reside in the same plane.

To account for non-orthogonal reference vectors, in other examples, a lying posture donut or toroid may be defined with respect to a modified or virtual upright reference vector 169 rather than that actual upright posture reference vector 167. Again, such a technique may be used in situations in which the lying reference vectors 159, 161, 163, 165 are not in a common plane, or the common plane of reference vector 159, 161, 163, 165 is not substantially orthogonal to upright reference vector 167. However, use of the example technique is not limited to such situations.

To define virtual upright reference vector 169, posture state module 86 may compute the cross-products of various combinations of lying reference vectors 159, 161, 163, 165 and average the cross product values. In the example of FIG. 8C, posture state module 86 may compute four cross products and average the four cross product vectors to yield the virtual upright vector. The cross product operations that may be performed are: lying left vector 159×lying back vector 165, lying back vector 165×lying right vector 161, lying right vector 161×lying front vector 163, and lying front vector 163×lying left vector 159. Each cross product yields a vector that is orthogonal to the two lying reference vectors that were crossed. Averaging each of the cross product vectors yields a virtual upright reference vector that is orthogonal to lying plane 171 approximately formed by lying reference vectors 159, 161, 163, 165.

Using virtual upright reference vector 169, posture state module 86 may define a lying posture donut or toroid in a manner similar to that described with respect to upright reference vector 167, but instead with respect to virtual upright reference vector 169. In particular, when posture state module 86 determines that the patient is not in the upright posture, the posture state module determines whether the patient is in a lying posture based on an angle or cosine value with respect to the virtual upright reference vector 169.

Posture state module 86 may still determine whether patient 12 is in an upright posture state using upright posture cone 157. If posture state module 86 determines that patient 12 is occupying a general lying posture state based on the analysis of the sensed coordinate vector with respect to virtual upright reference vector 169, posture state module 86 may then calculate the cosine value of the sensed coordinate vector (as hypotenuse) with respect to each lying reference coordinate vectors 159, 161, 163, 165 (as adjacent).

In such a case, posture state module 86 determines the particular lying posture state of patient 12, i.e., lying left, lying right, lying front, lying back, based on which cosine value is the greatest of the four cosine values. For example, if the cosine value calculated with the lying front reference vector 163 is the largest value of the four cosine values, the sensed vector may be considered closest in proximity to lying front reference vector out of the four total reference vectors 159, 161, 163, 165. Accordingly, posture state module 85 may determine that patient 12 is occupying a lying front posture state.

Additionally, posture state definitions are not limited to posture cones. For example, a definition of a posture state may involve a posture vector and a tolerance, such as a maximum distance from the posture vector. So long as a detected posture vector is within this maximum distance from the posture vector that is included in the definition of the posture state, patient 12 may be classified as being in that posture state. This alternative method may allow posture states to be detected without calculating angles, as is exemplified above in the discussion related to posture cones.

Further to the foregoing, posture states may be defined that are specific to a particular patient's activities and/or profession. For instance, a bank teller may spend a significant portion of his working day leaning forward at a particular angle. A patient-specific "Leaning Forward" posture state including this angle may be defined. The cone angle or other tolerance value selected for this posture state may be specific to the particular posture state definition for this patient. In this manner, the defined posture states may be tailored to a specific user, and need not be "hard-coded" in the IMD.

In some examples, individual posture states may be linked together, thereby tying posture states to a common set of posture reference data and a common set of therapy parameter values. This may, in effect, merge multiple posture cones for purposes of posture state-based selection of therapy parameter values. For example, all lying posture state cones (back, front, left, right) could be treated as one cone or a donut/toroid, e.g., using a technique the same as or similar to that described with respect to FIGS. 8B and 8C to define a donut, toroid or other volume. One program group or common set of therapy parameter values may apply to all posture states in the same merged cone, according to the linking status of the posture states, as directed via external programmer 20.

Merging posture cones or otherwise linking a plurality of posture states together may be useful for examples in which a common set of therapy parameter values provides efficacious therapy to patient 12 for the plurality of posture states. In such an example, linking a plurality of posture states together may help decrease the power consumption required to provide posture-responsive therapy to patient 12 because the computation required to track patient posture states and provide responsive therapy adjustments may be minimized when a plurality of posture states are linked together.

Linking of posture states also may permit a therapy parameter value adjustment in one posture state to be associated with multiple posture states at the same time. For example, the same amplitude level for one or more programs may be applied to all of the posture states in a linked set of posture states. Alternatively, the lying down posture states may all reside within a "donut" or toroid that would be used instead of separate cones 156 and 158, for example. The toroid may be divided into sectional segments that each correspond to different posture states, such as lying (back), lying (front), lying (right), lying (left) instead of individual cones. In this case, different posture reference data and therapy parameter values may be assigned to the different sectional segments of the toroid.

Figure 9:
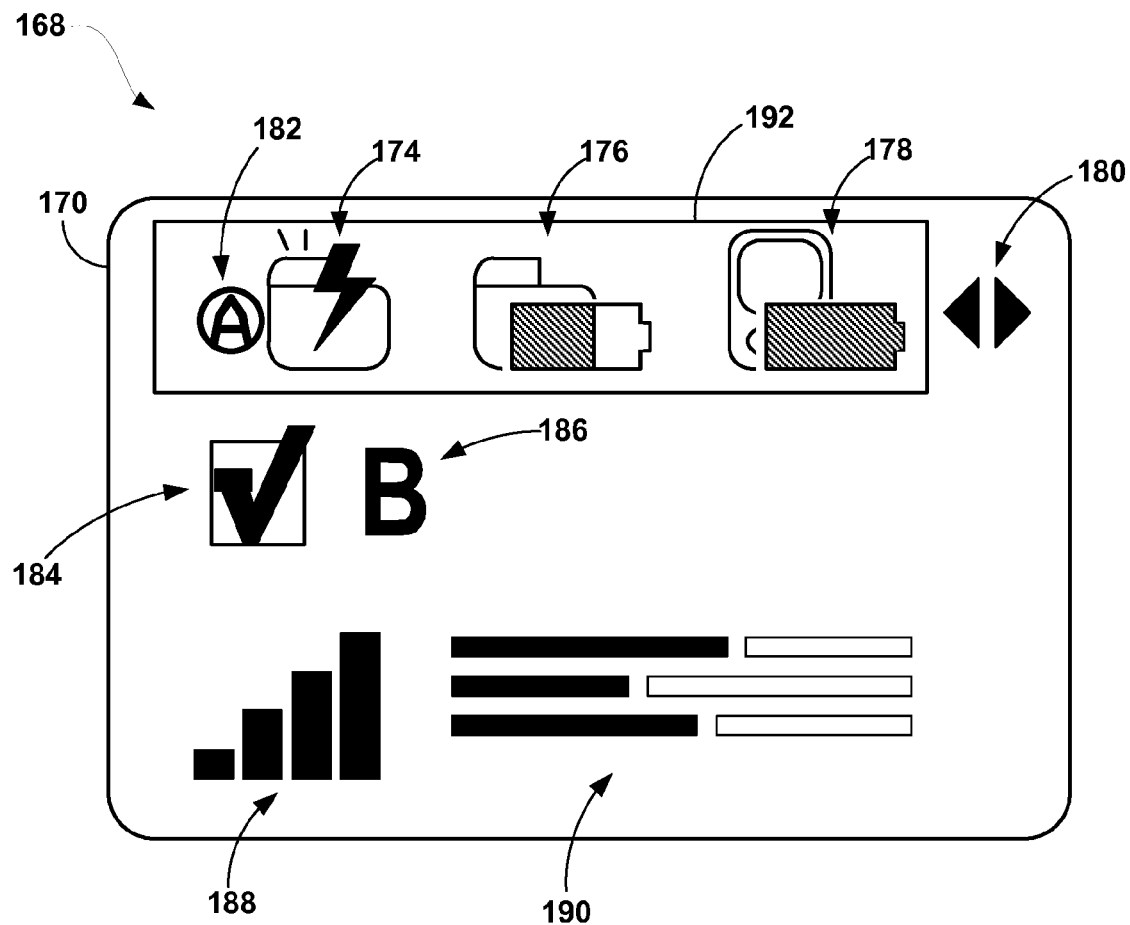
FIG. 9 is a conceptual diagram illustrating an example user interface of a patient programmer for delivering therapy information to the patient.

FIG. 9 is a conceptual diagram illustrating an example user interface 168 of a patient programmer, such as, e.g., patient programmer 30 (FIG. 2), for delivering therapy information to patient 12. In other examples, a user interface similar to user interface 168 may be presented by clinician programmer 60 (FIG. 3). In the example of FIG. 9, display 36 of patient programmer 30 provides user interface 168 to the user, such as patient 12, via screen 170. Screen 170 includes stimulation icon 174, IMD battery icon 176, programmer battery icon 178, navigation arrows 180, automatic posture response icon 182, group selection icon 184, group identifier 186, program identifier 188, amplitude graph 190, and selection box 192. User interface 168 provides information to patient 12 regarding group, program, amplitude, and automatic posture response status. User interface 168 may be configurable, such that more or less information may be provided to patient 12, as desired by the clinician or patient 12.

Selection box 192 allows patient 12 to navigate to other screens, groups, or programs using navigation arrows 180 to manage the therapy. In the example, of screen 170, selection box 192 is positioned so that patient 12 may use arrows 44 and 48 (FIG. 2) of control pad 40 of programmer 30 to move to the automatic posture response screen, the volume screen, the contrast or illumination screen, the time screen, and the measurement unit screen (not all shown) of patient programmer 30. In these screens, patient 12 may be able to control the use of the automatic posture response feature and adjust the patient programmer 30 features. Patient 12 may only adjust the features surrounded by selection box 192.

Group identifier 186 indicates one of possibly several groups of programs that can be selected for delivery to patient 12, e.g., via IMD 14. Group selection icon 184 indicates whether the displayed group, e.g., group B in FIG. 9, is actually selected for therapy delivery to patient 12. If a presently displayed group is currently selected for delivery to patient 12, group selection icon 184 includes a box with a checkmark. If a presently displayed group is not currently selected for delivery to patient 12, group selection icon 184 includes a box without a checkmark. For example, a group not currently selected for delivery to patient 12 may include a group preprogrammed based on suggested default parameter values, which patient 12 has determined to not be effective. To navigate through the stored program groups, a user may use control pad 40 to move selection box 192 to select the group identifier 186 and then use control pad 40 to scroll through the various groups, e.g., A, B, C, and so forth. IMD 14 may be programmed to support a small number of groups and/or a large number of groups, where each group contains a small number of programs or a large number of programs that are delivered simultaneously, in sequence, or on a time-interleaved basis.

For each group, group selection icon 184 indicates the appropriate status. For a given group, program identifier 188 indicates one of the programs associated with the group. In the example of FIG. 9, no program number is indicated in program identifier 188 because all of the programs' amplitudes are shown in each bar of amplitude graph 190. Solid portions of the bars of graph 190 indicate the relative amplitude values IMD 14 currently is using to deliver stimulation therapy to patient 12, while open portions of the bars indicate the remaining amplitude available to each program. In some examples, numerical values of each program's amplitude may be shown in addition to or in place of amplitude graph 190. In other examples of user interface 168 specific to drug delivery using IMD 26, amplitude graph 190 may show the flow rate of drugs or frequency of bolus delivery to patient 12. This information may be shown in numerical format as well. Patient 12 may encompass group selection icon 184 and group identifier 186 with selection box 192 to scroll between the different programs of the selected group.

Automatic posture response icon 182 indicates that IMD 14 is generally activated, such that processor 80 automatically delivers therapy to patient 12 based upon the posture state detected by posture state module 86. In particular, automatic posture-responsive therapy may involve processor 80 adjusting one or more therapy parameter values, selecting different therapy programs, and/or selecting different therapy program groups based on the detected posture state of the patient. However, automatic posture response icon 182 is not present next to group identifier 186, indicating to the user that group "B" does not have automatic posture-responsive therapy activated for any of the therapy programs within group "B."

Some groups or individual programs in groups may support automatic posture-responsive therapy. For example, automatic adjustment of one or more therapy parameter values in response to the detected posture state of patient 12 may be selectively activated or deactivated based on settings entered by a clinician, or possibly patient 12. Hence, some programs or groups may be configured for use with posture-responsive therapy while other programs or groups may not be configured for use with posture-responsive therapy. In some cases, if posture-responsive therapy supported by the automatic posture response feature of IMD 14 is desired, patient 12 may need to switch therapy to a different group that has automatic posture responsive therapy activated for IMD 14 to adjust therapy according to the patient posture state.

Figure 10:
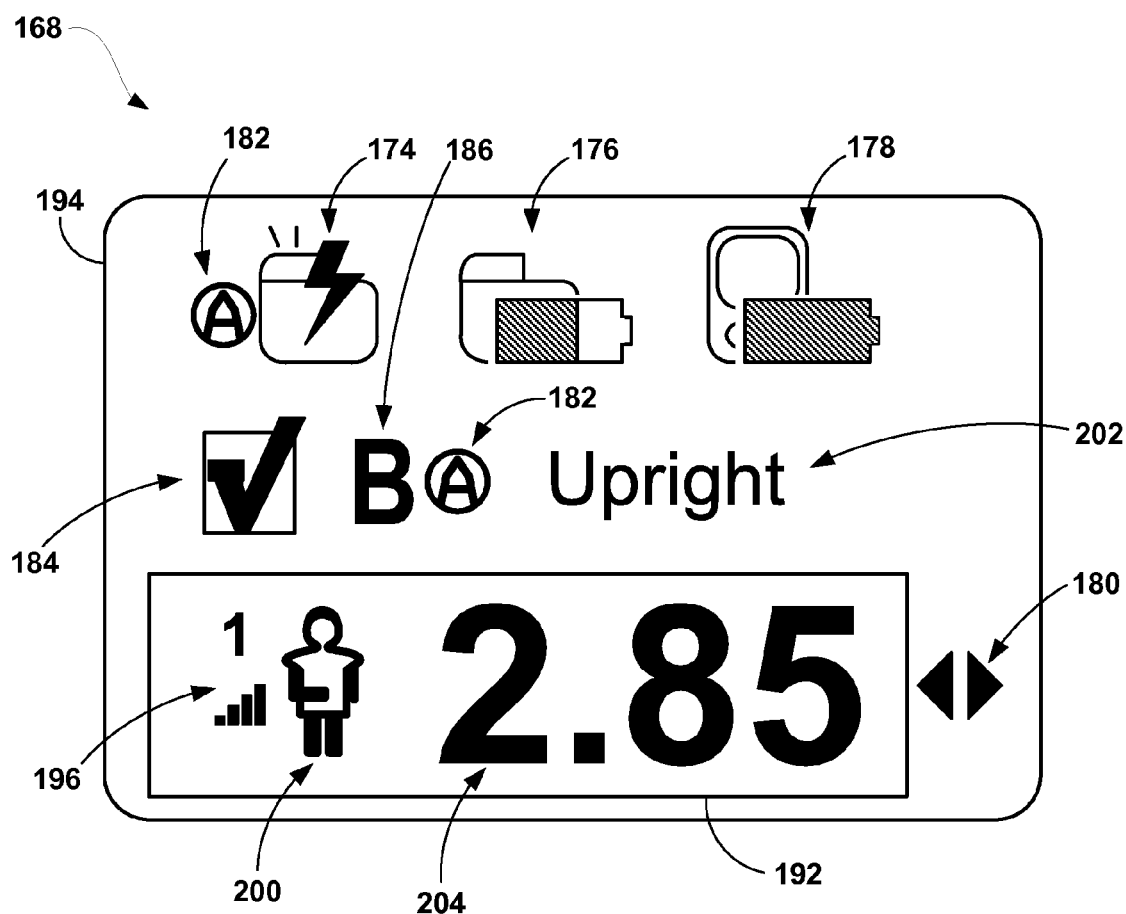
FIG. 10 is a conceptual diagram illustrating an example user interface of a patient programmer for delivering therapy information that includes posture information to the patient.

FIG. 10 is a conceptual diagram illustrating an example user interface 168 of a patient programmer, such as, e.g., patient programmer 30 (FIG. 2), for delivering therapy information that includes posture information to the patient. In other examples, user interface 168 may be presented by a clinician programmer (e.g., clinician programmer 60 of FIG. 3). In the example of FIG. 10, display 36 of patient programmer 30 provides user interface 168 to the user, such as patient 12, via screen 194. Screen 194 includes stimulation icon 174, IMD battery icon 176, programmer battery icon 178, and automatic posture response icon 182, similar to screen 170 of FIG. 9. In addition, screen 194 includes group selection icon 184, group identifier 186, supplementary posture state indication 202, program identifier 196, posture state indication 200, amplitude value 204, selection box 192, and selection arrows 180. User interface 168 provides information to patient 12 regarding therapy group, therapy program, amplitude, automatic posture response status, and posture state information. More or less information may be provided to patient 12, as desired by the clinician or the patient.

Group identifier 186 and group selection icon indicate that group "B" is currently selected for delivery to patient 12, and automatic posture response icon 182 proximate to group identifier 186 indicates group "B" (containing one or more therapy programs) is activated to allow IMD 14 to automatically deliver therapy according to the detected posture state of patient 12. In the example shown in FIG. 10, user interface 168 indicates the posture state of patient 12 detected by IMD 14, e.g., via posture state indication 200 and supplementary posture state indication 202. Program identifier 196 illustrates that information regarding program "1" of group "B" is displayed on screen 194, such as amplitude value 204 illustrating the current voltage amplitude of program "1" is 2.85 Volts. Patient 12 may scroll through different programs of the group by using navigation arrows 180 via arrows 44 and 48 of control pad 40.

In addition, posture state indication 200 shows that IMD 14 is detecting that patient 12 is in the upright or standing posture based on the output of posture state module 86 (FIG. 4). Supplementary posture state indication 202 supplements posture state indication 200 by explaining in words to patient 12 the exact posture being detected by posture state module 86 of IMD 14. Posture state indication 200 and supplementary posture state indication 202 presented via user interface 168 change according to the posture state of patient 12 detected by IMD 14. The posture state may be communicated to the external programmer immediately after IMD 14 detects a posture change, or communicated periodically or non-periodically by IMD 14 unilaterally or upon receiving a request from the programmer. Accordingly, the posture state indication 200 and/or supplementary posture state indication 202 may represent a current, up-to-the minute status, or a status as of the most recent communication of posture state from IMD 14. Posture state indication 200 is shown as a graphical representation, but the posture state indication may alternatively be presented as any one of a symbolic icon, a word, a letter, a number, an arrow, or any other representation of the posture state. In some cases, posture state indication 200 may be presented without supplementary posture state indication 202.

Selection box 192 indicates that patient 12 may view other programs within group "B" using selection arrows 180. Selection box 192 may be moved to select other screen levels with control pad 40 (FIG. 2) of patient programmer 30 in order to navigate through other stimulation groups or adjustable elements of the therapy. When patient 12 selects a different program with control pad 40, program identifier 196 is updated to correctly identify the current program viewed on screen 194.

In addition to graphical, textual or other visible indications of posture state, the external programmer may present audible and/or tactile indications of posture state via any of a variety of audible or tactile output media. An audible indication may be spoken words stating a posture state, or different audible tones, different numbers of tones, or other audible information generated by the programmer to indicate posture state. A tactile indication may be, for example, a somatosensory indication, such as different numbers of vibratory pulses delivered in sequence or vibratory pulses of different lengths, amplitudes, or frequencies.

The operation status of stimulation groups may vary on a group by group basis. For example, the delivery of stimulation therapy from IMD 14 based on the detected posture state of patient 12 may be activated on a group by group basis. In such examples, while IMD 14 may be generally activated to automatically adjust therapy to patient 12 based on the posture state detected by posture module 86, IMD 14 may only automatically adjust stimulation therapy in such a manner for groups that are activated. Accordingly, an external device, such as programmer 30 (FIG. 2) may present the operation status to a user, such as patient 12, on a group by group basis, including, e.g., a program by program basis, where a group comprises one or more therapy program, and each therapy program comprises a set of therapy parameters for delivery of a therapy program.

For example, as noted, screen 194 includes automatic posture response icon 182 proximate to group identifier 186. Such a configuration indicates that group "B" is activated, i.e., active, to allow IMD 14 to automatically deliver stimulation therapy according to the posture state of patient 12, as detected by IMD 14. Conversely, screen 170 of FIG. 9 fails to include an automatic posture response icon 182 proximate to group identifier 186. Such a configuration indicates that group "B" is not activated, i.e., inactive, to allow IMD 14 to automatically deliver stimulation therapy according to the posture state of patient 12, as detected by IMD 14. In this manner, user interface 168 may present the status of one or more groups to a user, such as patient 12, with respect to whether they are active or inactive for automatic adjustments to stimulation therapy according to the detected patient posture state.

Figure 11A:
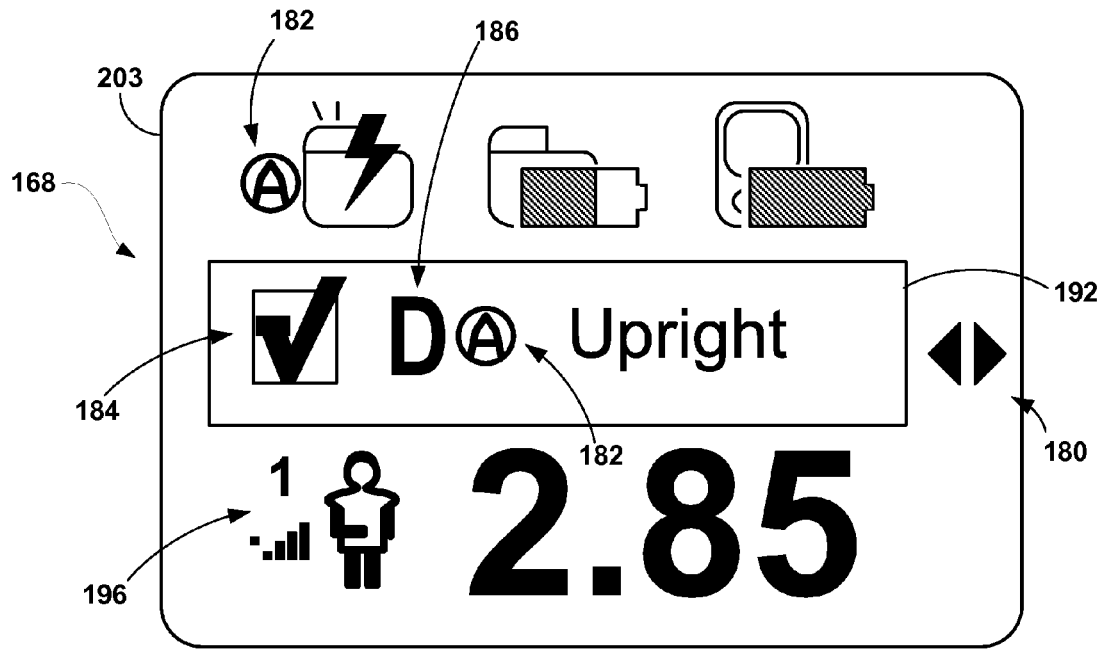
FIGS. 11A-11C are conceptual diagrams illustrating example user interfaces of a patient programmer for presenting therapy information the patient.
Figure 11B:
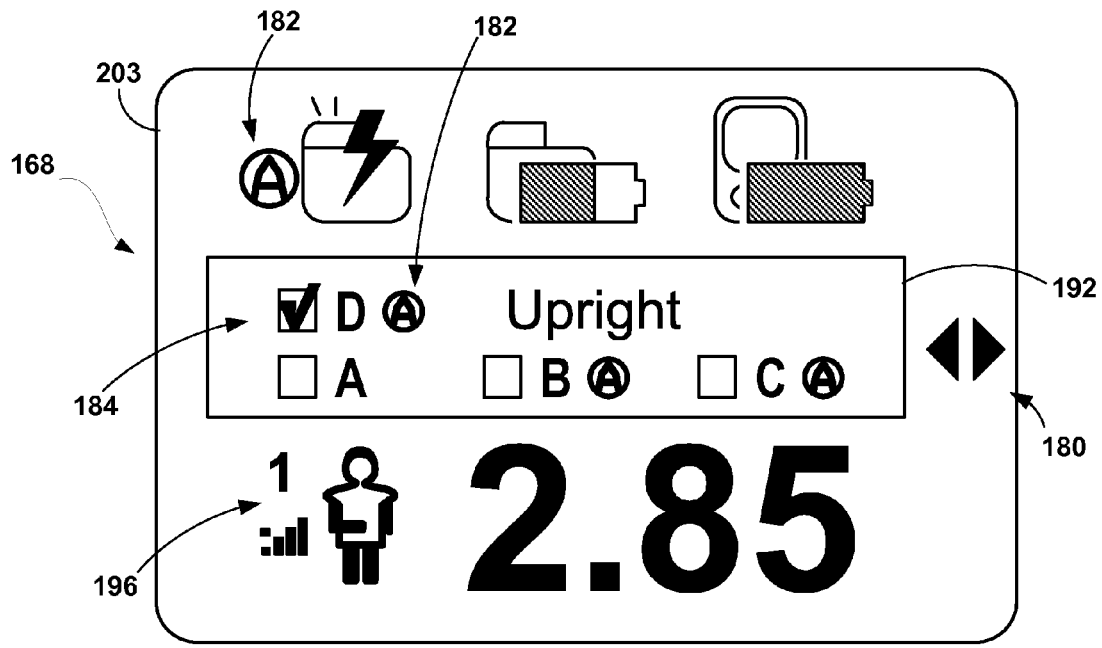
Figure 11C:
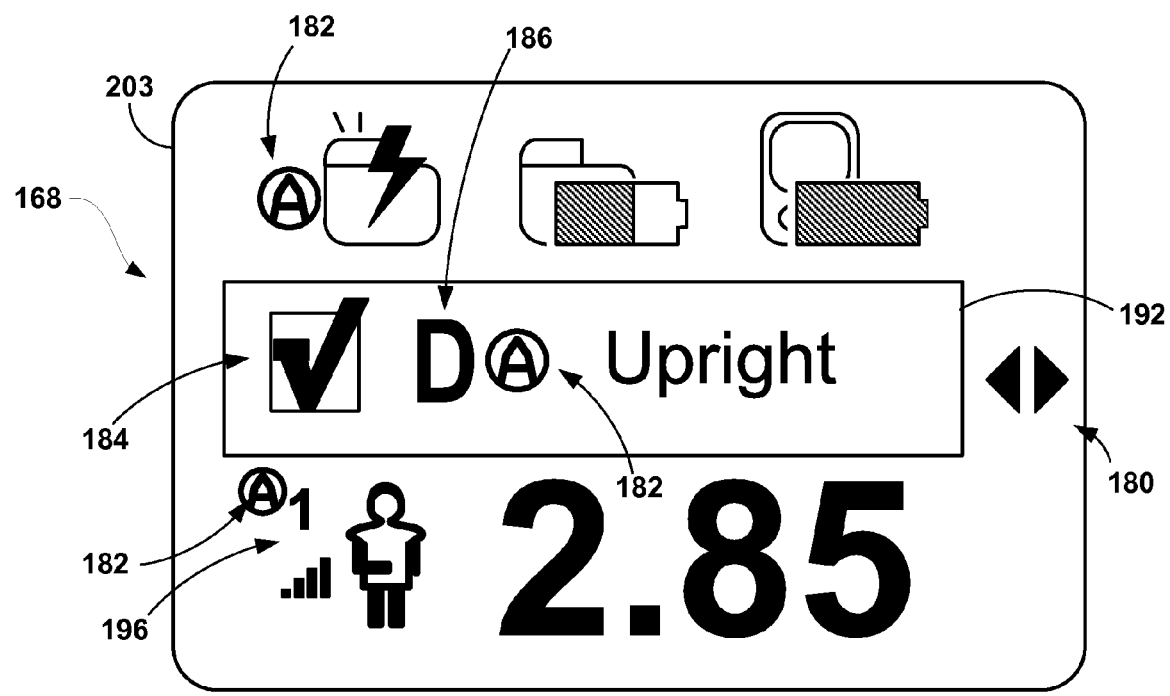

FIGS. 11A-11C are conceptual diagrams illustrating example user interfaces of a patient programmer for presenting therapy information the patient. In some examples, user interface 168 may selectively display groups depending on whether individual groups are active or inactive. FIG. 11A is a conceptual diagram illustrating an example user interface 168 of a patient programmer 30 for presenting therapy information to a patient. Similar to screen 194 of FIG. 10, screen 203 includes automatic posture response icon 182 proximate to group identifier 186. In this example, such a configuration indicates that group "D" is activated to allow IMD 14 to automatically deliver stimulation therapy according to the posture state of patient 12 detected by IMD 14.

Patient 12 may navigate to screen 203 from screen 194 (FIG. 10) using selection box 192 and navigation arrows 180. Notably, the user interface transitions directly from screen 194 (FIG. 10) to screen 203 based on the fact that the current status of group "C" is inactive for posture-responsive therapy in this example. Although respective groups typically may be presented in alphabetical order, user interface 168 may be configured to display to patient 12 only groups that are activated for posture-responsive therapy and hide those groups that are inactive for posture-responsive therapy. If the user has generally activated posture-responsive therapy for IMD 14, and if groups A and D are active for posture-responsive therapy, for example, user interface 168 may permit the user to view only groups A and D by transition via navigation arrows 180. Alternatively, if groups A and D are active for posture-responsive therapy, user interface may show groups A and D in bold or colored text and show inactive groups B and C in lighter text.

In this manner, user interface 168 may indicate to patient 12 which groups are active and which groups are inactive with respect to automatically delivering stimulation therapy according to the posture state of patient 12 detected by IMD 14. If the user has not generally activated posture-responsive therapy, or turned posture-responsive therapy off, the user interface may present all groups in a normal manner, without hiding any of the groups.

Any of a variety of techniques for presenting patient 12 with information concerning the status of individual groups with respect to whether a group is activated to be automatically delivered based on the posture state of patient 12 detected by IMD 14 may be used. Accordingly, the particular example described with reference to FIG. 11A is provided for purposes of illustration and without limitation to other approaches or techniques.

For example, as shown in FIG. 11B, user interface 168 may present all defined therapy groups, or at least a plurality of therapy groups, and the corresponding status of each group on a single screen to patient 12, e.g., in the form of a checklist or the like, rather than presenting the groups on an individual basis, e.g., by presenting the groups one at a time on a single screen to patient 12. In the example of FIG. 11B, groups A, B, C and D are presented via user interface 168. However, only group D includes a checkmark in group selection icon 184 to indicate that group D is selected for therapy delivery to patient 12 from IMD 14. In addition, the automatic posture response icon 182 is shown next to groups B, C and D, but not A, to indicate to patient 12 that groups B, C and D are activated for automatic posture-responsive therapy. In particular, when one of groups B, C, and D is selected for delivery of therapy to patient 12 as indicated by the checkmark, the active group is also active for automatic posture-responsive therapy. If group A is selected for delivery of therapy to patient 12, however, it supports manual adjustment of therapy but is not activated for automatic posture-responsive therapy.

In another example, user interface 168 may present all therapy groups active for posture-responsive therapy on a single screen along with an indication that all the displayed groups are currently active for posture-responsive therapy. In such a case, the non-displayed groups are then considered inactive for posture-responsive therapy. In other examples, a similar technique may be used to present all therapy groups inactive for posture responsive therapy on a single screen. In each case, the user may readily identify groups that are active and inactive for posture-responsive therapy. In some implementations, the user may be permitted to selectively activate and deactivate the displayed groups for posture-responsive therapy via such a screen, e.g., by checking or unchecking boxes next to particular group identifiers or by highlighting or dimming particular group identifiers, as desired.

To accurately display the status of respective groups with regard to posture-responsive therapy, programmer 30 may determine the operational status of individual groups by interrogating IMD 14. For example, programmer 30 may obtain therapy information from IMD 14 including which groups are currently active and which groups are currently inactive for delivery of therapy based on the detected posture state of patient 12 via a telemetry circuit, such as telemetry circuit 110 (FIG. 6). Programmer 30 may store such information in a memory, such as memory 108 shown in FIG. 6. Programmer 30 may then present the information to patient 12, e.g., via user interface 168.

Although the presentation of the status of groups with respect to whether an individual group is active or inactive for the adjustment of stimulation therapy according to the detected posture state of patient 12 is described with respect to patient programmer 30, it is recognized that in some examples, the same or similar information may be presented via clinician programmer 60 (FIG. 3) using one more techniques such as those described. In addition, such information may be presented via other devices such as programming or viewing devices coupled to receive such information from a programmer via a network.

Again, each group includes one or more therapy programs that may be delivered simultaneously, or on a time-interleaved basis, or in other orders. Group identifier 186 identifies the respective group and the presence of automatic posture response icon 182 proximate to group identifier 186 indicates that at least some of the programs in the group indicated by group identifier 186 are activate for automatic posture-responsive therapy. However, in some cases, a user such as a clinician or patient 12 may be permitted to selectively activate or deactivate individual programs of a particular group for posture-responsive therapy. In this case, if at least one therapy program in a group is activated for posture-responsive therapy, then automatic posture response icon 182 (or another indicator) may be presented, e.g., proximate to group identifier 186, to indicate that the group is activated for posture-responsive therapy. In some implementations, the programmer may permit a user to view the posture-responsive therapy status of individual programs within a group via a user interface, e.g., in substantially the same or similar manner previously described with regard to respective groups.

For example, each therapy program (e.g., numbered 1, 2, 3, etc.) may be selectively displayed on an individual basis or with one or more other therapy programs in a group. In this case, each therapy program may be identified by an automatic posture response icon 182 or some other indicator as being either inactive or active for posture-responsive therapy. As shown in FIG. 11C, for example, an automatic posture response icon 182 may be display adjacent to program identifier 196. When a given program is activated for automatic posture-responsive therapy, IMD 14 may make automatic therapy parameter values adjustments to the program based on a detected posture state of patient 12, even though automatic posture-responsive therapy may be deactivated for other programs in the group. Alternatively, all therapy programs in a group may be either activated or deactivated together for automated posture-responsive therapy. As previously described, a therapy group may include one or more therapy programs. In some cases, a therapy group may include only a single program. Presenting the operational status of a therapy group may include presenting the operational status of a single program, or a plurality of individual programs, which may each be considered groups, on a program by program basis.

Figure 12:
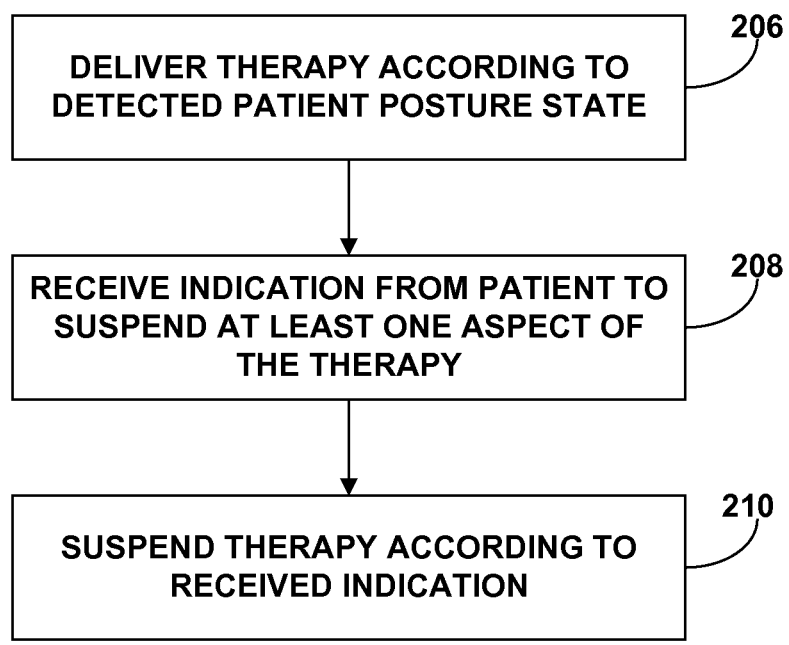
FIG. 12 is a flowchart illustrating an example technique for suspending one or more aspects of therapy being delivered to a patient.

FIG. 12 is a flowchart illustrating an example technique for suspending one or more aspects of therapy being delivered to a patient. IMD 14 may be configured to utilize such a technique when delivering electrical stimulation therapy to patient 12 based on the detected posture state of patient 12. In some situations, it may be desirable to allow a patient that is receiving stimulation therapy according to their detected posture state to suspend one or more aspects of the stimulation therapy. For example, patient 12 may wish to suspend posture-responsive therapy voluntarily when patient 12 expects to participate in an activity that could result in spurious posture state detections or the detection of frequent posture state transitions by posture state module 86. In such cases, a technique such as that shown in FIG. 12 may be used to suspend the delivery of stimulation according to the posture state detected by IMD 14.

As indicated by the example of FIG. 12, IMD 14 may deliver stimulation therapy according to the posture state of patient 12 detected by IMD 14 (206). As previously described, IMD 14 may detect the posture state of patient 12 via posture state module 86 and automatically adjust the value of one or more parameters of the stimulation, such as amplitude, pulse width, pulse rate, and/or electrode combinations, according to the detected posture state. In some examples, posture state module 86 includes one or more accelerometers and detects the posture state of patient 12 using posture state information derived from the signals generated by the one or more accelerometers. For example, as previously described, posture state information including activity data may be derived from the AC component of a signal generated by an accelerometer, which yields information describing the motion of patient 12 based in part on the acceleration of patient 12. Using the motion information, posture state module 86 may detect the posture state of patient 12 and IMD 14 may adjust stimulation according to the detected posture state. As one example, an activity count may be derived from the AC component of the accelerometer signal(s), which may be used to generate an accurate indication of motion of patient 12.

However, in some cases, patient 12 may engage in an activity which could cause posture state module 86 to inaccurately determine the posture state of patient 12, e.g., as a result of the inaccurate determination of the activity data of patient by posture state module 86. For example, patient 12 may engage in activity in which the one or more accelerometers used by posture state module 86 to detect patient motion sense motion that is not a result of actual patient generated activity but instead is due to the external environment of patient 12. As one example, patient 12 may be riding in an automobile at times during the course of his or her day. When riding in the automobile, posture state module 86 may sense periods of acceleration and deceleration based on the output signals of accelerometers, which result from the normal operation of the vehicle and not from actual patient generated activity. As other examples of patient activity that may cause posture state module 86 to inaccurately determine activity of patient 12, patient 12 may ride on an airplane, rollercoaster, train, moving walkway, or the like. In general, these activities may cause patient 12 to accelerate in one or more directions although the acceleration is not a direct result of patient generated activity.

However, posture state module 86 may sense the non-patient generated acceleration and inaccurately detect the posture state of patient 12. As one example, when a patient engages in such activities, the activity count of patient 12 derived from the accelerometer signal(s) may inaccurately indicate the motion of patient 12 and the posture state of patient 12 in general, at least to the extent that the activity count reflects patient motion that should not result in an adjustment to stimulation therapy being delivered to patient 12. For example, the stimulation therapy delivered to patient 12 when sitting in a chair that is stationary and not moving compared to stimulation delivered to patient 12 when sitting in a chair that is moving, e.g., the seat of a car while the car is moving, should be substantially the same. However, for at least these reasons identified, posture state module 86 may detect that patient 12 is occupying a different posture state in each case due to motion from the movement of the car. For example, activity module 86 may detect that patient 12 is in an "Upright and Active" posture state while sitting in a car while the car is moving, while activity module 86 may detect that patient 12 is in an "Upright" posture state while sitting in a chair that is not moving. As a result, IMD 14 may deliver different stimulation therapy to patient 12 in each situation, despite the fact that patient 12 is actually in roughly the same posture state in both situations.

Referring still to FIG. 12, while IMD 14 is delivering stimulation therapy to patient 12 according to the detected posture state of patient 12 (206), IMD 14 may receive an indication from patient 12 to suspend at least one aspect of the stimulation therapy (208). Upon receiving the indication, IMD 14 may suspend delivery of the stimulation therapy according to the indication received from patient 12 (210). In this manner, the delivery of stimulation to patient 12 may be suspended in situations in which posture state module 86 may be inaccurately detecting the posture state of patient 12, such as when patient 12 engages in activities that could produce misleading accelerometer signal output, such as those activities described above.

The nature of the suspension of stimulation therapy may vary. In some example, IMD 14 may be configured to automatically suspend the delivery of all stimulation therapy to patient 12, including delivery of stimulation therapy that is not based on the detected posture state of patient 12, i.e., stimulation that is not activated for posture-responsive therapy. In other examples, however, IMD 14 may be configured to automatically suspend the delivery of stimulation therapy according to the posture state of patient 12 detected via posture state module 86 and, instead, deliver stimulation according to one or more stimulation therapy programs that are not activated for posture-responsive therapy but rather are delivered by IMD 14 without regard to the detected posture state of patient 12.

In other words, groups or programs that are activated for posture-responsive therapy may be suspended by deactivating them entirely, in which case IMD 14 may deliver therapy to patient 12 according to non-posture-responsive program or groups, or by deactivating the posture-responsive therapy aspect of therapy programs or groups that were active for posture-responsive therapy when the suspension indication was received such that the therapy programs or groups are not posture-responsive during the suspension. Hence, according to the first scenario, if groups A and C are activated for posture-responsive therapy and groups B and D are not, then suspension may result in delivery of therapy according to either group B or D, but not group A or C. Alternatively, according to the second scenario, the suspension may result in deactivation of posture-responsive therapy for groups A and C, such that any of groups A, B, C or D may be delivered on a non-posture-responsive basis.

In the above examples, posture-responsive therapy for one or more stimulation therapy groups may be deactivated such that the therapy groups are not activated to allow IMD 14 to automatically deliver therapy to patient 12 according to the posture state of patient 12 detected via posture state module 86, but can still be delivered on a non-posture-responsive basis. Alternatively, therapy groups supporting posture-responsive therapy may be deactivated entirely. In other examples, IMD 14 may be configured to continue delivering stimulation therapy according to parameter values at the time that the suspension indication was received, or revert to a particular set of parameter values specified for delivery to patient 12 during a suspension period. In some examples, IMD 14 may be configured to suspend the actual detection of the posture state of patient 12 by posture module 86 entirely when patient 12 indicates that posture-responsive therapy should be suspended, e.g., by "turning off" the posture state sensor(s) when stimulation therapy is suspended. In such examples, rather than detecting the posture state of patient 12 but not delivering stimulation according to the posture state of patient 12 detected via posture state module 86, IMD 14 may simply suspend the detection of posture state of patient 12. In each case, the duration of the suspension may be temporary or permanent, subject to removal of the suspension by a user such as patient 12 or clinician.

For a temporary suspension, the suspension may remain in effect for a predetermined period of time or a period of time specified by the user. In this case, posture-responsive therapy may be automatically reactivated upon expiration of the period of time, e.g., tracked internally within IMD 14 or upon transmission of a command from a programmer (e.g., programmer 30 (FIG. 2)) to IMD 14. Alternatively, the programmer may present a message to a user, upon expiration of the time period, advising that posture-responsive therapy will be reactivated within n seconds or minutes if the user does not indicate otherwise. As a further alternative, upon expiration of the time period, the programmer may present a message to seek explicit approval from the user for reactivation of the posture-responsive therapy. In other cases, suspension may be permanent and require the user to reactivate posture-responsive therapy when desired.

In some examples, in cases when posture state module 86 may be inaccurately detecting the activity of patient 12, e.g., because of misleading activity counts, IMD 14 may be configured to suspend delivery of stimulation therapy for posture states that are based at least in part on the activity count of patient 12. For example, IMD 14 may suspend posture-responsive therapy for upright and active posture state, but maintain posture-responsive therapy for other posture states that do not rely on the level of patient activity as part of the posture state definition. In this case, the parameter settings for the upright posture state or other parameter settings may be used for the upright and active posture state, if an upright and active posture state is detected by posture state module 86.

Also, in some examples, upon receiving a suspension indication, posture state module 86 may be configured to detect the posture state as usual except that it may ignore the activity count derived from the accelerometer signals. For example, posture state module 86 may override the derived activity count parameter with a relatively low or medium activity count value or be programmed to classify the posture state of patient 12 without taking into account the activity count derived from the accelerometer signal. In any case, IMD 14 may continue to deliver stimulation therapy based on the detected posture state of patient 12, but it will not take into account the sensed activity of patient 12, e.g., as indicated by the derived activity count. For example, in such cases, while IMD 14 may detect when patient 12 is "Upright" verses "Lying" and adjust therapy accordingly, IMD 14 will not distinguish between "Upright" and "Upright and Active" for the purposes of adjusting therapy.

In some cases, IMD 14 may be preprogrammed to suspend therapy, e.g., in one or more of the ways described, any time patient 12 generally indicates that the therapy should be suspended. In other cases, patient 12 may be allowed to specify the nature of the suspension in therapy. As part of the therapy suspension indication, patient 12 may indicate the nature of the stimulation therapy suspension. For example, patient 12 may indicate that adjustments to stimulation therapy based on the detected posture state should be suspended but that delivery of stimulation therapy should be maintained at the level currently being provided by IMD 14 to patient 12. Patient 12 may specify such an action after patient 12 sits in an automobile, for example, but prior to the automobile moving. The scope of the suspension also may be defined at least in part by a clinician when programming the IMD.

Hence, the scope of the suspension of posture-responsive therapy may be selectively configurable by the clinician, patient or other user. The scope of the therapy suspension may refer to the particular functions that are suspended and the manner in which suspension is performed. Again, the scope of the suspension may include a range of configuration parameters relating to how posture-responsive therapy is deactivated including, without limitation, deactivating all groups that support posture-responsive therapy, deactivating posture-responsive functionality of such groups without deactivating the groups per se, temporarily or permanently suspending posture-responsive stimulation, reactivating stimulation subject to a timer and/or user approval, deactivating activity-based posture states but keeping other posture-responsive therapy for other posture states intact, and so forth.

Patient 12 may be allowed to indicate to IMD 14 that stimulation therapy should be suspended via an external device, such as, e.g., patient programmer 30. For example, patient 12 may indicate to programmer 30 that one or more aspects of the stimulation therapy should be suspended. Upon receiving the patient input, programmer 30 may generate an indication according to the patient input and then send the indication to IMD 14 via a telemetry circuit, such as telemetry circuit 110 of FIG. 6. Upon receipt of the indication from programmer 30, IMD 14 may suspend the stimulation according to the indication.

As described with respect to FIG. 12, programmer 30 may be configured to allow patient 12 to manage and program stimulation therapy. The management of stimulation therapy may include the ability to suspend one or more aspects of the stimulation therapy as previously described herein. For example, patient 12 may be able to indicate to IMD 14 via programmer 30 that the adjustment of stimulation therapy according to the posture state of patient 12 detected by posture state module 86 should be suspended.

Referring to FIG. 12, patient 12 may be able to suspend one or more aspects of stimulation therapy delivered by IMD 14 using programmer 30. In some examples, patient 12 may indicate to programmer 30 that they are about to undertake or are undertaking a behavior which may result in inaccurate detection of patient activity and, more generally, patient posture state. For example, patient 12 may indicate to programmer 30 that patient 12 is about to ride in a car or airplane by navigating through one or more items displayed on display 36 using one or more of control pad 40 and buttons 50, 52, 54, 56, and 58. In some examples, programmer 30 may present a list to patient 12 including a list of undertakings (e.g., riding in the car, on a plane, and the like) and, based on the patient's selection from the list, system 10 may automatically suspend one or more aspects of the stimulation therapy associated with the selected undertaking. Such a list may be presented by programmer 30 via a drop down menu. In some examples, the list may be populated on a patient-by-patient basis to take into account those undertakings specific to the patient, and a user (e.g., a clinician or patient) may form the associations between the undertaking and the aspects of therapy to suspend for the particular undertaking.

In some cases, rather than indicating that they are about to undertake or are undertaking a certain behavior or activity, the patient may simply indicate that one or more aspects of the stimulation should be suspended. Again, patient 12 may indicate such information to programmer 30 by navigating through one or more items displayed on display 36 using one or more of control pad 40 and buttons 50, 52, 54, 56, and 58. In this manner, patient 12 may be allowed to suspend one or more aspects of the stimulation therapy being delivered by IMD 14 according to the posture state detected via posture state module 86 in situations in which posture state module 86 may inaccurately detect the posture state of patient 12.

In some examples, rather than requiring patient 12 to navigate through one or more screens on display 36, programmer 30 may include one or more individual buttons, such as buttons 54, 56, and/or 58, configured such that patient may quickly and easily suspend one or more aspects of stimulation therapy by depressing the button. For example, programmer 30 may be configured such that when patient 12 depresses button 56, IMD 14 automatically suspends one or more aspects of the stimulation therapy being delivered. In this manner, patient 12 may suspend stimulation therapy by depressing a single button on programmer 30. As another example, in order to ensure that patient 12 does not accidentally suspend stimulation therapy, programmer 30 may be configured to display a prompt screen on display 36 prompting patient 12 to confirm that they indeed wish to suspend stimulation therapy. In such cases, patient 12 may view button 56 as a "pause" button for the stimulation aspect it is configured to suspend. Accordingly, patient 12 may simply depress button 56 any time patient 12 wishes to suspend stimulation therapy, especially when patient 12 is about to undertake a behavior during which IMD 14 may inaccurately detect the posture state of patient 12 via posture state module 86, such as, e.g., the behaviors previously described. IMD 14 may save the therapy delivery parameters in conjunction with suspending one or more aspects of the stimulation, thereby allowing IMD 14 to resume therapy using to substantially the same therapy parameters.

Figure 13A:
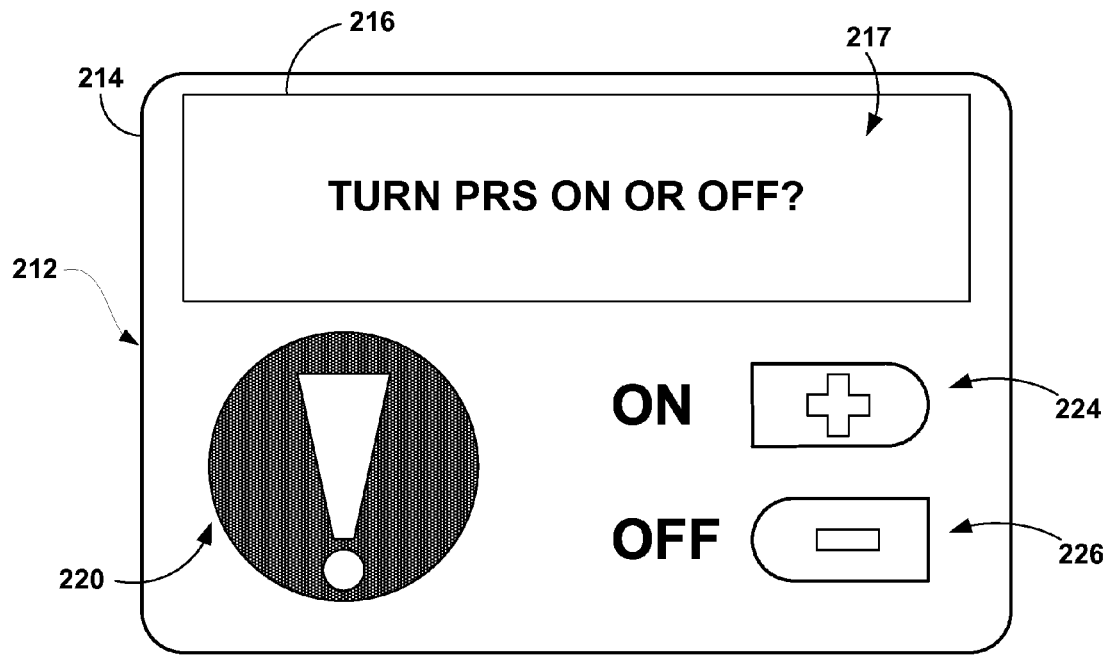
FIGS. 13A and 13B are conceptual diagrams illustrating an example screen of a user interface for prompting a user to turn posture-responsive therapy on or off or suspend posture-responsive therapy.
Figure 13B:
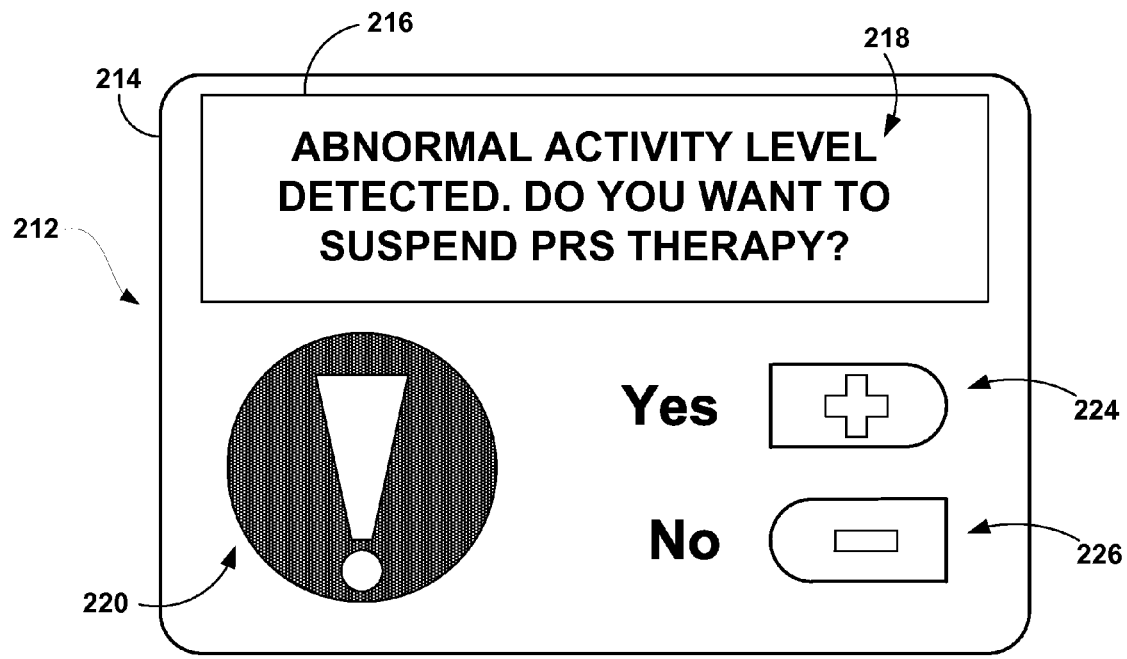

FIGS. 13A and 13B are conceptual diagrams illustrating an example screen of a user interface for prompting a user to turn posture-responsive therapy on or off or suspend posture-responsive therapy. FIG. 13A is a conceptual diagram illustrating an example screen 214 of user interface 212 for permitting a user, such as patient 12, to directly suspend stimulation therapy. As shown in FIG. 13A, screen 214 presents selection box 216, alert icon 220, prompt text 217, yes prompt 224 (shown as "on" prompt in FIG. 13A), and no prompt 226 (shown as "off" prompt in FIG. 13B). Screen 214 may be displayed to patient 12 when patient 12 navigates to a settings screen of the programmer, e.g., using directional arrows. Alternatively, as mentioned above, screen 214 may be presented when patient 12 depresses an external button such as button 56 (FIG. 2), as previously described.

Prompt text 217 seeks to confirm that patient 12 would like to proceed with suspension of posture-responsive therapy i.e., posture-responsive stimulation (PRS) in the example of FIG. 13A. In particular, text 217 prompts patient 12 to input whether or not patient 12 would like to suspend one or more therapy aspects, such as, e.g., stimulation therapy that is adjusted based on the posture state of patient 12 detected via posture state module 86. If patient 12 would like to suspend the therapy as prompted by text 217, patient 12 may confirm the proposed suspension of therapy by pressing increase button 52 as shown by yes prompt 224 (shown as "on" prompt in FIG. 13A). If patient 12 would not like to suspend the therapy as prompted by text 217, then patient 12 may select decrease button 50 as shown by no prompt 226 ("off" prompt in FIG. 13A).

Alternatively, patient 12 may use control pad 40 to highlight either yes (on) prompt 224 or no (off) prompt 226 with selection box 216. Whether patient 12 elects to maintain or suspend stimulation therapy, patient 12 may be presented with a screen confirming the patient action and then may be returned to a normal operating screen of the user interface. Upon receiving the patient input, programmer 30 may generate an indication to IMD 14 indicating the patient's wishes with respect to the suspension of stimulation therapy. IMD 14 may then proceed with stimulation therapy according to the generated indication. Any of a variety of techniques for presenting patient 12 with information and eliciting patient input concerning the suspension of one or more aspects of stimulation therapy may be used. Accordingly, the particular example provided in FIG. 13A is provided for purposes of illustration and without limitation to other approaches or techniques.

FIG. 13B is a conceptual diagram illustrating an example screen 214 of user interface 212 for prompting a user, e.g., patient 12, to suspend stimulation therapy. The user interface may be displayed on display 36 of programmer 30. As in the example of FIG. 13A, screen 214 in FIG. 13B presents selection box 216, alert icon 220, yes prompt 224, and no prompt 226. In addition, screen 214 presents prompt text 218. FIG. 13B is similar to FIG. 13A, but contemplates a situation in which IMD 14 is configured to automatically detect an abnormal activity that could result in misleading activity counts, e.g., via posture state module 86 and/or supplementary device, such as an external sensor, configured to automatically detect abnormal activity of patient 12. Upon detection of an abnormal event, IMD 14 may notify the external programmer via wireless telemetry, e.g., telemetry circuit 88 (FIG. 4).

Screen 214 may be automatically displayed to patient 12 when posture state module 86 of IMD 14 and/or a supplementary device, such as an external posture sensor worn by patient 12 or carried in or on a programmer or other device, detects an abnormal activity count based on an accelerometer signal, as previously described, and notifies the programmer. IMD 14 may be configured to generate an alert to programmer 30 when the detect activity count of patient 12 is above a preprogrammed threshold level. For example, this threshold limit may correspond to an activity count value or pattern that is not typically achievable by patient 12, only achievable by patient 12 when undertaking extreme physical activity, or otherwise indicative of an abnormal situation such as riding in a car, airplane, amusement ride or the like. In some examples, the threshold level may be set by patient 12 or a clinician based on patient specific factors, which may relate to lifestyle and likely activity levels for the patient, given the patient's own physical condition and interests.

Instead of suspending an amplitude change based on the posture that is detected, i.e., upon detecting the posture state, because automated therapy is suspended, the actual posture state detection itself could be suspended. In other words, the posture sensor may, in effect, be turned off for a period of time until posture detection is resumed after patient 12 presses a button or a timer expires, or posture detection is otherwise resumed in some other manner. Hence, in this case, posture detection may be suspended instead of, or in addition to, suspension of stimulation. As shown in FIGS. 13A and 13B, alert icon 220 alerts patient 12 that IMD 14 has detected a circumstance that requires patient 12 input. Programmer 30 may also alert patient 12 via one or more audible or tactile alerts. In the example shown in FIG. 13B, prompt text 218 indicates to patient 12 that IMD 14 has detected an abnormal activity level. Further, text 218 prompts patient 12 to input whether or not they would like to suspend one or more stimulation therapy aspects, such as, e.g., stimulation therapy adjusted based on the posture state of patient 12 detected by posture state module 86. In other examples, programmer 30 may directly suggest to patient 12 that posture-responsive therapy, or one or more aspects thereof, should be suspended based on the detection of abnormal activity levels. For example, programmer 30 may communicate a textual message to that effect to patient 12 via display 36.

If patient 12 would like to suspend the stimulation therapy as prompted by text 218, patient 12 may confirm the proposed suspension of therapy by pressing increase button 52 as shown by yes prompt 224. If patient 12 would not like to suspend the therapy as prompted by text 218, then patient 12 may select decrease button 50 as shown by no prompt 226. Alternatively, patient 12 may use control pad 40 to highlight either yes prompt 224 or no prompt 226 with selection box 216.

Whether patient 12 elects to maintain or suspend stimulation therapy, patient 12 may be presented with a screen confirming the patient action and then may be returned to the normal operating screen of the user interface. Upon receiving the patient input, programmer 30 may generate an indication to IMD 14 indicating the patient's wishes with respect to the suspension of stimulation therapy. IMD 14 may then proceed with stimulation according to the generated indication. Again, any of a variety of techniques for presenting patient 12 with information and eliciting patient input concerning the suspension of one or more aspects of stimulation therapy may be used. Accordingly, the particular example provided in FIG. 13B is provided for purposes of illustration and without limitation to other approaches or techniques.

Examples of the disclosure are not limited only to patient-directed suspension of one or more aspects of stimulation therapy as described, but may also include clinician-directed suspension, as well as resumption of one or more aspects of the stimulation therapy that have been suspended pursuant to patient-directed or clinician-directed suspension. For example, as described previously, after patient 12 has ceased an activity that may cause posture state module 86 of IMD 14 to inaccurately detect the posture state of patient 12, patient 12 may indicate to IMD 14 via programmer 30 that patient 12 wishes to resume the one or more aspects of stimulation that were suspended, and thereby lift the suspension. Upon receiving such an indication, IMD 14 may resume the suspended aspects of stimulation. For example, IMD 14 may resume detecting patient posture state and adjusting the stimulation being delivered to patient 12 according to the detected posture state via posture state module 86, in the manner that was used up until approximately the point in time the stimulation therapy was suspended.

Patient 12 may indicate that suspended stimulation therapy should be resumed using the same or similar approach that was used to suspend the stimulation therapy. For example, as described with respect to programmer 30, patient 12 may depress button 56, which was used to "pause" the stimulation therapy, to resume the same stimulation therapy. In other cases, patient 12 may navigate to one or more screens on programmer 30 to indicate that they would like to resume the suspended stimulation therapy. Upon receiving the indication from patient 12, programmer 30 may generate an appropriate indication and send it to IMD 14. IMD 14 may then resume stimulation therapy in accord with the indication received from programmer 30.

In some examples, as mentioned previously, IMD 14 may automatically or semi-automatically (with user approval) resume suspended stimulation therapy (or resume suspended posture detection) after a preprogrammed period of time has elapsed. This time may be specified to be consistent with the amount of time that patient 12 is likely to generally engage in the activity that necessitated the suspension of the one or more aspects of stimulation therapy, e.g., a period greater than the average length of time of car ride. In some examples, after the specified period of time has elapsed, IMD 14 may automatically resume the suspended stimulation therapy.

In other examples, programmer 30 may automatically prompt patient 12 after a preset period of time to elicit patient input as to whether the suspended therapy (or suspended posture detection) should be resumed, e.g., similar to the example of FIG. 12. In another example, IMD 14 may be configured to resume or prompt patient 12 to resume suspended stimulation therapy (or suspended posture detection)

when IMD 14 no longer detects abnormal activity of patient 12, e.g., based on the activity count derived from the output signal(s) of one or more accelerometers associated with posture state module 86. In some cases, the detection of abnormal activity by IMD 14 may have triggered the suspension of the therapy initially.

In accordance with some examples of the disclosure, IMD 14 may be configured to resume stimulation therapy that has been turned off, i.e., stimulation therapy that has been deactivated in one form or another. In some examples, one or more stimulation therapy groups may be deactivated by patient 12 such that the respective groups are not activated to be delivered according to the detected posture state of patient 12. While it has been described that patient 12 may suspend and/or resume stimulation via programmer 30, in other examples, a clinician may be allowed to resume stimulation that has been deactivated by patient 12.

Figure 14:
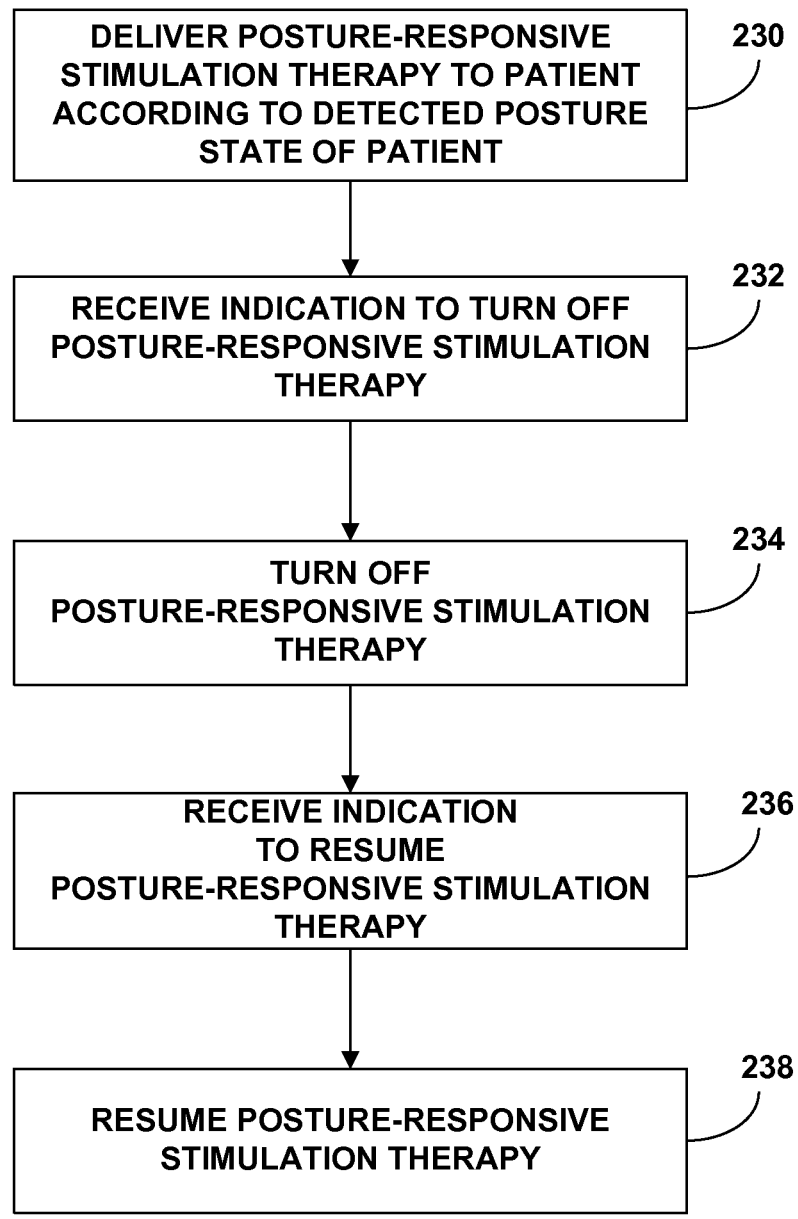
FIG. 14 is a flowchart illustrating an example technique for resuming stimulation therapy.

FIG. 14 is a flowchart illustrating an example technique for resuming stimulation therapy. Such a technique may be used by a clinician to resume stimulation that has been deactivated by patient 12 and may be incorporated into a therapy system including IMD 14 and clinician programmer 60. As indicated by FIG. 14, IMD 14 may deliver stimulation therapy to patient 12 according to the detected posture state of patient 12 (230). At some point, IMD 14 may receive an indication to turn off the stimulation therapy, e.g., via patient programmer 30 (232).

Patient 12 may wish to turn off stimulation therapy as such for one or more reasons. For example, patient 12 may be experiencing one or more negative side effects from the stimulation therapy being delivered by IMD 14. As another example, patient 12 may suspect and/or confirm that posture state module 86 of IMD 14 is inaccurately detecting the posture state occupied by patient, e.g., because one or more accelerometers has become disoriented as a result of physical movement of the accelerometer with respect to patient 12. Also, patient 12 may be anticipating engaging in some undertaking for which it is desirable to disable one or more aspects of posture-response therapy. Accordingly, the stimulation therapy being delivered to patient 12 may not be appropriate for the posture state that patient 12 is actually occupying, or will be occupying in the future. In any case, IMD 14 may receive an indication from patient 12 that posture-responsive stimulation therapy should be turned off (232), e.g., via patient programmer 30 (FIG. 2).

Upon receipt of the indication that stimulation should be turned off, IMD 14 may turn off delivery of stimulation therapy to patient 12 based on detected posture state of patient 12 (234) or turn off the detection of patient posture state by posture state module 86. This may include IMD 14 globally deactivating the stimulation therapy groups such that they are not available for therapy delivery according to the detected posture state of patient 12. In some examples, IMD 14 may cease the delivery of all stimulation therapy to patient 12, including stimulation therapy not delivered according to the detected posture state of patient 12. Alternatively, only posture-responsive groups or posture-responsive aspects of groups may be turned off to deactivate posture-responsive stimulation therapy. Furthermore, similar to that previously described, in some examples, IMD 14 may cease the actual detection of the posture state of patient 12 by posture module 86.

Once IMD 14 has turned off stimulation therapy, e.g., due to inaccurate posture state detection, patient 12 may seek to remedy the situation by contacting a clinician. In other cases, a clinician may be automatically contacted when the stimulation therapy in turned off by patient 12, e.g., using a system such as that illustrated in FIG. 7. In any case, a clinician may be notified that the stimulation therapy has been turned off. In some cases, the clinician may also be informed of the reason that patient 12 turned off the stimulation.

The clinician may then investigate the alleged problem and determine what course of action to take. In some cases, this may take place during an in-person programming session with patient 12 to determine and correct the problem. For example, if it is believed that posture state module 86 is inaccurately determining the posture state of patient 12, the clinician may interrogate IMD 14 while patient 12 occupies a known posture state to determine whether the posture state that posture state module 86 is detecting is accurate or inaccurate.

If it is determined that posture state module 86 is inaccurately detecting patient posture state, e.g., because one or more accelerometers has physically changed position in patient 12, the clinician may then reorient the posture state module 86 such that posture state module 86 accurately detects the posture state of patient 12. In other examples, a clinician may be able to remotely interrogate the IMD 14 to perform substantially the same procedure from a remote location, e.g., using a system such as that shown in FIG. 7. Although the clinician may not be at the same physical location as patient 12, substantially the same process described above may be carried out to determine and correct any potential stimulation therapy problems.

IMD 14 may then receive an indication to resume that stimulation that was previously turned off (238). For example, a clinician may communicate to IMD 14 via programmer 60 that the deactivated posture-responsive stimulation therapy should be resumed. IMD 14 may then resume the stimulation therapy, e.g., by activating one or more groups or posture-responsive aspects of such groups. In examples in which IMD 14 has ceased detecting the actual posture state of patient 12, IMD 14 may resume detecting the actual posture state of patient 12 via posture state module 86.

Notably, the configuration of the stimulation delivered by IMD 14 once posture-responsive stimulation therapy (or posture detection) is resumed may vary depending on one or more factors. IMD 14 may resume delivery of therapy based on therapy information in one form or another. In some examples, IMD 14 may resume delivering stimulation therapy according to the stimulation therapy as configured at approximately the time the stimulation was turned off. For example, IMD 14 may activate only the therapy groups that were active at the time the stimulation therapy was turned off. This therapy information may be stored in memory 82 of IMD 14 at approximately the time of the stimulation is turned off and then obtained by IMD 14 if the stimulation therapy is to be resumed as configured as it was at approximately the time of it was turned off. In such cases, the stimulation therapy is in effect "paused" when turned off such that resuming the stimulation therapy as directed by the clinician effectively ends the "pause" in stimulation therapy. In some examples, the therapy information may include therapy information associated with the posture state of patient 12 detected at the time the therapy is resumed. Accordingly, when IMD 14 resumes therapy, the therapy may be delivered according to the therapy information associated with the posture state occupied by patient 12. In other examples, the therapy information does not include therapy information associated with the posture state detected at the time the therapy is resumed.

In other examples, rather than resuming the stimulation therapy according to the stimulation as configured at the time stimulation was turned off, IMD 14 may effectively restart the stimulation therapy at a default configuration, such as the initial start-up therapy configuration of IMD 14 after being implanted in patient 12. This initial start-up therapy information may also be stored in memory 82 of IMD 14. In such cases, other therapy information received since the implantation of IMD 14 such as patient specific modifications to the initial stimulation therapy configuration may be disregarded and, optionally, erased from memory 82 of IMD 14. In effect, such an approach may be regarded as restarting the stimulation therapy configuration rather than ending a "pause" in the stimulation therapy as described above.

In other examples, stimulation therapy configurations may be periodically defined and stored in memory 82 of IMD 14. When stimulation therapy is resumed by IMD 14, IMD 14 may revert back to the therapy configuration of one of these previously defined stimulation therapy configurations. For example, IMD 14 may revert to the most recently saved stimulation therapy configuration before IMD 14 turned off the stimulation therapy. Alternatively, IMD 14 may revert to a therapy configuration saved prior to patient 12 experiencing one or more issues that may have led patient 12 to turn off the therapy in the first place. In any case, this type of therapy information may be stored in memory 82 accessed by IMD 14 to resume the stimulation therapy.

In some examples, the clinician may be allowed to indicate to IMD 14 via programmer 60 the therapy configuration in which IMD 14 should resume stimulation therapy. For example, along with the indication to resume stimulation therapy, the clinician may also indicate in what configuration IMD 14 should resume the stimulation therapy. IMD 14 may then access the appropriate stored therapy information consistent with the therapy configuration indication received from programmer 60. Alternatively, or additionally, IMD 14 may be preprogrammed to resume stimulation in a preselected therapy configuration. In such cases, whenever IMD 14 resumes stimulation that has been turned off, IMD 14 may do so according to the therapy information consistent with the preselected therapy configuration.

As previously described, in some examples, IMD 14 may be configured to automatically adjust at least one aspect of posture-responsive therapy being delivered to a patient based at least in part on time, e.g., time of day, and/or patient posture state behavior. In particular, an IMD 14 may automatically adjust the posture responsive therapy by suspending one or more aspects of posture-responsive therapy or adjusting the posture state detection frequency, e.g. decreasing posture state detection frequency, based at least in part on time and/or patient posture state behavior. In some examples, by automatically adjusting one or more aspects of posture-responsive therapy in such a manner, an IMD 14 may reduce or minimize the amount of power consumed while maintaining efficacious delivery of therapy to patient 12.

Figure 15:
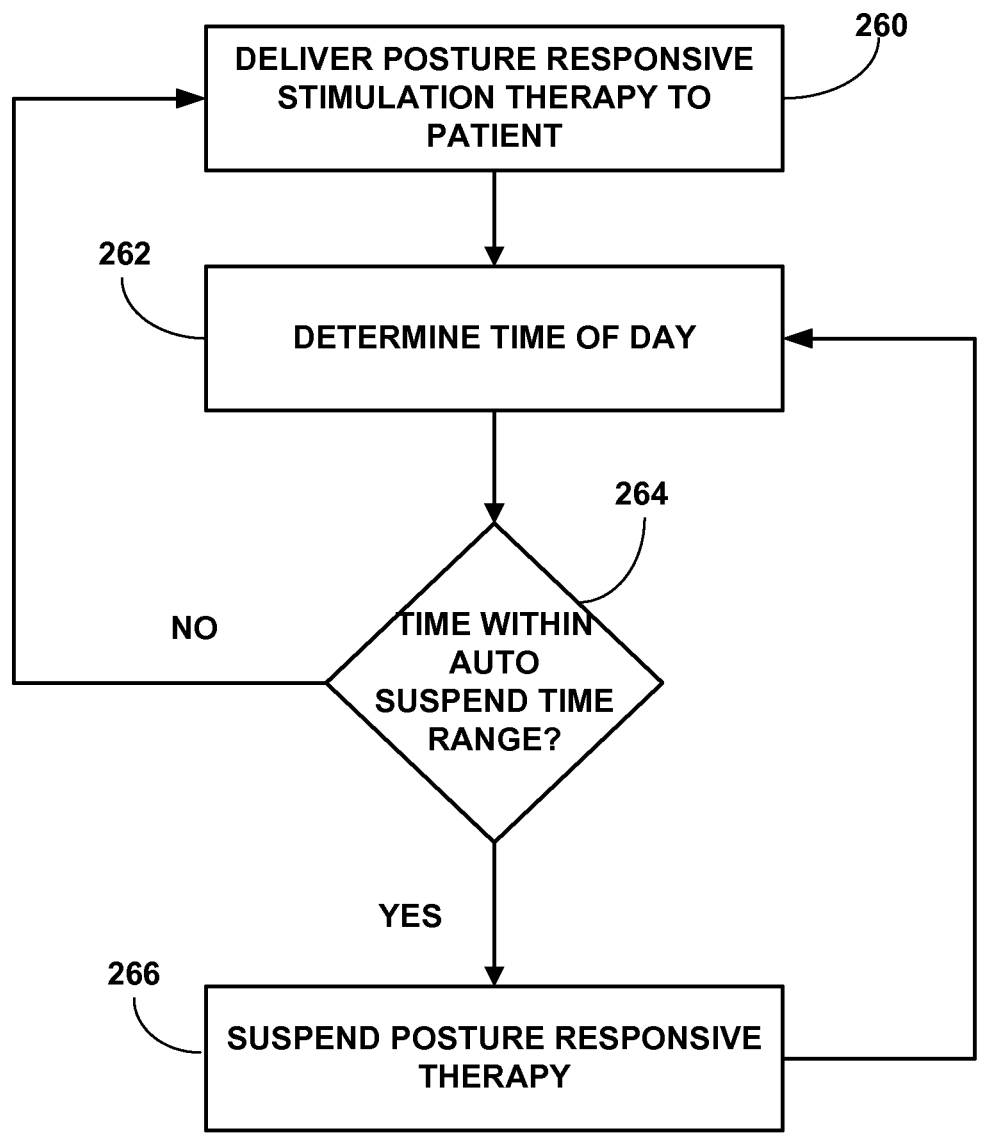
FIG. 15 is a flow diagram illustrating an example technique for automatically suspending posture-responsive therapy delivery to a patient based on time.

FIG. 15 is a flow diagram illustrating an example technique for automatically suspending posture-responsive therapy deliver to patient 12 based on time of day. Such a technique is one example of IMD 14 automatically adjusting one or more aspects of posture-responsive therapy delivered to patient 12 from IMD 14 based on time. While the example technique of FIG. 15 is described with respect to IMD 14, such a technique may be incorporated in any suitable medical device or system configured to deliver posture-responsive therapy to a patient.

According to FIG. 15, IMD 14 is active for delivery of posture-responsive stimulation therapy to patient 12 (260). For example, while active for posture-responsive simulation therapy, IMD 14 may detect the posture state of patient 12 via posture state module 86 and adjust the stimulation therapy according to the detected posture state of patient 12. While IMD 14 delivers posture-responsive therapy to patient 12, IMD 14 may periodically or continuously determines the time of day via timing unit 87 (262).

Using the time of day information determined from timing unit 87, processor 80 of IMD 14 may then determine whether the time of day is within one or more automatic suspension time ranges stored in memory 82 (264). If the time of day is within one or more of the automatic suspend time ranges defined in memory 82, then IMD 14 may automatically suspend delivery of one or more aspects of posture-responsive therapy to patient 12 (266). The one or more aspects of the posture-responsive therapy may be suspended until processor 80 determines that the time of day is no longer within an automatic suspend time range. Conversely, if the time of day is not within one or more of the automatic suspend time ranges defined in memory 82, then IMD 14 may continue to deliver posture-responsive therapy to patient 12 without suspending one or more aspects of the therapy (260). In this manner, IMD 14 may be configured to automatically suspend one or more aspects of posture-responsive therapy based on time.

An automatic suspension time range may define a range of time during which the delivery of posture-responsive therapy may be automatically suspended by IMD 14. As described with respect to FIG. 15, the automatic suspension time range may correspond to daily periods of time during which it may be desirable for IMD 14 to automatically suspend one or more aspects of posture-responsive therapy. In some examples, one or more automatic suspension time ranges may be defined to correspond to periods of a day in which the posture state of patient 12 is relatively constant or unchanged, therefore reducing the usefulness of automatically adjusting therapy when a patient transitions posture states, at least to the extent that it is unlikely that patient 12 will undergo a posture transition that requires a therapy adjustment during that time.

For example, during the period of time that patient 12 generally sleeps, patient 12 may occupy a general lying posture state for an extended period of time. Assuming that IMD 14 delivers substantially the same therapy to patient 12 regardless of the particular lying posture state, e.g., lying front, lying back, lying right, lying left, or if IMD 14 does not differentiate between the particular lying posture states, e.g., posture state module 86 only detects a general lying posture state rather than specific lying states, then one or more aspects of posture-responsive therapy may be suspended during the time period that patient 12 is sleeping without substantially reducing the efficacy of the therapy being delivered to patient 12. In such a situation, a time range corresponding to all or a portion of the time that patient 12 typically sleeps during the day may be identified and defined, e.g., by a clinician or patient 12 via programmer 30, 60, respectively, such that IMD 14 automatically suspends one or more aspects of the posture-responsive therapy to patient 12.

As another example, while awake, patient 12 may experience extended periods of time during which his/her posture state is substantially unchanged. For example, patient 12 may occupy a particular posture state, e.g., sitting at a desk, for an identifiable and extended period of time based on his/her occupation. In such a situation, an automatic suspend time period may be identified and defined to correspond to all or portion of the time period that patient 12 occupies the posture state associated with his/her occupation.

Furthermore, as illustrated by the fact that patient 12 generally will only work certain days in a week, automatic suspend time range may be defined not only on a daily basis, but also may be specific to certain days, groups of days, months, or any other suitable time period. For example, instead of automatic suspension time periods applied globally for all days, automatic suspend time information may be defined and stored in memory 82 such that IMD 14 takes into account not only the time of day but also the day of the week in determining whether one or more aspects of posture-responsive therapy should be suspended. Similar to determining the time of day, IMD 14 may also determine the day of week via timing unit 87. Examples using any suitable technique to differentiate time are contemplated.

In some examples, rather than defining ranges of time explicitly in terms of starting point time and end point time, e.g., from 1 a.m. to 5 a.m., that posture-responsive therapy should be suspended by IMD 14, memory 82 may contain automatic suspension time information in the form of one or more specific times that IMD should initiate suspension for one or more aspects of posture-responsive therapy and also a particular time period that the suspension should last. For example, memory 82 may contain instructions detailing that IMD 14 should automatically suspend one or more aspects of posture-responsive therapy at 1 a.m., and the suspension should last for a time period of 3 hours. In such a case, IMD 14 rather than continually monitoring the time of day via timing unit 87, IMD 14 may simply start a counter or timer for a period of 3 hours, in this example. When the timer or counter expires, then IMD 14 may resume the previously suspended aspect(s) of posture-responsive therapy. Such an example may be useful in situations in which the length of time that posture-responsive therapy should be suspended is relatively constant but the time that the suspension should start may vary occasionally because a user may only have to redefine the suspension start time in memory 82 without having to also directly change the suspension end time.

Alternatively or additionally, one or more automatic suspension time periods may be incorporated in IMD 14 by defining a particular time or range of time for IMD 14 to deliver posture-responsive therapy. For example, rather than defining the time period that therapy should be suspended in terms of when patient 12 is generally asleep, a user such as patient 12 may communicate periods of time during which posture-responsive therapy should be delivered. If processor 80 determines that the time of day, or any other time variable, is not within the defined posture-responsive time or range of time, IMD 14 may automatically suspend one or more aspects of the posture responsive therapy. In this manner, one or more automatic suspension time periods may be indirectly defined by a user by directly defining the time periods during which posture-responsive therapy should be delivered to patient 12 via IMD 14. Although particular examples are described, any suitable technique may be used such that IMD 14 may automatically suspend one or more aspects of posture responsive therapy based at least in part on time, as described herein.

IMD 14 may suspend one or more aspects of the posture-responsive therapy (266) in any suitable manner. In some examples, IMD 14 may suspend delivery of all posture-responsive therapy, e.g., by globally deactivating therapy groups for posture-responsive therapy. In such a case, IMD 14 may continue to deliver stimulation therapy to patient 12, though not on a posture-responsive basis. Instructions for the stimulation therapy delivered to patient 12 may be stored within memory 82 and accessed by processor 80 when posture-responsive therapy is suspended based on the determined time. For example, IMD 14 may continue to deliver therapy in the manner that was being delivered to patient 12 just prior to suspending the therapy to patient 12, or IMD 14 may deliver therapy to patient 12 according to a default therapy defined for automatic suspension periods. In some examples, IMD 14 may suspend the delivery of all types of stimulation to patient 12, including both posture-responsive and nonposture-responsive therapy.

In some examples, IMD 14 may only suspend certain aspects of the posture-responsive therapy while other posture-responsive aspects may remain active. The exact nature of the suspension may be tailored, e.g., by a clinician or patient 12, to be consistent with the activity (or inactivity) corresponding to the automatic suspend time range. For example, if an automatic suspend time period has be defined to correspond to a time period in which patient 12 is sleeping, IMD 14 may be configured to maintain delivery of posture-responsive therapy based on transitions between particular lying posture states, e.g., lying front, lying left, lying right, and lying back, but may suspend all other aspects of posture-responsive therapy. In this manner, IMD 14 may maintain delivery of therapy to patient 12 that is appropriate for the various lying posture states of patient 12. As another example, in a similar scenario, IMD 14 may be configured to maintain delivery of posture-responsive therapy to patient 12 based on transitions from lying to upright posture states but suspend delivery of posture responsive therapy for all other transitions. Such a configuration may be appropriate where a patient 12 receives substantially the same therapy in all lying down postures but requires different therapy in an upright posture state compared to that of lying posture state, so that IMD 14 may maintain appropriate therapy throughout the time patient 12 generally sleeps, including occasions when patient temporarily transitions to upright during the night, e.g., when patient 12 gets out of bed to go to the bathroom.

The suspension of posture responsive therapy to patient 12 by IMD 14 may include suspending detection of the posture state of patient 12 via posture state module 86. In other examples, posture state module 86 may continue to monitor the posture state of patient 12, but processor 80 may not adjust delivery of therapy to patient 12 while posture-responsive therapy is suspended. In some examples, posture state module 86 may continue to detect the posture state of patient 12 but the frequency at which posture state module 86 detects patient posture state 86 may be decreased. Adjustments to the frequency at which posture state module 86 detects patient posture state are generally described with regard to the example of FIG. 17, although suspension of one or more aspects of posture-responsive therapy may not accompany the frequency adjustment in the example of FIG. 17.

In any case, IMD 14 may suspend one or more aspects of posture responsive stimulation therapy to patient 12 based at least in part on time. In this manner, IMD 14 may be configured to suspend the one or more aspects of posture-responsive therapy to reduce or minimize power consumed by IMD 14.

IMD 14 may resume the one or more aspects of posture-responsive therapy that were automatically suspended based on time using any suitable technique. In the example of FIG. 15, IMD 14 continues to monitor the time of day via timing module 87 to determine when the time of day is no longer within one or more automatic suspension time ranges, at which time IMD 14 may resume the suspended therapy. Alternatively or additionally, IMD 14 may resume one or more aspects of the suspended therapy based on the detected posture state of patient 12. For example, in cases in which posture state module 86 continues monitoring the posture state of patient 12 during the suspension of therapy, IMD 14 may resume the suspended therapy upon detecting that patient 12 has transitioned posture states, either in general or to one or more posture states defined as indicators that suspended therapy should be resumed by IMD 14. In some examples, as described above, the one or more aspects may be resumed upon expiration of a timer defining the length of an automatic suspension time period.

Figure 16:
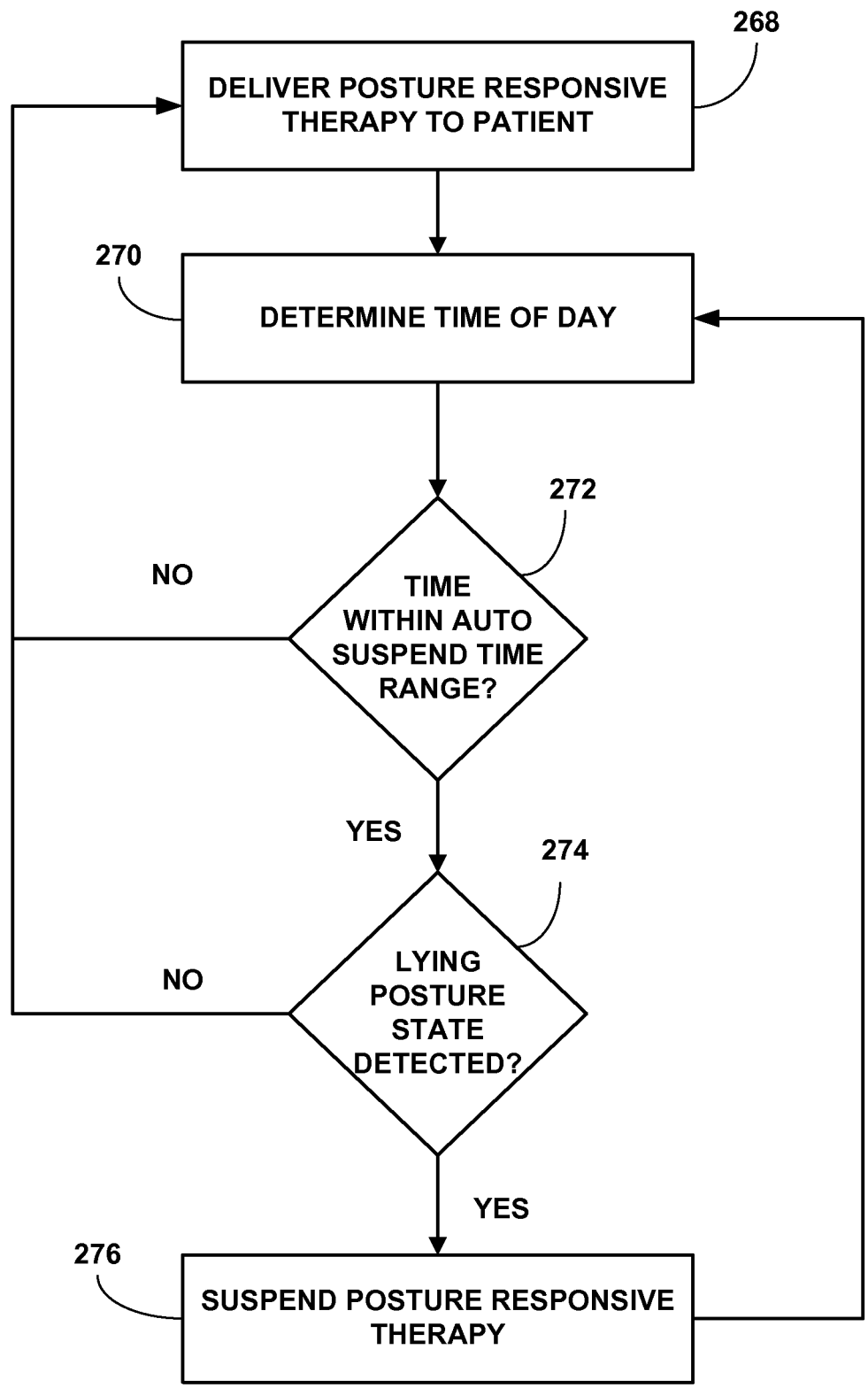
FIG. 16 is a flow diagram illustrating an example technique for automatically suspending posture-responsive therapy to patient 12 based on time.

FIG. 16 is a flow diagram illustrating an example technique for automatically suspending posture-responsive therapy to patient 12. The example of FIG. 16 is substantially similar to that shown in FIG. 15. However, as will be apparent from the description of FIG. 16. IMD 14 may automatically suspend one or more aspects of posture-responsive therapy based on time in conjunction with verification of the suspension with another sensed patient parameter.

IMD 14 delivers posture-responsive stimulation therapy to patient 12 (268). While IMD 14 delivers posture-responsive therapy, IMD 14 may periodically or continuously determine the time of day via timing unit 87 (270). Using the time information determined from timing unit 87, processor 80 of IMD 14 may then determine whether the time of day is within one or more automatic suspension time ranges stored in memory 82 (272). As described above, one or more automatic suspension time ranges may be defined to correspond to all or a portion of the time that patient 12 typically sleeps. If the time is not within the one or more automatic suspension time ranges, then IMD 14 continues to deliver posture-responsive stimulation to patient 12 (268).

However, unlike the example of FIG. 15, if processor 80 of IMD 14 determines that the time of day is within one or more automatic suspend time ranges, instead of automatically suspending one or more aspects of the posture-responsive therapy, as in the example of FIG. 15, processor 80 determines whether patient 12 is in a lying posture state, as detected by posture state module 86 (274). If processor 80 determines that patient 12 is in a lying posture state, then IMD 14 may suspend one or more aspects of the posture-responsive therapy (276). For example, IMD 14 may suspend the posture-responsive therapy in a manner the same or similar to that described with regard to the example of FIG. 15. Conversely, if processor 80 determines that patient 12 is not within a lying posture state, IMD 14 may maintain delivery of posture-responsive therapy to patient 12 (268).

In this manner, IMD 14 may use the posture state of patient to verify that automatic suspension of posture-responsive therapy based on the time of day being within an automatic suspension time period is appropriate by determining that a detected patient parameter is consistent with the automatic suspension. Specifically, since the automatic suspension time period corresponds to a time period that patient 12 generally sleeps, IMD 14 may verify that the automatic suspension is appropriate by checking that the detected patient posture state is consistent with patient 12 sleeping.

In some examples, IMD 14 may alternatively or additionally use other patient parameters to verify that the automatic suspension of one or more aspects of posture-responsive therapy is appropriate based on time. For example, IMD 14 may monitor one or more of patient heart rate, blood pressure, respiration rate, ECG morphological features, respiratory volume, blood oxygen saturation, muscle activity, core temperature, subcutaneous temperature, article blood flow, brain electrical activity, eye motion, or galvanic skin response.

Figure 17:
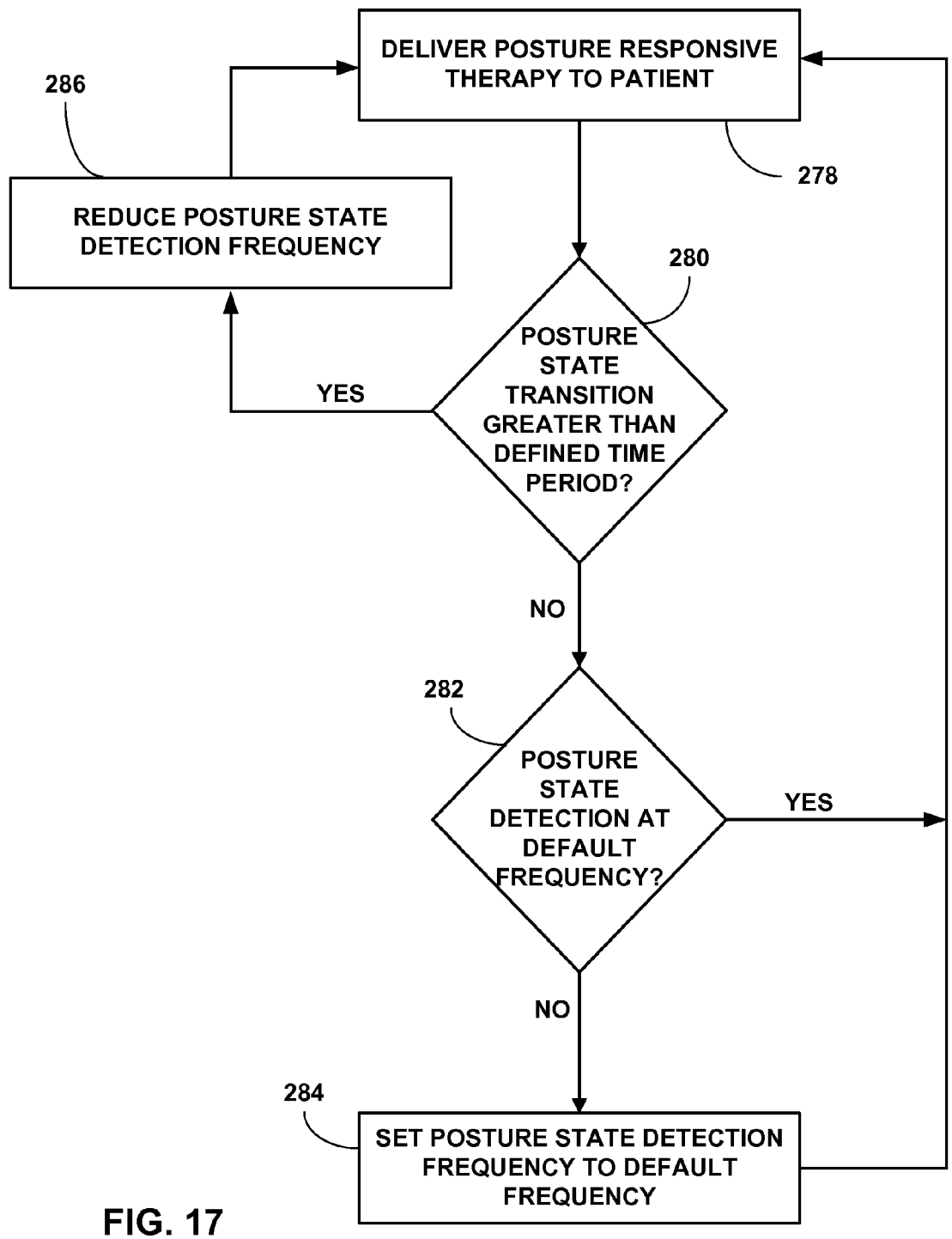
FIG. 17 is a flow diagram illustrating an example technique for automatically adjusting the posture state detection frequency based on the posture state behavior of a patient.

FIG. 17 is a flow diagram illustrating an example technique for automatically adjusting the posture state detection frequency based on the posture state behavior of a patient 12. Such a technique is one example of IMD 14 automatically adjusting one or more aspects of posture-responsive therapy delivered to patient 12 from IMD 14 based on patient posture state behavior. While the example technique of FIG. 17 is described with respect to IMD 14, such a technique may be incorporated in any suitable medical device or system configured to deliver posture-responsive therapy to a patient.

According to FIG. 17, IMD 14 is active for delivery of posture-responsive stimulation therapy to patient 12 (278). For example, while active for posture-responsive simulation therapy, IMD 14 may detect the posture state of patient 12 via posture state module 86 and adjust the stimulation therapy according to the detected posture state of patient 12. While IMD 14 delivers posture-responsive therapy to patient 12, IMD 14 may monitor for the time elapsed between detected posture state transitions, e.g., by tracking the amount of time since the last detected posture state transition via timing module 87. Processor 80 may continually or periodically compare the amount of time elapsed since the previous posture state transition to one or more lengths of time defined for an automatic detection frequency adjustment (280).

If the amount of time elapsed since that last posture state transition is greater than a length of time defined for an automatic posture state detection frequency reduction, then IMD 14 may automatically decrease the frequency with which posture state module 86 detects the posture state of patient 12. Alternatively, if IMD 14 determines that the amount of time elapsed since the previous posture state transition is not greater than a length of time defined from an automatic posture state detection frequency reduction, then IMD 14 may determine whether the current detection frequency of posture state module 86 is at a defined default value (282), e.g., to determine whether the frequency had been previously reduced. If the posture state detection frequency is at the default frequency value, then IMD 14 may continue delivery of posture-responsive therapy to patient 12 (278) without adjusting the posture state detection frequency. However, if IMD 14 determines that the posture state detection frequency is not the default value, e.g., the frequency had been previously reduced, then IMD 14 may adjust the posture state detection frequency to the default value (284), and then continue to deliver posture-responsive therapy (278). In this manner, IMD 14 may automatically adjust the detection frequency at which posture state module 86 detects the posture state of patient 12 based at least in part on the posture state behavior of patient 12.

During posture-responsive therapy, posture state module 86 may detect the posture state of patient 12 according to a default frequency value to monitor patient posture state to allow IMD 14 to deliver therapy according to the detected patient posture state. In some examples, posture state module 86 may be configured to detect the posture state of patient every second, i.e., at a frequency of 1 Hz, as a default frequency value when IMD 14 is activated for delivery of posture-responsive therapy. In other examples, the default detection frequency may range from approximately 0.5 Hz to approximately 5 Hz, such as, e.g., approximately 2 Hz to approximately 4 Hz. Examples with frequencies other than that listed above are also contemplated.

However, in some cases, it may be possible to reduce the frequency at which posture state module 86 of IMD 14 monitors the posture state of patient 12 for delivery of posture-responsive therapy. Despite the reduction in posture state detection frequency, IMD 14 may continue to deliver efficacious therapy on a posture responsive basis. For example, during a period in which patient 12 is sleeping, the frequency at which patient 12 undergoes posture state transitions may be less than that when patient 12 is not sleeping. As such, during all or a portion of the period that patient 12 is sleeping, the frequency at which posture state module 86 detects the posture state of patient 12 may be reduced. As another example, patient 12 may undertake infrequent posture state changes for an extended period based on the occupation of patient 12, e.g., patient 12 may sit at a desk for extended periods. Again, during all or a portion of the time period that patient 12 is sitting at a desk, the frequency at which posture state module 86 detects the posture state of patient 12 may be reduced.

Accordingly, in some examples, IMD 14 may monitor the posture state of patient 12 to identify behavior of patient 12 which may be indicative of patient 12 occupying a posture state for an extended period of time, or at least that the posture state detection frequency may be reduced. As in the example of FIG. 17, IMD 14 may be configured to identify such a situation based on the amount of time elapsed since the last posture state transition relative to one or more defined automatic adjustment time amounts, as described above. For example, if IMD 14 has determined that patient 12 has occupied a lying posture state without a posture state transition for an amount of time greater than the defined automatic adjustment length, then IMD 14 may automatically reduce the posture state detection frequency corresponding to the posture state behavior which indicates that patient 12 is sleeping.

IMD 14 may automatically reduce the posture state detection frequency from the default detection frequency by any suitable amount based on the posture state behavior of patient 12. For example, IMD 14 may automatically reduce the posture state detection frequency to a value of approximately 0.1 Hz to approximately 1 Hz, such as, e.g., approximately 0.2 Hz to approximately 1 Hz. In some examples, IMD 14 may automatically reduce the posture state detection frequency by approximately 50 percent to approximately 90 percent, such as, e.g., approximately 75 percent to approximately 90 percent. Examples with frequencies and frequencies reduction percentages other than that listed above are also contemplated. Other frequencies are contemplated. In some examples, a minimum frequency value may be defined to which IMD 14 reduces the posture state detection frequency regardless of the default frequency value that is being adjusted. By automatically reducing the posture state detection frequency of posture state module 86, IMD 14 may reduce or minimize the amount of power consumed during posture-responsive therapy and/or reduce the overall amount of data analysis required by posture state module 86 and processor 80.

In some examples, posture state detection frequency may include a posture state calculation frequency and a posture sensor sampling frequency. The posture sensor sampling frequency may define the frequency at which posture state module 86 samples the signal output generated by one or more posture sensor, such as, e.g., one or more 3-axis accelerometers, used to determine the patient posture state. The posture state calculation frequency may define the frequency at which posture state module 86 calculates the posture state of patient 12 based on the sampled sensor signal data, e.g., using one or more posture state detection algorithms consistent with the example posture state determination techniques described in FIGS. 8A-8C. In some cases, the posture sensor sampling frequency may be substantially the same as the posture state calculation frequency. Alternatively, the posture sensor sampling frequency may greater than the posture state calculation frequency. In such a configuration, the sensor signal output from multiple sampled sensor signals may be averaged (or manipulated in some manner, e.g., to account for occurrences of outlying sensor signals), and then posture state module 86 may calculate the posture state of patient 12 based on a plurality of sampled sensor signals.

Accordingly, in examples in which the posture state detection frequency includes both a posture state calculation frequency and a posture sensor sampling frequency, one or both of the respective frequencies may be reduced to reduce the posture state detection frequency. For example, posture state module 86 may reduce the posture state detection frequency (286) by reducing the posture state calculation frequency but maintaining substantially the same posture sensor sampling frequency. Such an example may be appropriate when power consumption is relatively more dependent on the posture state calculation frequency compared to that of the posture sensor sampling frequency. In other examples, posture state module 86 may reduce the posture state detection frequency (286) by reducing the posture sensor sampling frequency but maintaining substantially the same posture state calculation frequency. In other examples, posture state module 86 may reduce the posture state detection frequency (286) by reducing both the posture sensor sampling frequency and the posture state calculation frequency.

In some examples, the default posture state calculation frequency may range from approximately 0.5 Hz to approximately 5 Hz, such as, e.g., approximately 2 Hz to approximately 4 Hz. In some examples, the default posture sensor sampling frequency may range from approximately 1 Hz to approximately 250 Hz, such as, e.g., approximately 8 Hz to approximately 32 Hz. Reduced posture state calculation frequencies may range from approximately 0.1 Hz to approximately 1 Hz, such as, e.g., approximately 0.2 Hz to approximately 1 Hz. Reduced posture sensor detection frequencies may range from approximately 4 Hz to approximately 60 Hz, such as, e.g., approximately 4 Hz to approximately 12 Hz. However, other posture state calculation and posture sensor sampling frequencies are contemplated.

In some examples, rather than monitoring for any transition between two specific posture states, IMD 14 may be configured to monitor for particular types of posture state transitions. For example, while patient 12 may transition between lying left, lying right, lying front, lying back posture state when sleeping, patient 12 may still generally occupy a lying posture state. In terms of posture state detection frequency, a reduced frequency value may be appropriate despite the transition between individual lying posture states. Accordingly, for purposes of automatic frequency adjustment, IMD 14 may ignore posture state transitions between individual lying posture states. Instead, IMD 14 may track the amount of time elapsed since patient 12 occupied any type of lying posture state for purposes of automatically reducing the detection frequency and maintaining the frequency at the reduced value.

As shown in FIG. 17, IMD 14 may increase the posture state detection frequency to the default value based on the posture state behavior of patient 12, e.g., once IMD 14 determines that patient 12 has generally transitioned posture states or transitioned to a particular type of posture state. In some cases, after the posture state detection frequency has been reduced, IMD 14 may ignore transitions out of one posture state to another, e.g., a lying posture state, in which patient 12 returns to the previous posture state or grouping of posture states, e.g., any of multiple lying posture states, in a relatively short amount of time. In this manner, IMD 14 may maintain a reduced posture state detection frequency even if patient 12 temporary transitions to another posture state, e.g., when patient 12 temporary gets out of bed to go to the bathroom.

In some examples, IMD 14 may be configured to return to the default detection frequency (higher frequency) from a reduced detection frequency by monitoring the raw sensor signal output after the detection frequency has been reduced. As an example, as described above in FIG. 17, posture state module 86 may reduce the posture state detection frequency (286) based on patient 12 occupying a particular posture state without transition for a length of time greater than the amount of time defined for an automatic frequency reduction (280). In some examples, posture state module 86 may reduce the detection frequency (286) by reducing the posture state calculation frequency from the default frequency value, as described above. During that time, posture state module 86 may continue to sample the posture sensor signal output, either at the default or a reduced frequency, and monitor one or more sensor outputs to determine when to return the calculation frequency to the default value (high frequency). In some examples, posture state module 86 may use a first order monitor of the raw sensor signal from each axis of 3-axis accelerometer to detect the differences in the raw sensor signals. For example, for each axis, posture state module 86 may compare consecutive samples of the raw signal to determine whether the difference between the respective sensor signals are greater than a threshold difference. In some examples, the threshold difference may be one or more pre-programmed values, e.g., a predefined threshold difference of greater than 10 centi-g's, 5 LSB, or any other suitable value) along any axis, or may be a defined in view of a dynamically determined average difference between sensor samples. Posture state module 86 may continue to operate at the reduced detection frequency value as long as the raw sensor signal is relatively stable, e.g., as determined by comparing the difference between two or more sampled sensor signals to a threshold value. Conversely, if posture state module 86 detects a difference between raw sensor signals that is greater than the a threshold difference defined for the monitoring process, then posture state module 86 may automatically increase the calculation frequency, e.g., to the default detection frequency value, or even resume calculation of the posture state in cases in which the calculation of the posture state has been suspended.

Using such a technique, posture state module 86 may be configured to monitor the raw sensor signal in a manner that allows the calculation frequency to be increased to the default value prior to patient 12 actually transitioning posture states. For example, posture state module 86 may monitor for variations in the raw sensor signal on a scale smaller than that in which posture state transitions are detected. In the case of a posture state cone, the degree of signal variation that triggers the calculation frequency to be increased may be represented by a smaller volume within a larger cone defining a patient posture state, e.g., a lying posture state. When posture state sensor 86 detects a variation in sampled sensor signals corresponding to a transitions out the smaller volume within the larger posture state volume, then posture state module 86 may increase the posture state calculation frequency. In this manner, posture state module 86 may anticipate a posture state transition by monitoring the raw sensor signal and, in some examples, resume posture state calculations at an appropriate frequency prior patient 12 actually transitioning to another posture state. Assuming that the raw signal monitoring process requires less power than that of the posture state calculation process at the reduce frequency, posture state module 86 may reduce the amount of power consumed in such a manner.

A similar process may also be used to determine when posture state module 12 automatically reduces the posture state detection frequency, as described herein. For example, IMD 14 may monitor the sensor signal as described to determine when patient 12 occupies a smaller space within a posture state cone for a threshold amount of time, and then automatically reduce one or more aspects of the posture state detection frequency based on the determination.

The example techniques of FIGS. 15-17 generally illustrate examples in which IMD 14 automatically adjusts at least one aspect of posture responsive therapy based on time and/or patient posture state behavior. While the examples of FIGS. 15 and 16 are described in terms of automatically suspending therapy, such examples may be modified to automatically reduce posture state detection frequency based at least in part on time, as described in FIG. 17. Similarly, the examples of FIG. 17 may be modified to automatically suspend therapy based at least in part on patient behavior. While the examples of FIGS. 15 and 16 were described with respect to IMD 14 determining the time of day via timing module 87 and then automatically suspending therapy based on time, in some examples another device, such as programmer 30 or programmer 60 may monitor time and communicate the time information to IMD 14 via telemetry circuitry. Further, in some examples, programmer 30 or programmer 60 may monitor time and determine that one or more aspects of posture-responsive therapy should be suspended based on time, and then communicate an indication to IMD 14 consistent with that determination. Similarly, portions of the example of FIG. 17 may be carried out via a device such as programmer 30 or 60 other than that of IMD 14.

As previously described, in some examples, IMD 14 may be configured to deliver stimulation therapy according to the posture state of patient 12 detected via posture state module 86. For example, IMD 14 may be configured to deliver stimulation therapy according to one or more specified therapy programs or groups whenever IMD 14 detects that patient 12 is in a particular posture state. IMD 14 may use one or more techniques to detect the posture state of patient 12. For example, the posture state of patient 12 may be detected using posture cones defined with respect to one or more characteristics of a signal generated by one or more posture state sensors, such as one or more accelerometers. IMD 14 may then associate one or more stimulation therapy programs with the defined posture cone, such that whenever posture state module 86 senses a signal from the posture state sensor that falls within the definition of the respective posture cone, IMD 14 delivers stimulation according to the one or more associated therapy programs.

However, in some situations, patient 12 may actually occupy a posture state that does not fall precisely within a defined posture cone. For example, with reference to FIG. 8B, the actual posture state occupied by patient 12 may correspond to a location in posture state space 152 that is not within one of cones 154, 156, and 158. For example, the undefined posture state may reside within a hysteresis zone that separates adjacent posture cones designed to avoid repeatedly toggling between posture state cones. In such cases, IMD 14 may be configured to deliver stimulation therapy to patient 12 when the sensor signal generated by the one or more posture state sensors indicates patient 12 is within an undefined space even though patient 12 is not in a defined posture state, rather than not providing stimulation therapy to patient 12 when patient 12 occupies an undefined posture state.

In some examples, when patient 12 occupies an undefined posture state, IMD 14 may maintain stimulation therapy based on the most recent defined posture state occupied by patient 12. In such cases, IMD 14 may deliver stimulation therapy to patient 12 when they are in an undefined posture state according to the stimulation therapy associated with the most recent defined posture state that IMD 14 detected as being occupied by patient 12. In this manner, stimulation therapy may be delivered to patient even though patient 12 is in an undefined posture state. Furthermore, such a technique may be appropriate in cases in which the most effective stimulation to deliver to patient 12 in an undefined posture state depends on the most recent define posture state that patient 12 occupied.

A situation such as that described may occur when patient 12 transitions from standing to sitting in a chair in a reclined position. In such a situation, IMD 14 may detect via posture state module 86 that patient 12 has transitioned from a posture state that fits within a defined "Upright" posture cone to a posture state that fits within an undefined space between the "Upright" posture cone and one or more "Lying" posture cones. Using the technique previously described, IMD 14 may deliver stimulation therapy to patient 12 according to one or more programs associated with the "Upright" posture cone when they are in the reclined position as described.

However, in such a case, patient 12 may be unhappy with the stimulation therapy that they are receiving from IMD 14 when they are in the reclined position. Instead, for example, patient 12 may wish to receive stimulation therapy that is delivered to patient 12 when patient 12 is in a defined lying posture state, such as the defined "lying (back)" posture state. In accordance with some aspects of the disclosure, in some examples, patient 12 may be allowed to temporarily override the stimulation therapy being delivered by IMD 14, e.g., to select stimulation therapy associated with another posture state. For example, when patient 12 is in an undefined posture state, patient 12 may be allowed to temporarily override the stimulation therapy being delivered by IMD 14 by selecting stimulation therapy associated with a defined posture state.

Figure 18:
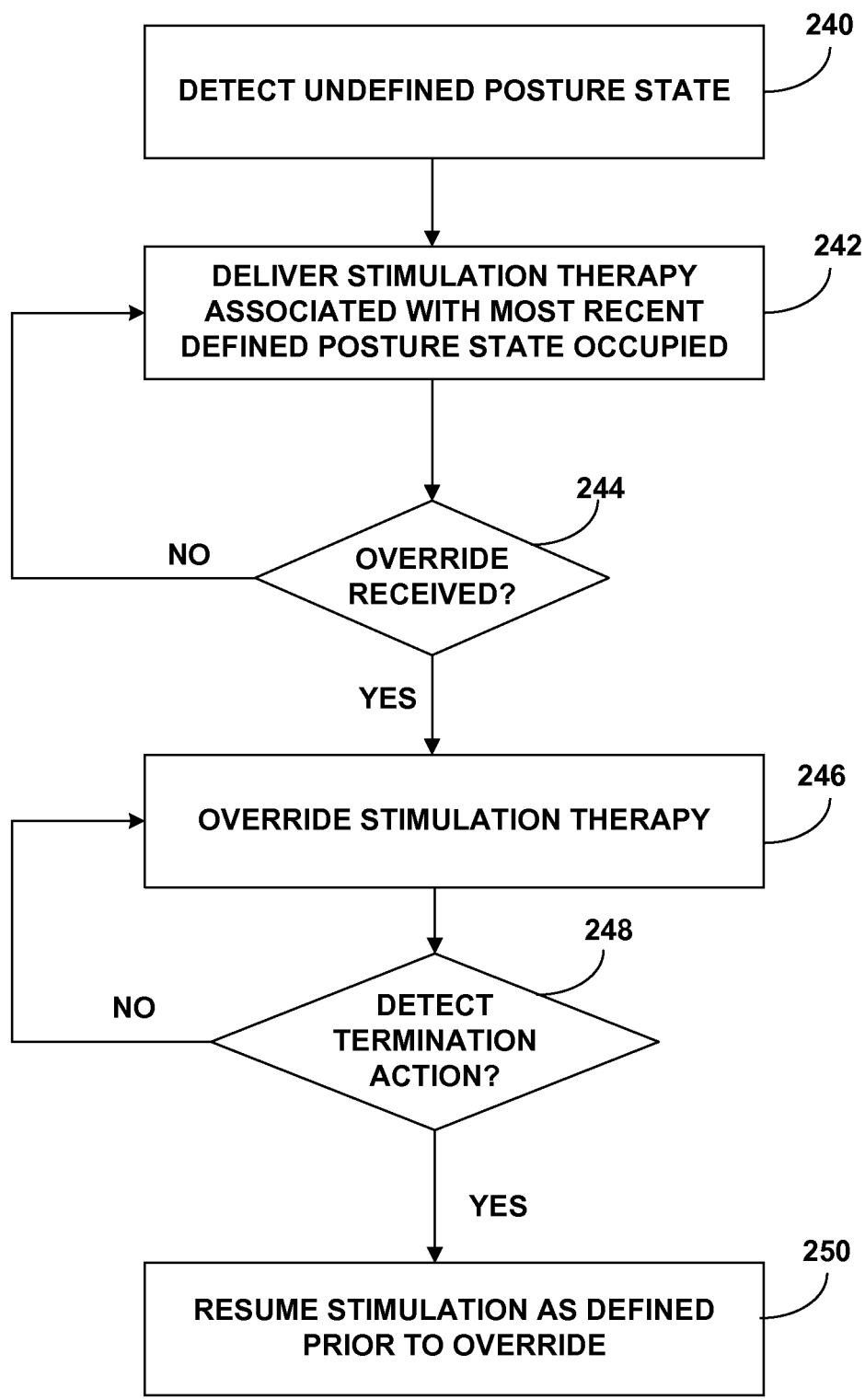
FIG. 18 is a flowchart illustrating an example technique for overriding stimulation therapy being delivered by an IMD to a patient.

FIG. 18 is a flowchart illustrating an example technique for overriding stimulation therapy being delivered by IMD 14 to patient 12. As shown, IMD 14 may detect that patient 12 is in an undefined posture state via posture state module 86 (240), e.g., using one or more posture cones defining the posture states of patient 12. As previously described, IMD 14 may deliver stimulation therapy according to the one or more stimulation therapy programs associated with the most recently defined posture state occupied by patient 12 (242). While patient 12 occupies the undefined posture state, IMD 14 may or may not receive an indication that the stimulation therapy should be overridden (244). If IMD 14 does not receive an override indication, IMD 14 may continue to deliver stimulation therapy to patient 12 according to the one or more therapy programs associated with the most recently defined posture state occupied by patient (242). IMD 14 may continue to monitor for an override indication until it detects that patient 12 has transitioned to a defined posture state.

However, if IMD 14 does receive an override indication, IMD 14 may then override the stimulation therapy that is being delivered to patient 12 (246), e.g., such that IMD 14 delivers therapy according to one or more different therapy programs. This override indication may be sent from programmer 30 to IMD 14 based on patient 12 input to programmer 39 that the stimulation therapy being delivered should be overridden.

For example, patient 12 may communicate to programmer 30 that the stimulation therapy should be delivered according to a different posture state. The different posture state may be a defined posture state that is different from the most recently detected defined posture state. In some examples, programmer 30 may display the current posture state according to which stimulation therapy is being delivered to patient. Based on the posture state displayed to patient 12, patient 12 may determine if they would rather have stimulation therapy be delivered according to another defined posture state. If so, patient 12 may indicate that desired posture state to IMD 14 via programmer 30. Upon receipt of such an indication, IMD 14 may override the stimulation therapy being delivered to stimulation therapy according to the posture state indicated by patient 12.

In another example, patient 12 may attempt to adjust the value of one or more stimulation parameters while IMD 14 is delivering the stimulation therapy according to the most recent define posture state occupied by patient 12. Such an action may be viewed as an override indication to the extent that patient 12 may desire that the one or more aspects of the stimulation therapy being delivered should be adjusted. In such an example, IMD 14 may override the stimulation being delivered to patient 12 by adjusting the one or more parameters to values indicated by patient 12 via programmer 30.

In general, IMD 14 may temporarily override the stimulation therapy being delivered to patient 12. At some point after overriding the stimulation being delivered to patient 12, IMD 14 may revert back to the stimulation therapy as defined prior to the stimulation therapy override, either automatically or upon user approval. Alternatively, IMD 14 may begin delivering therapy according to a new posture state to which patient 12 has now transitioned. In this manner, the stimulation therapy delivered by IMD 14 to patient 12 may not be permanently changed, but instead is only temporarily overridden.

As illustrated by FIG. 18, in some examples, one or more override termination actions may be detected by IMD 14 (248). If IMD 14 does not detect an override termination action, IMD 14 may maintain the delivery of stimulation according to the override received (246). However, if IMD 14 does detect an override termination action, IMD 14 may resume delivery of stimulation as defined prior to the stimulation override (250).

An override termination action may be one or more actions or states that, when detected by IMD 14, causes IMD 14 to revert back to stimulation therapy as defined prior to the stimulation therapy override or to transition to a different stimulation therapy associated with another detected posture state. In one example, the override termination action may include patient input sent via programmer 30 indicating that IMD 14 should terminate that override. As another example, the override termination action may include the expiration of one or more timers that define the amount of time that IMD 14 should override stimulation.

Once the timers expire, IMD 14 may resume stimulation therapy as it was prior to the override or, in some cases, programmer 30 may prompt patient 12 to reaffirm the override, continue for another time period, and/or make the override permanent. As another example, IMD 14 may detect that patient 12 has transitioned out of the undefined posture state to another posture state, which may be defined or undefined. Once IMD 14 has detected the posture state transition, IMD 14 may terminate the override and resume stimulation therapy or transition to a different stimulation therapy associated with the new postures state, as previously described.

As an illustration, if patient 12 transitions from an upright posture state to an undefined posture state (e.g., a reclining state that resides between an upright posture cone and a lying down posture cone), IMD 14 may continue to deliver stimulation therapy programmed for the upright state but may also send a message to the external programmer that notifies the user of the undefined posture state. In this case, patient 12 may simply maintain the existing stimulation therapy, adjust one or more parameter values associated with the existing stimulation therapy, or provide input indicating that the posture state should be treated as a lying down posture state. In this case, programmer 30 sends a command to IMD 14 to cause IMD 14 to deliver stimulation programmed for the lying down posture state even though the patient is actually occupying an undefined posture state.

Although the provided examples have been described with respect to overriding stimulation therapy when IMD 14 detects that patient 12 is in an undefined posture state, in some examples, the same or similar techniques may be utilized in general to temporarily override the stimulation being delivered to patient 12 even when IMD 14 detects that patient 12 is in a defined posture state. For example, IMD 14 may detect that patient 12 is occupying a defined posture state and deliver stimulation therapy according to the defined posture state. While delivering stimulation therapy, IMD 14 may receive an indication from programmer 30 that the stimulation therapy should be temporarily overridden, e.g., by delivering stimulation therapy according to one or more therapy programs associated with another posture state.

Figure 19A:
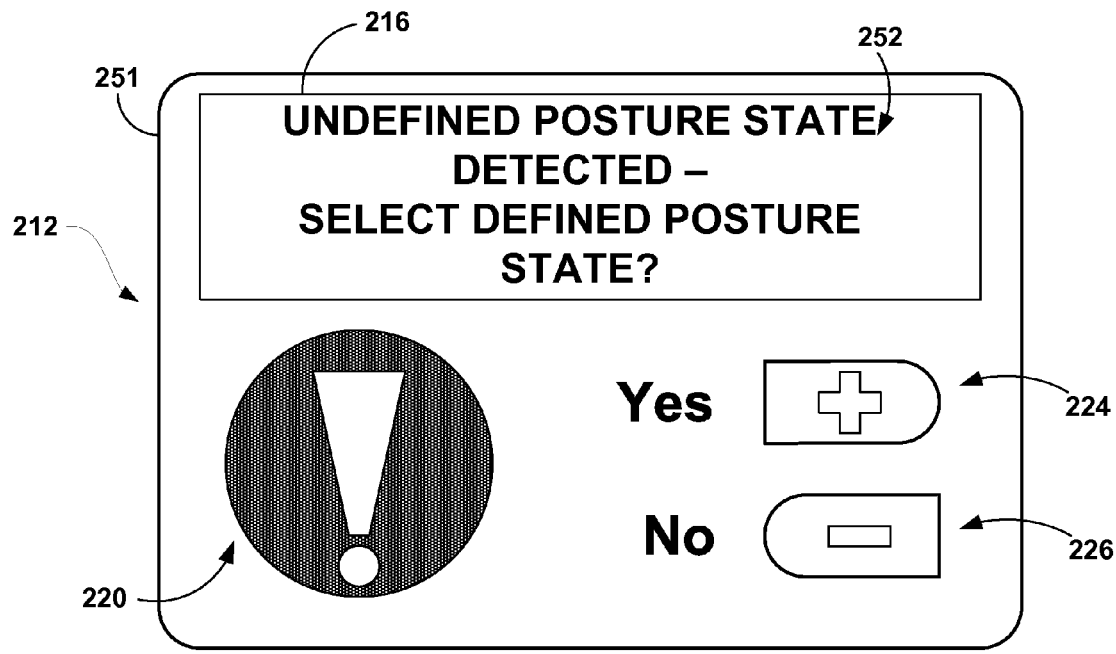
FIGS. 19A and 19B are conceptual diagrams illustrating an example screen of a user interface for prompting a user to select a defined posture state when an undefined posture state is detected.
Figure 19B:
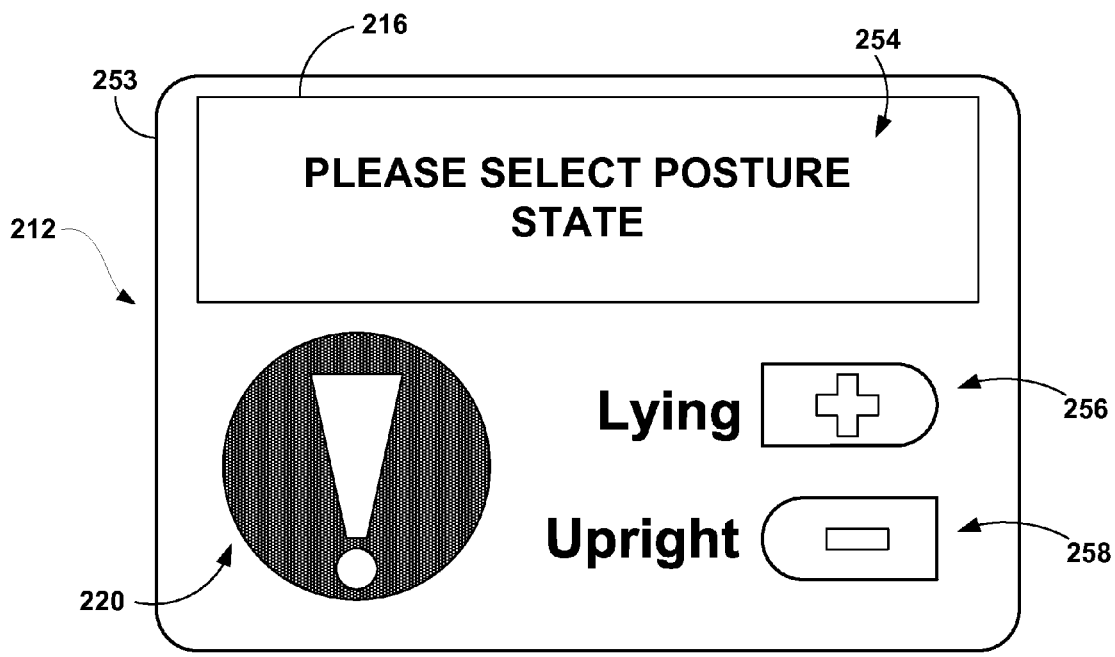

FIGS. 19A and 19B are conceptual diagrams illustrating an example screen of a user interface for prompting a user to select a defined posture state when an undefined posture state is detected. As shown in FIG. 19A, screen 251 presents selection box 216, alert icon 220, prompt text 252, yes prompt 224, and no prompt 226. Screen 214 may be displayed to patient 12 when IMD 14 detects patient 12 is in an undefined posture state to indicate to patient 12 that an undefined posture has been detected. In particular, prompt text 252 seeks to notify the patient 12 of the detection of an undefined posture state and confirm whether patient 12 would like to override (or confirm) the current stimulation therapy by selecting a defined posture state. If the current stimulation therapy is provided for the upright posture state, for example, selecting the upright posture state (or not selecting a defined posture state) would confirm the stimulation therapy and selecting the lying posture state would override the current stimulation, replacing it with stimulation for the lying posture state.

If patient 12 would like to select a defined posture state, as prompted by text 252, the patient may press increase button 52 as shown by yes prompt 224. If patient 12 would not like to select a defined posture state, then patient 12 may select decrease button 50 as shown by no prompt 226. Programmer 30 then may send an appropriate instruction to IMD 14. Alternatively, if no action is to be taken, a timeout for a reply from programmer 30 may be interpreted by IMD 14 to indicate that no action is to be taken.

As shown in FIG. 19B, if patient 12 would like to selected a defined posture state, then programmer 30 may transition to another screen 253, which presents text 254, instructing patient 12 to select either the lying or upright position as indicated by prompts 256 and 258, respectively. Upon patient 12 selecting of one of the defined posture states, programmer 30 may communicate the selection to IMD 14. IMD 14 may then deliver stimulation therapy programmed for the selected defined posture state even though the patient resides in an undefined posture state, subject to any of a variety of termination actions as described with reference to FIG. 18. This is merely one example, and screen 253 may include a list of many posture states other than, or in addition to, those shown from which a patient may select when specifying which therapy is desired. In one example, screen 253 could be populated with posture states that are adjacent to a hysteresis zone the patient occupies.

The techniques described in this disclosure may be implemented, at least in part, in hardware, software, firmware or any combination thereof. For example, various aspects of the techniques may be implemented within one or more microprocessors, DSPs, ASICs, FPGAs, or any other equivalent integrated or discrete logic circuitry, as well as any combinations of such components, embodied in programmers, such as physician or patient programmers, stimulators, or other devices. The term "processor" or "processing circuitry" may generally refer to any of the foregoing logic circuitry, alone or in combination with other logic circuitry, or any other equivalent circuitry.

When implemented in software, the functionality ascribed to the systems and devices described in this disclosure may be embodied as instructions on a computer-readable medium such as RAM, ROM, NVRAM, EEPROM, FLASH memory, magnetic media, optical media, or the like. The instructions may be executed to support one or more aspects of the functionality described in this disclosure.

In addition, it should be noted that the systems described herein may not be limited to treatment of a human patient. In alternative examples, these systems may be implemented in non-human patients, e.g., primates, canines, equines, pigs, and felines. These animals may undergo clinical or research therapies that may benefit from the subject matter of this disclosure.

Many examples of the disclosure have been described. Various modifications may be made without departing from the scope of the claims. These and other examples are within the scope of the following claims.

The invention claimed is:

1. A method comprising:
receiving a first indication from an external device to resume delivery to a patient of therapy that was suspended, wherein the therapy that was suspended comprises therapy delivered to the patient via a medical device according to a detected posture state of the patient, and wherein the received first indication is generated by the external device based on input from a user indicating that the delivery of therapy should be resumed;
receiving a second indication from the external device, after suspension of the therapy, indicating therapy information to define the therapy to be delivered to the patient when the therapy is resumed; and
resuming the delivery of therapy to the patient via the medical device in response to the receipt of the first indication to resume the delivery of therapy, wherein the therapy delivered via the medical device is resumed according to the therapy information.

2. The method of claim 1, wherein the therapy information comprises therapy information defining one or more aspects of the therapy delivered according to the detected posture state of the patient prior to the therapy being suspended.

3. The method of claim 1, wherein the therapy information comprises therapy information defined at approximately a time the delivery of stimulation therapy was suspended.

4. The method of claim 1, wherein the therapy information comprises therapy information defined when the delivery of stimulation therapy was initialized.

5. The method of claim 1, wherein the therapy information comprises therapy information associated with a posture state of the patient detected at a time when the therapy is resumed.

6. The method of claim 1, wherein the therapy information comprises therapy information defined prior to the therapy being turned off but after the therapy was initialized.

7. The method of claim 1, wherein the external device is a clinician programmer.

8. The method of claim 1, further comprising:
sending the therapy information to the external device; and
receiving a third indication from the external device confirming that the therapy should be resumed according to the therapy information.

9. The method of claim 1, wherein the therapy comprises electrical stimulation therapy.

10. The method of claim 1, wherein the therapy that was suspended further comprises therapy delivered to the patient not according to the detected posture state of the patient.

11. The method of claim 1, further comprising:
detecting, via a processor, the posture state of the patient based on output of a posture state sensor;
controlling the delivery of the therapy based on the detected posture state of the patient;
subsequently receiving the first indication to suspend the delivery of therapy based on the detected posture state of the patient; and
suspending the delivery of therapy based on the receipt of the first indication.

12. The method of claim 1, further comprising detecting, via a processor, the posture state of the patient based on output of a posture state sensor, wherein the posture state sensor comprises an accelerometer sensor.

13. The method of claim 1, wherein the therapy information comprises therapy information defining therapy groups active for delivery of therapy according to the detected posture state of the patient.

14. The method of claim 1, wherein resuming the delivery of therapy to the patient via the medical device in response to the receipt of the first indication comprises resuming the detection of a posture of the patient and controlling the delivery of the therapy according to the detected posture state of the patient.

15. The method of claim 1, further comprising:
controlling the delivery of the therapy to the patient according to a detected posture state of the patient; and
receiving, prior to receiving the first indication, a third indication from the external device to suspend the delivery of the therapy to the patient.

16. The method of claim 1, further comprising periodically storing therapy information over a period of time after the therapy is initialized, wherein the therapy information indicated by the second indication comprises the periodically stored therapy information different from that of therapy information defining the therapy when suspended.

17. The method of claim 1, wherein the input from the user is indicated to the external device via a user interface of the external device.

18. The system of claim 1, further comprising a user interface configured to receive the input from the user indicating that the delivery of therapy should be resumed.

19. The method of claim 1, wherein the first indication received from an external device to resume delivery of therapy includes the second indication indicating the therapy information to define the therapy delivered to the patient when resumed.

20. The method of claim 1, wherein the second indication indicating the therapy information is generated by the external device based on input from a user indicating the therapy information.

21. A system comprising:
a therapy module configured to deliver therapy to a patient according to a detected posture state of the patient; and
a processor configured to receive a first indication from an external device to resume delivery to the patient of therapy that was suspended, wherein the received first indication is generated by the external device based on input from a user indicating that the delivery of therapy should be resumed, receive a second indication from the external device, after suspension of the therapy, indicating therapy information to define the therapy to be delivered to the patient when the therapy is resumed, and resume delivery of therapy to the patient via the therapy module in response to the receipt of the first indication to resume the delivery of therapy, wherein the delivery of therapy is resumed according to the therapy information, and wherein the therapy that was suspended comprises therapy delivered to the patient according to the detected posture state of the patient.

22. The system of claim 21, wherein the therapy information comprises therapy information defining one or more aspects of the therapy delivered according to the detected posture state of the patient prior to the therapy being suspended.

23. The system of claim 21, wherein the therapy information comprises therapy information defined at approximately a time the delivery of stimulation therapy was suspended.

24. The system of claim 21, wherein the therapy information comprises therapy information defined when the delivery of stimulation therapy was initialized.

25. The system of claim 21, wherein the therapy information comprises therapy information defined prior to the therapy being suspended but after the therapy was initialized.

26. The system of claim 21, wherein the therapy information comprises therapy information associated with a posture state of the patient detected at a time when the therapy is resumed.

27. The system of claim 21, wherein the external device is a clinician programmer.

28. The system of claim 21, wherein the processor is configured to send the therapy information to the external device, and receive a third indication from the external device confirming that the therapy should be resumed according to the obtained therapy information.

29. The system of claim 21, wherein the therapy comprises electrical stimulation therapy.

30. The system of claim 21, wherein the therapy that was suspended further comprises therapy delivered to the patient not according to the detected posture state of the patient.

31. The system of claim 21, further comprising the external device configured to generate the indication.

32. The system of claim 21, further comprising a posture state sensor, wherein the processor is configured to detect the posture state of the patient based on output of the posture state sensor, control the delivery of the therapy via the therapy module based on the detected posture state of the patient, subsequently receive the first indication to suspend the delivery of therapy based on the detected posture state of the patient, and suspend the delivery of therapy based on the receipt of the first indication.

33. The system of claim 21, further comprising a posture state sensor, wherein the processor is configured to detect the posture state of the patient based on output of the posture state sensor, wherein the posture state sensor comprises an accelerometer sensor.

34. The system of claim 21, wherein the therapy information comprises therapy information defining therapy groups active for delivery of therapy according to the detected posture state of the patient.

35. The system of claim 21, wherein the processor is configured to resume the detection of a posture of the patient and deliver the therapy according to the detected posture state of the patient.

36. The system of claim 21, wherein the processor is configured to deliver the therapy to the patient according to a detected posture state of the patient, and receive, prior to receiving the first indication, a third indication from the external device to suspend the delivery of the therapy to the patient.

37. The system of claim 21, wherein the processor is configured to periodically store current therapy information after the therapy is initialized, wherein the therapy information indicated by the second indication includes the periodically stored therapy information, wherein the periodically stored therapy information is different from that of therapy information defining the therapy when suspended.

38. The system of claim 21, wherein the first indication received from an external device to resume delivery of therapy includes the second indication indicating a therapy information to define the therapy delivered to the patient when resumed.

39. The system of claim 21, wherein the first indication indicating the therapy information is generated by the external device based on input from a user indicating the therapy information.

40. A system comprising:
  means for receiving a first indication from an external device to resume delivery to a patient of therapy that was suspended, wherein the therapy that was suspended comprises therapy delivered to the patient via a medical device according to a detected posture state of the patient, and wherein the received first indication is generated by the external device based on input from a user indicating that the delivery of therapy should be resumed;
  receiving a second indication from the external device, after suspension of the therapy, indicating therapy information to define the therapy to be delivered to the patient when resumed;
  and
  means for resuming the delivery of therapy to the patient via the medical device in response to the receipt of the first indication to resume the delivery of therapy, wherein the delivery of therapy is resumed according to the therapy information.

41. A computer-readable storage medium comprising instructions for causing one or more processors to:
  receive a first indication from an external device to resume delivery to a patient of therapy that was suspended, wherein the therapy that was suspended comprises therapy delivered to the patient via a medical device according to a detected posture state of the patient, and wherein the received first indication is generated by the external device based on input from a user indicating that the delivery of therapy should be resumed;
  receive a second indication from the external device, after suspension of the therapy, indicating therapy information to define the therapy to be delivered to the patient when resumed;
  and
  resume the delivery of therapy to the patient via the medical device in response to the receipt of the first indication to resume the delivery of therapy, wherein the delivery of therapy is resumed according to the therapy information.

* * * * *